(12) United States Patent
Ding et al.

(10) Patent No.: US 7,238,694 B2
(45) Date of Patent: Jul. 3, 2007

(54) RIFAMYCIN IMINO DERIVATIVES EFFECTIVE AGAINST DRUG-RESISTANT MICROBES

(75) Inventors: Charles Z. Ding, Plano, TX (US); Yafei Jin, Dallas, TX (US); Jamie C. Longgood, Carrollton, TX (US); Zhenkun Ma, Dallas, TX (US); Jing Li, Dallas, TX (US); In Ho Kim, Flower Mound, TX (US); Keith P. Minor, Dallas, TX (US); Susan Harran, Dallas, TX (US)

(73) Assignee: Cumbre Pharmaceuticals, Inc., Dallas, TX (US)

( * ) Notice: Subject to any disclaimer, the term of this patent is extended or adjusted under 35 U.S.C. 154(b) by 223 days.

(21) Appl. No.: 11/034,279

(22) Filed: Jan. 12, 2005

(65) Prior Publication Data

US 2005/0209210 A1 Sep. 22, 2005

Related U.S. Application Data

(60) Provisional application No. 60/536,018, filed on Jan. 13, 2004.

(51) Int. Cl.
*C07D 498/08* (2006.01)
*C07D 519/00* (2006.01)
*A61K 31/4709* (2006.01)
*A61K 31/496* (2006.01)
*A61P 31/04* (2006.01)

(52) U.S. Cl. ............................ 514/253.04; 514/253.08; 514/312; 540/456

(58) Field of Classification Search ................ 540/456; 514/253.04, 253.08, 312
See application file for complete search history.

(56) References Cited

U.S. PATENT DOCUMENTS 4,681,938 A 7/1987 Traxler
5,786,350 A 7/1998 Occelli et al.

FOREIGN PATENT DOCUMENTS

CH 562831 6/1975
WO WO 02/09758 A2 2/2002
WO WO 03/045319 A2 6/2003

OTHER PUBLICATIONS

Brufani, M., et al; "Rifamycins: an Insight into Biological Activity Based on Structural Investigations"; J. Mol. Biol., 1974, vol. 87, pp. 409-435.
Mandell, Gerald L., et al.; "Rifamycins"; Principles and Practice of Infectious Diseases; pp. 348-361; Churchill Livingstone (2001).

*Primary Examiner*—Bruck Kifle
(74) *Attorney, Agent, or Firm*—Jackson Walker L.L.P.

(57) ABSTRACT

The present invention relates to rifamycin 3-iminomethylenyl (—CH=N—) derivatives having antimicrobial activities, including activities against drug-resistant microorganisms. The claimed rifamycin derivative has a rifamycin moiety covalently linked to a linker through an iminomethylenyl (—CH=N—) group at the C-3 carbon of the rifamycin moiety and the linker is, in turn, covalently linked to a quinolone structure or its pharmacophore within the DNA gyrase and topoisomerase IV inhibitor family. The inventive rifamycins are novel and exhibit activity against both rifampin and ciprofloxacin-resistant microorganisms.

51 Claims, 5 Drawing Sheets

RIFAMYCIN IMINO DERIVATIVES EFFECTIVE AGAINST DRUG-RESISTANT MICROBES

This application claims priority to U.S. Provisional Patent Application Ser. No. 60/536,018, entitled "RIFAMYCIN IMINO DERIVATIVES EFFECTIVE AGAINST DRUG-RESISTANT MICROBES" filed on Jan. 13, 2004, having Charles Z. Ding, Yafei Jin, Jamie Carol Longgood, and Zhenkun Ma, listed as the inventor(s), the entire content of which is hereby incorporated by reference.

BACKGROUND

This invention relates to compounds of rifamycin derivatives having antimicrobial activities, their compositions, and methods for treatment and prevention of microbial infections. More particularly, the rifamycin derivative of the current invention is a rifamycin moiety covalently linked to a linker through an iminomethylenyl group (—CH=N—) at the C-3 carbon of the rifamycin moiety and the linker is, in turn, covalently linked to a quinolone moiety. The rifamycin derivatives are active against drug-resistant microorganisms with reduced frequency of developing mutational resistance in the microorganisms.

Rifamycins are natural products with potent antimicrobial activity. Examples of the naturally-occurring rifamycins are rifamycin B, rifamycin O, rifamycin R, rifamycin U, rifamycin S, rifamycin SV and rifamycin Y (Brufani, M., Cerrini, S., Fedeli, W., Vaciago, A. *J. Mol. Biol.* 1974, 87, 409-435). The therapeutic applications of the naturally-occurring rifamycins are limited due to their poor pharmacokinetics and oral bioavailability, weak activity against Gram-negative pathogens and low distribution into the infected tissues. Significant efforts have been made toward identifying semi-synthetic rifamycin derivatives to address the deficiencies. As a result, many semi-synthetic rifamycin derivatives with improved spectrum and pharmacological profiles have been identified. Among the semi-synthetic compounds, rifampin, rifabutin and rifapetine have been developed into therapeutic agents and are currently used for the treatment of tuberculosis and other microbial infections (Farr, B. M. *Rifamycins*, in *Principles and Practice of Infectious Diseases*; Mandell, G. L., Bennett, J. E., Dolin, R., Eds.; Churchhill Livingstone: Philadelphia; p348-361).

At present, one of the major problems associated with the rifamycin class of antimicrobial agents, like rifampin, is their rapid development of microbial resistance. Mutations in the target RNA polymerase are mainly responsible for the high frequency of microbial resistance to rifamycins. Consequently, rifamycins are currently used only in combination therapies with other antibiotics to minimize the development of resistance to this class of drugs. Rifamycin compounds of the current invention are designed to address both the rifamycin and quinolone resistance problems by attaching a quinolone core or quinolone antibiotic pharmacophore to the C-3 position of the rifamycin core structure. The resulting rifamycin compounds exert their antimicrobial activity through multiple antibacterial mechanisms targeting bacterial RNA polymerase, DNA gyrase and DNA topoisomerase IV and therefore exhibit reduced frequency of resistance.

Reference is made to U.S. Pat. No. 5,786,350 that discloses a series of C-36 derivatives of rifamycin, including derivatives formed by linking the C-3 carboxy group of a quinolone to the C-36 position of a rifamycin molecule through a chemically or metabolically labile ester group. The compounds of the current invention are structurally distinct from the previously disclosed compounds in several ways: 1) the linking point of rifamycin is the C-3 position rather than the C-36 position; 2) the linking point of the quinolone core is the C-7 position of the quinolone rather than the C-3 position carboxylic acid; and 3) the linker group contains a stable hydrazone linkage in the current inventive rifamycins rather than a metabolically unstable ester in the referenced compounds.

Reference is also made to PCT application WO 03/045319 A2 that discloses rifamycin derivatives formed by linking rifamycin and a therapeutic drug and the use of these rifamycin derivatives as vehicles for delivering the therapeutic drug. The current non-pro-drug invention differs from the referenced pro-drug strategy. In addition, this reference failed to demonstrate by specific examples that any drug is introduced to the C-3 position of a rifamycin molecule. The reference also failed to demonstrate by example that a quinolone antibiotic or its pharmacophore structure is linked to any position of rifamycin molecule.

SUMMARY

One aspect of the current invention relates to compounds of general Formula I:

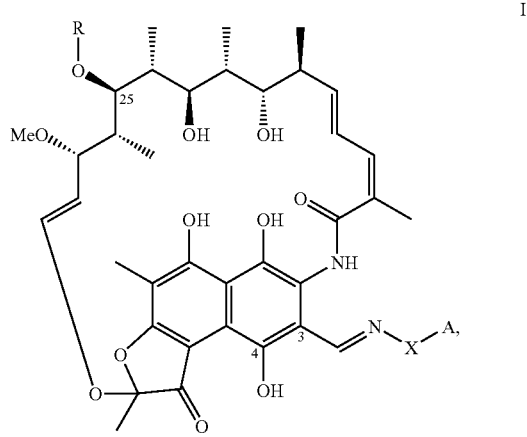

and its corresponding quinones, or its salts, hydrates or prodrugs thereof.

In this Formula, a therapeutic agent, such as an antibiotic or its pharmacophore ("A") is covalently bonded or coupled to a rifamycin moiety, through a linker ("X") and through an imino group (—C(H)=N—) to the C-3 carbon of the rifamycin molecule.

A preferred R comprises hydrogen, acetyl, or —COCH$_2$R$_{10}$, wherein, R$_{10}$ represents hydrogen, halogen, hydroxyl, thio, amino, (C$_1$-C$_6$)alkoxy, (C$_1$-C$_6$)alkylthio, (C$_1$-C$_6$)acyloxy, (C$_1$-C$_6$)alkylamino, di(C$_1$-C$_6$)alkylamino, or heterocyclo group.

A preferred linker ("X") in the above structure comprises any combination of 1 to 5 groups selected from (C$_1$-C$_6$) alkylene, (C$_3$-C$_8$)cycloalkylene, arylene, heteroarylene, bivalent heterocyclic group containing 1 to 3 heteroatoms, —C(=O)—, —C(=N—O—R$_{11}$)—, —C=N—, —O—, —S(O)$_n$—, wherein n is a number between 0 and 2, or —N(R$_{12}$)—, wherein the carbon or nitrogen atoms of the linker group are optionally substituted by 1 to 3 substituents selected from (C$_1$-C$_6$)alkyl, substituted (C$_1$-C$_6$)alkyl, amino, (C$_1$-C$_6$)alkylamino, di(C$_1$-C$_6$)alkylamino, hydroxyl, (C$_1$-

$C_6$)alkoxy, and heterocyclic group; $R_{11}$ and $R_{12}$ are independently selected from hydrogen, ($C_1$-$C_6$)alkyl, aryl, heteroaryl, and heterocyclo groups.

A preferred therapeutic structure or its pharmacophore ("A") comprises Formula II or III:

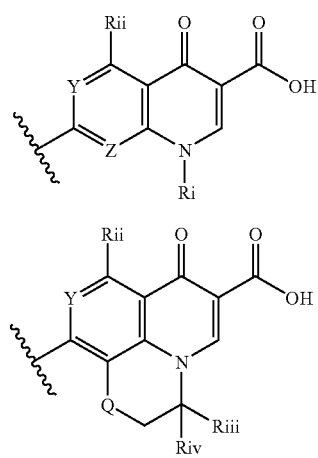

wherein $R_i$ represents ($C_1$-$C_6$)alkyl, ($C_3$-$C_6$)cycloalkyl, substituted ($C_3$-$C_6$)cycloalkyl, aryl, substituted aryl, heteroaryl, or substituted heteroaryl; $R_{ii}$ represents hydrogen, halogen, amino, nitro or methyl group; $R_{iii}$ and $R_{iv}$ independently represent hydrogen, ($C_1$-$C_6$)alkyl or $R_{iii}$ and $R_{iv}$ together with the carbon atom they are attached to form a 3- to 6-membered ring; Y represents C—H, C—F, or N; Z represents C—H, C—F, C—CN, C—$CF_3$, C—Cl, C—Me, C—OMe, C—$OCH_2F$, C—$OCHF_2$, or N; and Q represents $CH_2$, O or S, and any therapeutically acceptable salts or prodrugs. A specific therapeutic molecule ("A") may comprise any of the structural formulas related to quinolones shown in FIG. 2. The preferred therapeutic quinolone molecules ("A"), as shown in the figures described above are covalently coupled or bonded to the linker which in turn is covalently coupled or bonded to the C-3 carbon of the rifamycin through an imino group (—CH=N—).

Another aspect of the current invention comprises a method of treating a microbial infection in a subject; wherein the subject is any species of the animal kingdom. The microbial infection can be caused by a bacterium or microorganism. The term "subject" refers more specifically to human and animals, wherein the animals can be raised for: pets (e.g. cats, dogs, etc.); work (e.g. horses, cows, etc.); food (chicken, fish, lambs, pigs, etc); and all others known in the art. The method comprises administering an effective amount of one or more compounds of the present invention to the subject suffering from a microbial infection. The compounds of the current invention are effective against drug-resistant microbes and, in particular, against rifamycin-resistant microbes.

DETAILED DESCRIPTION OF THE INVENTION

Figure 1:
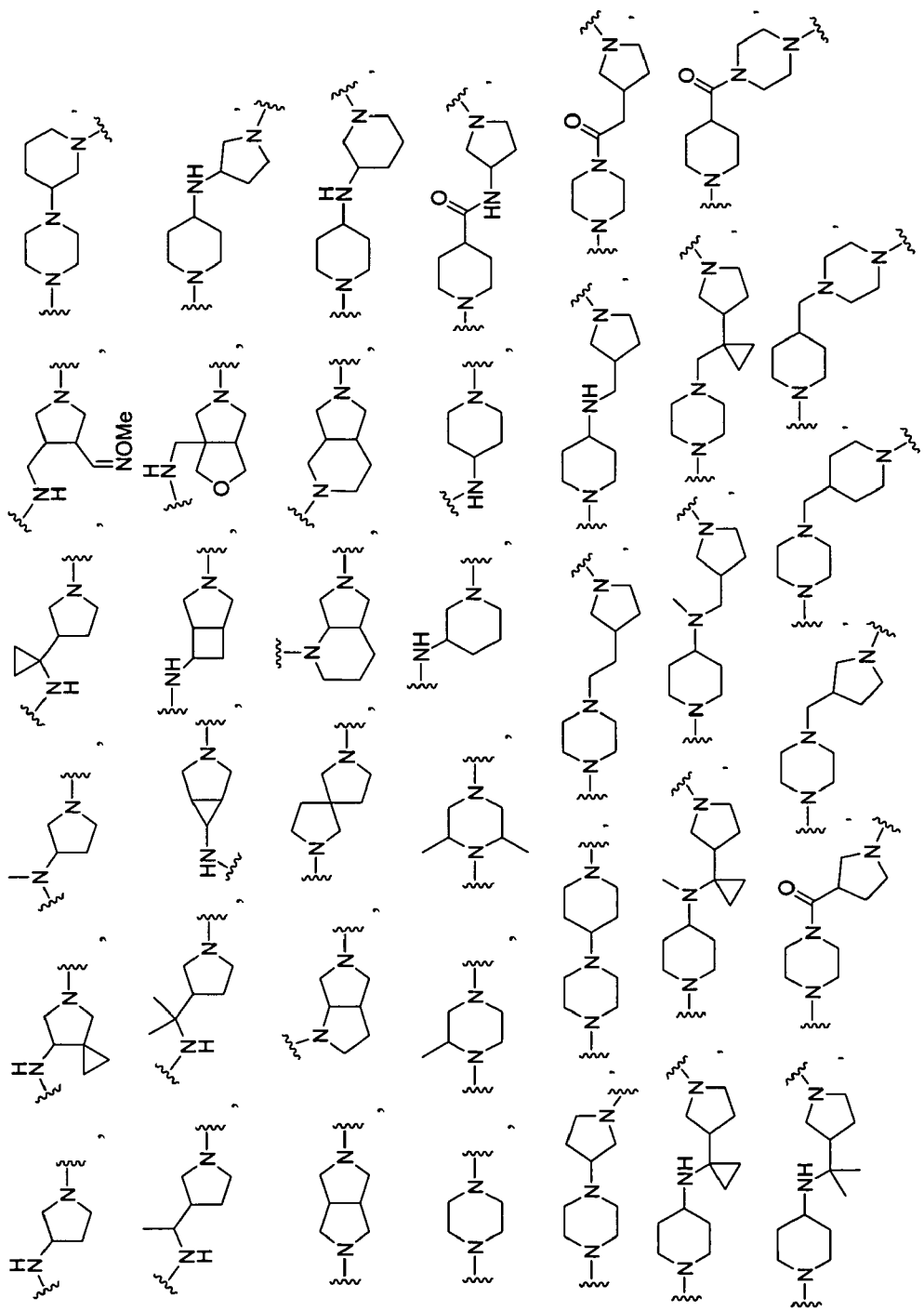
FIG. 1 shows a group of representative linkers "X"

Terms:

The term "alkenyl," as used herein, refers to a monovalent straight or branched chain group containing at least one carbon-carbon double bond. The alkenyl groups of this invention can be optionally substituted.

The term "alkenylene," as used herein, refers to a bivalent straight or branched chain group containing at least one carbon-carbon double bond. The alkenylene groups of this invention can be optionally substituted.

The term "alkyl," as used herein, refers to a monovalent, saturated, straight or branched chain hydrocarbon group. Examples of alkyl group include methyl, ethyl, propyl, iso-propyl, n-butyl, iso-butyl, tert-butyl, neo-pentyl, and n-hexyl. The alkyl groups of this invention can be optionally substituted.

The term "alkylene," as used herein, refers to bivalent saturated, straight or branched chain hydrocarbon structures. Examples of alkylene groups include methylene, ethylene, propylene, iso-propylene, n-butylene, isobutylene, and n-hexylene. The alkylene groups of this invention can be optionally substituted.

The term "alkylamino," as used herein, refers to an amino group (—$NH_2$), wherein one hydrogen atom is replaced by an alkyl group. Examples of alkylamino include methylamino, ethylamino, propylamino, and isopropylamino.

The term "alkylthio," as used herein, refers to an alkyl group, as defined herein, attached to the parent molecular group through a sulfur atom. Examples of alkylthio include methylthio, ethylthio, propylthio, and isopropylthio.

The term "alkoxy," as used herein, refers to an alkyl group, as previously defined, attached to the parent molecular group through an oxygen atom. Examples of alkoxy include methoxy, ethoxy, propoxy, iso-propoxy, n-butoxy, tert-butoxy, neo-pentoxy and n-hexoxy. The alkoxy groups of this invention can be optionally substituted.

The term "alkynyl," as used herein, refers to a monovalent straight or branched chain group of two to six carbon atoms containing at least one carbon-carbon triple bond. Examples of alkynyl include ethynyl, propynyl, and butynyl. The alkynyl groups of this invention can be optionally substituted.

The term "alkynylene," as used herein, refers to a bivalent straight or branched chain group of two to six carbon atoms containing at least one carbon-carbon triple bond. Examples of alkynylene include ethynylene, propynylene, and butynylene. The alkynylene groups of this invention can be optionally substituted.

The term "aprotic solvent," as used herein, refers to a solvent that is relatively inert to protonic activity, i.e., not acting as a proton donor. Examples include hexane, toluene, dichloromethane, ethylene dichloride, chloroform, tetrahydrofuran, N-methylpyrrolidinone, diethyl ether.

The term "aryl" as used herein refers to a monovalent carbocyclic aromatic group including phenyl, naphthyl, and anthracenyl.

The term "arylene" as used herein refers to bivalent carbocyclic aromatic groups which can be optionally substituted.

The term "benzyl," as used herein, refers to —CH$_2$C$_6$H$_5$.

The term "benzyloxy," as used herein, refers to a benzyl group, as defined herein, attached to the parent molecular group through an oxygen atom.

The term "carboxaldehyde," as used herein, refers to —CHO.

The term "cycloalkyl," as used herein, refers to a monovalent saturated carbocyclic group having three to eight carbons such as cyclopropyl, cyclobutyl, cyclopentyl, cyclohexyl, cycloheptyl and cyclooctyl.

The term "cycloalkylene," as used herein, refers to bivalent saturated carbocyclic groups having three to eight carbons. The cycloalkylene groups can be optionally substituted.

The term "formyl," as used herein, refers to —CH(=O).

The term "halogen," as used herein, refers to fluorine, chlorine, bromine and iodine atoms and the term "halo" refers to —F, —Cl, —Br, and —I as substituent.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene group can be optionally substituted.

The term "heteroatom," as used herein, refers to oxygen, nitrogen or sulfur atom.

The term "heterocycloalkyl" as used herein, refers to a non-aromatic five-, six- or seven-membered ring or a bi- or tri-cyclic group having one or more heteroatoms independently selected from oxygen, sulfur and nitrogen wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to an aryl or heteroaryl ring. Representative heterocycles include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofurranyl. The heterocycloalkyl groups of this invention can be optionally substituted with one, two, or three substituents independently selected from —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -cycloheteroalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "heterocycloalkylene" as used herein, refers to a bivalent non-aromatic five-, six- or seven-membered ring having one or more heteroatoms independently selected from oxygen, sulfur and nitrogen wherein each 5-membered ring has zero to one double bonds and each six-membered ring has zero to 2 double bonds. The heterocycloalkylene groups of this invention can be optionally substituted.

The term "hydrate" as used herein, refers to a molecule that has been hydrated, or reacted with water in a hydration reaction. In a hydration reaction, molecules of water react with a compound, but the H—OH bond is not split. The water is usually split off from the hydrated compound by heat, yielding the anhydrous compound.

The term "hydroxyl," as used herein, refers to —OH.

The term "protecting group", as used herein, refers to an easily removable group to which are known in the art to protect a functional group, such as hydroxyl and amino, against undesirable reaction during synthetic procedures and to be selectively removable. The use of protecting groups is well-known in the art for protecting groups against undesirable reactions during a synthetic procedure and many such protecting groups are known (T. H. Greene and P. G. M. Wuts, Protective Groups in Organic Synthesis, 2nd edition, John Wiley & Sons, New York, 1991).

The term "pharmacophore", as used herein, refers to structural element in a drug or bioactive molecule that is critical for biological interaction to its biological target and its subsequent biological effects. For example, for fluoroquinolone antibiotics, such as ciprofloxacin, its pharmacophore is 4-quinolone-3-carboxylic acid structural element.

The term "pharmaceutically acceptable prodrugs," as used herein refers to the prodrugs of the compounds of the current invention which are suitable for use in humans and animals with acceptable toxicity, irritation, allergic response, and the like, commensurate with a reasonable benefit to risk ratio, and effective for their intended use. The term "prodrug," as used herein, represents compounds which can be transformed in vivo to parent compounds defined above.

The term "pharmaceutically acceptable salt," as used herein refers to those salts which are suitable for use in humans and animals with acceptable toxicity, irritation, and allergic response, etc., and are commensurate with a reasonable benefit to risk ratio. Pharmaceutically acceptable salts are well known in the art. The salts can be prepared in situ during the final step of isolation and purification of the compounds of the invention or separately prepared by reacting the compounds of the invention with an acid or base. Examples of pharmaceutically acceptable salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid. Examples of pharmaceutically acceptable salts are salts of an acid group formed with inorganic bases such as sodium hydroxide, sodium carbonate, sodium phosphate, etc. Other metal salts include lithium, potassium, calcium, and magnesium. Additional pharmaceutically acceptable salts include ammonium cations formed with counterions such as halide, hydroxide, carboxylate, sulfate, phosphate, nitrate, loweralkyl sulfonate, and aryl sulfonate.

The term "prodrug," as used herein, represents compounds which can be transformed in vivo to their active parent compounds defined herein.

The term "rifamycin moiety," as used herein, comprises both its phenolic and quinone forms of the rifamycin core structure (ansa-chain and naphthalene ring).

The term "substituted aryl," as used herein, refers to an aryl group, as defined herein, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heteroaryl" as used herein refers to a heteroaryl group as defined herein substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heterocycloalkyl," as used herein, refers to a heterocycloalkyl group, as defined above, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituent," as used herein, refers to —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

Abbreviations

Abbreviations as used herein have the meanings known by one skilled in the art. Specifically, Ac represents acetyl group, AOC represents allyloxycarbonyl group, BOC represents t-butoxycarbonyl group, Bn represents benzyl group, Bu represents butyl group, Bz represents benzoyl group, Cbz represents benzyloxycarbonyl group, CDI represents carbonyldiimidazole, DCM represents dichloromethane, DMAP represents 4-N,N-dimethylaminopyridine, DME represents 1,2-dimethoxyethane, DMF represents N,N-dimethylformamide, DMSO represents dimethyl sulfoxide, Et represents ethyl group, EtOAc represents ethyl acetate, Me represents methyl group, MEM represents 2-methoxyethoxymethyl group, MOM represents methoxymethyl group, NMP represents N-methylpyrrolidinone, Ph represents phenyl group, Pr represents propyl group, TEA represents triethylamine, TFA represents trifluoroacetic acid, THF represents tetrahydrofuran, TMS, trimethylsilyl group, and Ts represents p-toluenesulfonyl group.

Broadly, one aspect of the present invention comprises a compound having Formula I:

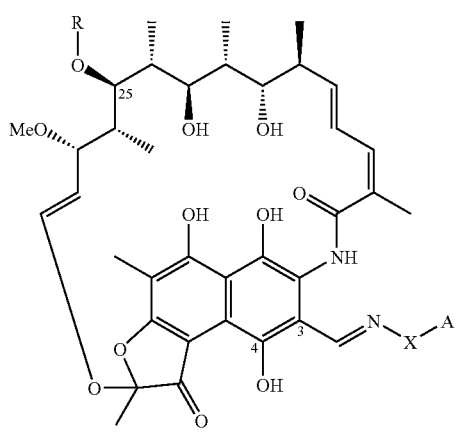

or its corresponding quinone form, or its salt, hydrate, prodrug or a mixture thereof;

wherein:

A is a therapeutic drug or antibacterial agent or its pharmacophore covalently coupled to a linker ("X"), wherein A preferably comprises a quinolone core or its pharmacophore;

X is absent or is a linker group consisting of any combination of 1 to 5 groups selected from:
  (a) $(C_1-C_6)$alkylene,
  (b) $(C_3-C_8)$cycloalkylene,
  (c) arylene,
  (d) heteroarylene,
  (e) bivalent heterocyclic group containing 1 to 3 heteroatoms,
  (f) —C(=O)—,
  (g) —C(=N—O—$R_{11}$)—, wherein $R_{11}$ represents hydrogen, $(C_1-C_6)$alkyl, or substituted $(C_1-C_6$ alkyl),
  (h) —C=N—,
  (i) —O—,
  (j) —S(O)$_n$—, wherein n is number between 0 and 2, and
  (k) —N($R_{12}$)—, wherein $R_{12}$ represents hydrogen, $(C_1-C_6)$alkyl, or substituted $(C_1-C_6$ alkyl),
    wherein the carbon or nitrogen atoms of the linker group are optionally substituted by 1 to 3 substituents selected from $(C_1-C_6)$alkyl, substituted $(C_1-C_6)$ alkyl, heterocycloalkyl, amino, $(C_1-C_6)$alkylamino, di$(C_1-C_6)$alkylamino, hydroxyl, or $(C_1-C_6)$alkoxy; and R is hydrogen, acetyl, or —COCH$_2$R$_{10}$, wherein, $R_{10}$ represents hydrogen, halogen, hydroxyl, thio, amino, $(C_1-C_6)$alkoxy, $(C_1-C_6)$alkylthio, $(C_1-C_6)$acyloxy, $(C_1-C_6)$alkylamino, di$(C_1-C_6)$alkylamino, or heterocyclo group.

The compound of Formula I may form salts which are also within the scope of this invention. Reference to a compound of Formulas I herein is understood to include reference to salts thereof, unless otherwise indicated. The term "salt(s)," as employed herein, denotes acidic and/or basic salts formed with inorganic and/or organic acids and bases. In addition, when a compound of Formula I contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of Formula I may be formed, for example, by reacting a compound of Formula I with an amount of acid or base, such as an equivalent amount, in a medium such as one in which the salt precipitates or in an aqueous medium followed by lyophilization.

The compounds of Formula I which may contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formula I which may contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), arylalkyl halides (e.g., benzyl and phenethyl bromides), and others.

Compounds of Formula I, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

In addition, compounds of Formula I may have prodrug forms. Any compound that will be converted in vivo to provide the bioactive agent (i.e., a compound of Formula I) is a prodrug within the scope and spirit of the invention.

For example, pro-drug compounds of Formula I may be carboxylate ester moieties. A carboxylate ester may be conveniently formed by esterifying any of the carboxylic acid functionalities found on the disclosed ring or chain structure(s).

The compounds of the current invention are rifamycin derivatives of Formula I and its quinone form or their salts, hydrates, prodrugs or a mixture thereof, which have been labeled at the C-3, C-4 and C-25 positions for illustration purposes. Formula I and its quinone form are different in their oxidation states and can be transformed from one to another by utilizing an oxidation or reduction reaction. The compounds of the current invention contain many asymmetric and geometric centers. In some cases, one or more of the asymmetric or geometric centers can be converted to their opposite configurations. These stereoisomers of rifamycin are expected to have antimicrobial activity and therefore are within the scope of the invention.

EXAMPLE 1

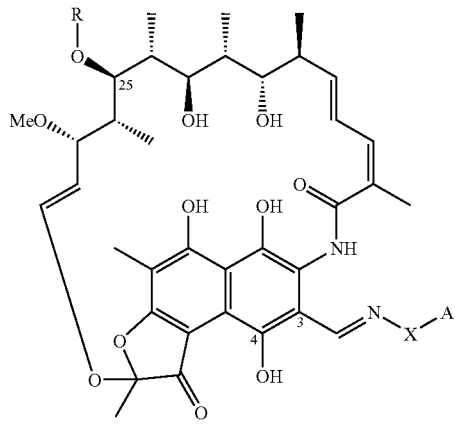

R group of Formula I above represents a hydrogen, an acetyl or a substituted acetyl group of formula —C(O)CH$_2$R$_{10}$. In the natural form, rifamycins have an acetyl group at this position. Chemical or enzymatic hydrolysis of the acetyl group provides the de-acetylated compounds wherein R is hydrogen. The de-acetylated compounds can be further transformed to compounds where R is a group of formula —C(O)CH$_2$R$_{10}$. R$_{10}$ can be a variety of groups such as hydrogen, halogen, hydroxyl, thio, amino, (C$_1$-C$_6$)alkyl, (C$_1$-C$_6$)alkoxy, (C$_1$-C$_6$)alkylthio, (C$_1$-C$_6$)acyloxy, (C$_1$-C$_6$)alkylamino, di(C$_1$-C$_6$)alkylamino, aryl, heteroaryl, and heterocyclic groups, which are all optionally substituted.

X represents a linker group with various compositions and structural elements. X may consist of any combination of 1 to 5 of the following structural elements: (C$_1$-C$_6$)alkylene, (C$_1$-C$_6$)alkenylene, (C$_1$-C$_6$)alkynylene, (C$_3$-C$_8$)cycloalkylene, arylene, heteroarylene, and bivalent heterocyclic groups containing 1 to 3 heteroatoms. The linker group can be optionally interrupted by 1 to 3 groups selected from —N(R$_{11}$)—, —O—, —S—, —S(O)—, —S(O)$_2$—, —C(=O)—, —C(=N—O—R$_{12}$)—, —C=N—, and the carbon or nitrogen atoms of the linker group can be optionally substituted by 1 to 3 substituents selected from (C$_1$-C$_6$)alkyl, substituted (C$_1$-C$_6$)alkyl, heterocycloalkyl, amino, (C$_1$-C$_6$)alkylamino, di(C$_1$-C$_6$)alkylamino, hydroxyl, or (C$_1$-C$_6$)alkoxy. Examples of the linker groups are shown by FIG. 1. These examples are intended for illustration purposes only and are not intended to limit the scope of this invention.

As illustrated by Formula I and FIG. 1, the left-hand side of the linker "X" is attached to the C-3 position of a rifamycin molecule through an imino group and the right-hand side of the linker is attached to an antibiotic structure or pharmacophore represented by "A."

Preferably, "A" is a quinolone core structure selected from formula II, and III:

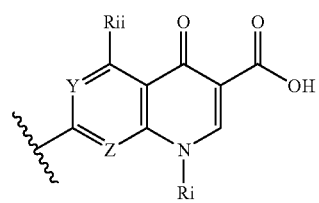

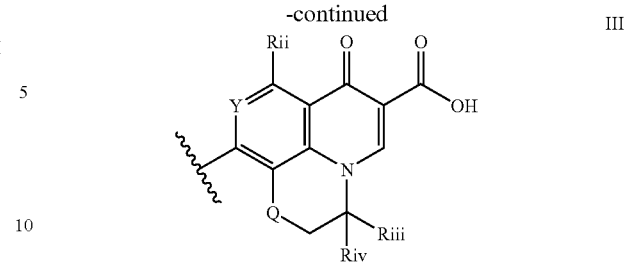

wherein the substituents or groups in formula II, and III have the following meanings: R$_i$ represents (C$_1$-C$_6$)alkyl, (C$_3$-C$_6$) cycloalkyl, substituted (C$_3$-C$_6$)cycloalkyl, aryl, substituted aryl, heteroaryl, or substituted heteroaryl; R$_{ii}$ represents hydrogen, halogen, amino, nitro or methyl group; R$_{iii}$ and R$_{iv}$ independently represent hydrogen, (C$_1$-C$_6$)alkyl or R$_{iii}$ and R$_{iv}$ together with the carbon atom they are attached to form a 3- to 6-membered ring. Y represents C—H, C—F, or N; Z represents C—H, C—F, C—CN, C—CF$_3$, C—Cl, C—Me, C—OMe, C—OCH$_2$F, C—OCHF$_2$, or N. Q represents CH$_2$, O or S.

Figure 2:
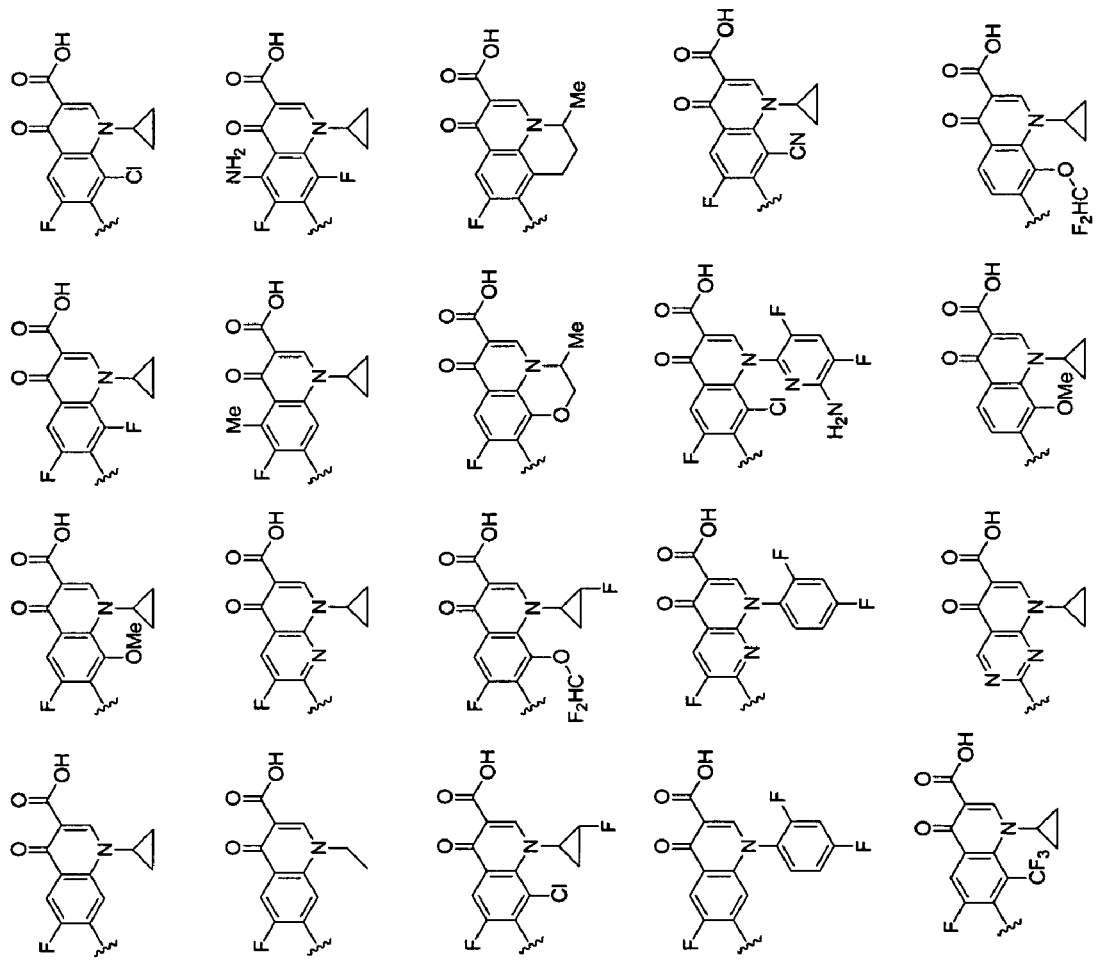
FIG. 2 shows a group of representative quinolone structures "A"

In another preferred embodiment, R is an acetyl group and A is a quinolone structure selected from FIG. 2.

In yet another preferred embodiment, R is a hydrogen and A is a quinolone structure selected from FIG. 2.

EXAMPLE 2

Administration to a Subject:

The pharmaceutical composition of the present invention comprises a therapeutically effective amount of a compound of the current invention formulated together with one or more pharmaceutically acceptable carriers. Injectable preparations can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a drug, it is often desirable to slow the absorption of the drug through subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and the following: 1) fillers or extenders such as starches, lactose, sucrose, glucose, mannitol, and silicic acid, 2) binders such as, carboxymethylcellulose, alginates, gelatin, polyvinylpyrrolidinone, sucrose, and acacia, 3) humectants such as glycerol, 4) disintegrating agents such as agar-agar, calcium carbonate, potato or tapioca starch, alginic acid, certain silicates, and sodium carbonate, 5) solution retarding agents such as paraffin, 6) absorption accelerators such as quaternary ammonium compounds, 7) wetting agents such as, cetyl alcohol and glycerol monostearate, 8) absorbents such as kaolin and bentonite clay, and 9) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient only, or preferentially, in a certain part of the intestinal tract, optionally, in a delayed manner. Examples of embedding compositions which can be used include polymeric substances and waxes. The active compounds can also be in microencapsulated form with one or more excipients as noted above.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, eye ointments, powders and solutions are also contemplated as being within the scope of this invention. The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or animal by administering to the patient a therapeutically effective amount of a compound of the invention, in such amounts and for such time as is necessary to achieve the desired therapeutic effects. The term "therapeutically effective amount" of a compound of the invention is meant a sufficient amount of the compound to treat bacterial infections, at a reasonable benefit to risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or animal in single or in divided doses can be in amounts, for example, from 0.1 to 100 mg/kg body weight or preferably from 0.25 to 25 mg/kg body weight. Single dose compositions can contain such amounts or submultiples thereof to make up the daily dose. In general, treatment regimens according to the present invention comprise administration to an infected patient of such treatment from about 10 mg to about 2000 mg of the compounds of this invention per day in single or multiple doses. The compounds of the current invention can be administrated orally, rectally, parenterally, intracisternally, intravaginally, intraperitoneally, topically, bucally, or as an oral or nasal spray.

Biological Activity:

Representative compounds were assayed for antimicrobial activity as follows: Minimum Inhibitory Concentrations (MICs) were determined by the microbroth dilution method as per NCCLS guidelines (National Committee for Clinical Laboratory Standards, 2000). Methods for dilution antimicrobial susceptibility tests for bacteria that grow aerobically, 5th ed. M7-A5. National Committee for Clinical Laboratory Standards, Wayne, Pa.), except that all growth incubations were conducted at 37° C. Bacterial cultures were tested in the following bacteriological media: *S. aureus, S. epidermidis*, and *E. coli* in Cation-Adjusted Mueller-Hinton Broth, *S.* pneumoniae in THY Broth supplemented with 1 mg/mL catalase under 5% $CO_2$ atmosphere, *S. pyogenes* in THY Broth, *E. faecalis* in BHI Broth, *H. influenzae* in BHI Broth supplemented with 0.75 µL of 1 mg/mL NAD and 150 µL of 1 mg/ml hematin per 5 mL, and *M. smegmatis* in Middle-brook Broth plus ADC Enrichment. The antimicrobial activities of the examples of the current invention are shown in Table 1.

S. aureus ATCC 29213, S. epidermidis ATCC 12228, S. pneumoniae ATCC6303, S. pyogenes ATCC 19615 and E. faecalis ATCC 29212 are rifampin-susceptible Gram-positive strains. Rifampin exhibits excellent activity against these organisms with MICs between 0.008 and 1 µg/ml. The compounds of the current invention show similar activity against these strains. *H. influenzae* ATCC 10211 and *E. coli* ATCC 25922 are Gram-negative bacteria. Rifampin has intrinsic weaker activity against these organisms with MICs between 0.24 and 16 µg/ml. Compounds of the current invention demonstrate improved activity against these strains with MICs as low as 0.125 µg/ml. In addition, rifampin exhibits low activity against a mycobacterial strain *M. smegamatis* ATCC 700084 with a MIC 64 µg/ml. While certain compounds of the current invention show potent activity against this strain with a MIC 0.25 µg/ml.

Most importantly, compounds of the current invention demonstrate excellent activity against rifampin-resistant organisms. *S. aureus* ATCC 29213 RpoB$^{H418Y}$ is a rifampin-resistant strain with a mutation in RNA polymerase. This mutation results in a significant increase in the MIC for rifampin to 7.8 µg/ml. Compounds of the current invention exhibit potent activity against this strain with a MIC as low as 0.06 µg/ml. *S. aureus* ATCC 29213 RpoB$^{D417Y}$ is a high level rifampin-resistant strain due to a RNA polymerase mutation with a MIC >64 µg/ml for rifampin. Compounds of the current invention are potent against this highly rifampin-resistant strain with MICs in the 0.06 µg/ml level. Furthermore, compounds of the current invention demonstrated excellent activity against a quinolone-resistant strain *S. aureus* MT 1222 with MIC between 0.008-0.125 µg/ml, as compared to ciprofloxacin at 8 µg/ml.

TABLE 1

Antimicrobial activity (range of MIC, mcg/ml) of selected compounds

| Organism | | rifampin | ciprofloxacin | Example 4-47 |
|---|---|---|---|---|
| *Staphylococcus aureus* ATCC29213 | rifS | 0.008 | 0.25 | 0.008-1 |
| *Staphylococcus aureus* ATCC29213 rpoB$^{H418Y}$ | rifR | 7.8 | 0.25 | 0.06-16 |
| *Staphylococcus aureus* ATCC29213 rpoB$^{D417Y}$ | rifR | >64 | 0.25 | 0.06->64 |
| *Staphylococcus aureus* MT1222[a] gyrA$^{A116E}$ grlB$^{S80F}$ | cipR | 0.004 | 8 | 0.008-0.125 |
| *Staphylococcus epidermidis* ATCC12228 | rifS | 0.03 | 0.125 | 0.008-0.1 |
| *Streptococcus pneumoniae* ATCC6303 | rifS | 0.061 | 1 | 0.008-0.06 |
| *Streptococcus pyogenes* ATCC19615 | rifS | 0.013 | 0.5 | 0.008-0.03 |
| *Enterococcus faecalis* ATCC29212 | rifS | 0.98 | 0.5 | 0.24->64 |
| *Haemophilus influenzae* ATCC10211 | rifS | 0.24 | 0.008 | 0.125-4 |
| *Escherichia coli* ATCC25922 | rifS | 16 | 0.03 | 1->64 |

TABLE 1-continued

Antimicrobial activity (range of MIC, mcg/ml) of selected compounds

| Organism | | rifampin | ciprofloxacin | Example 4-47 |
|---|---|---|---|---|
| *Mycobacterium smegmatis* ATCC700084 | rifS | 64 | 0.125 | 0.25->64 |

[a]For strain MT1222 see: Ince & Hooper, Antimicrobial Agents and Chemotherapy, 2000, 44, 3344-50.

EXAMPLE 3

Synthetic Methods:

The compounds of the current invention can be better understood in connection with the following synthetic schemes. The synthetic procedures shown below in schemes 1 to 4 are for illustration purposes and are not intended for limiting the scope of the invention. It will be apparent to one skilled in the art that the compounds of the current invention can be prepared by a variety of synthetic routes, including but not limited to substitution of appropriate reagents, solvents or catalysts, change of reaction sequence, and variation of protecting groups. The groups R, X, A, $R_1$, $R_2$, $R_3$, $R_4$, Y, Z, and Q in Scheme 1 to 3 (FIGS. 3-5) are as defined above.

Figure 3:
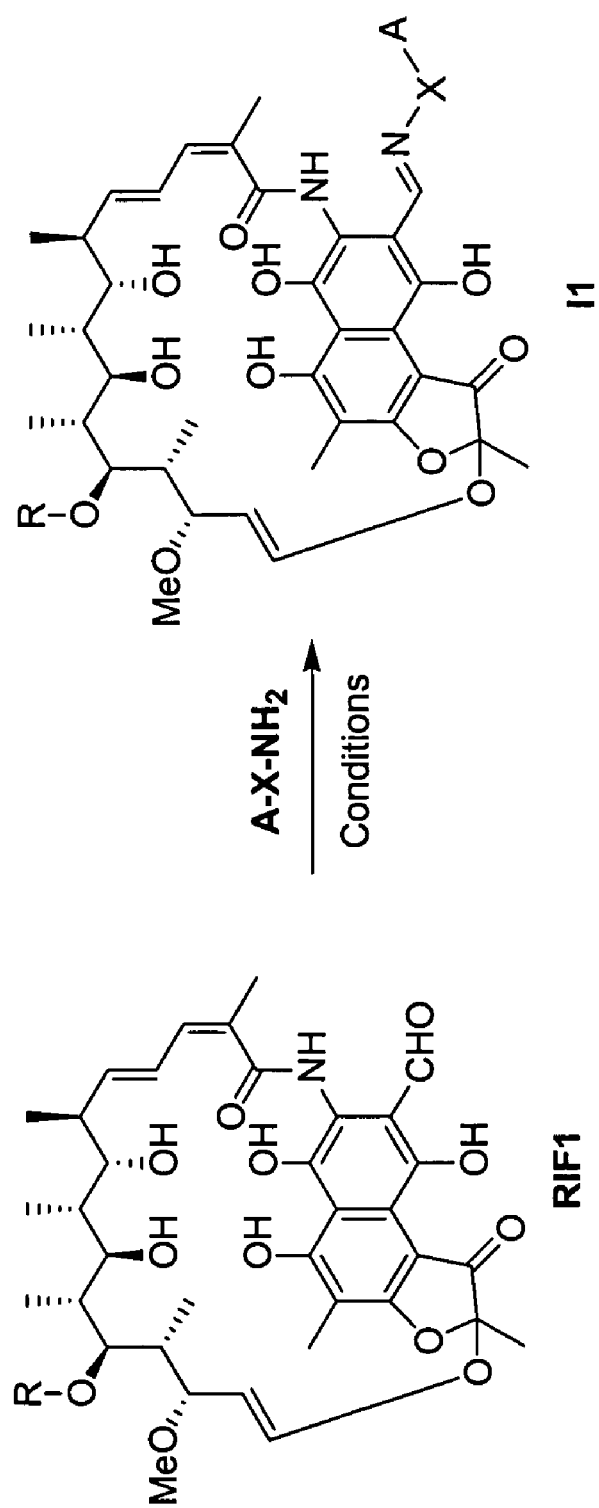
FIG. 3 shows Scheme 1, wherein a rifamycin derivative (RIF1) reacts with a hydrazine molecule A—X—$NH_2$ to produce compounds (I1) of the Formula I of this invention.

Scheme 1 in FIG. 3 illustrates that a rifamycin compound (Ia) of Formula I of this invention can be prepared from 3-formylrifamycin (RIF1) and a compound of formula A—X—$NH_2$. In structure A—X—$NH_2$, the terminal amino group is directly attached to a nitrogen atom of "X" in A—X—$NH_2$ to form a hydrazino group (>N—$NH_2$). The reaction is performed in a protic or aprotic solvent. Examples of solvents suitable for this reaction are THF, DMSO, DMF, NMP, ethanol, isopropanol, methanol, dioxane, acetonitrile, acetic acid, water or any combination of the above. The reaction can be performed at a temperature between –20 to 120° C.

Figure 4:
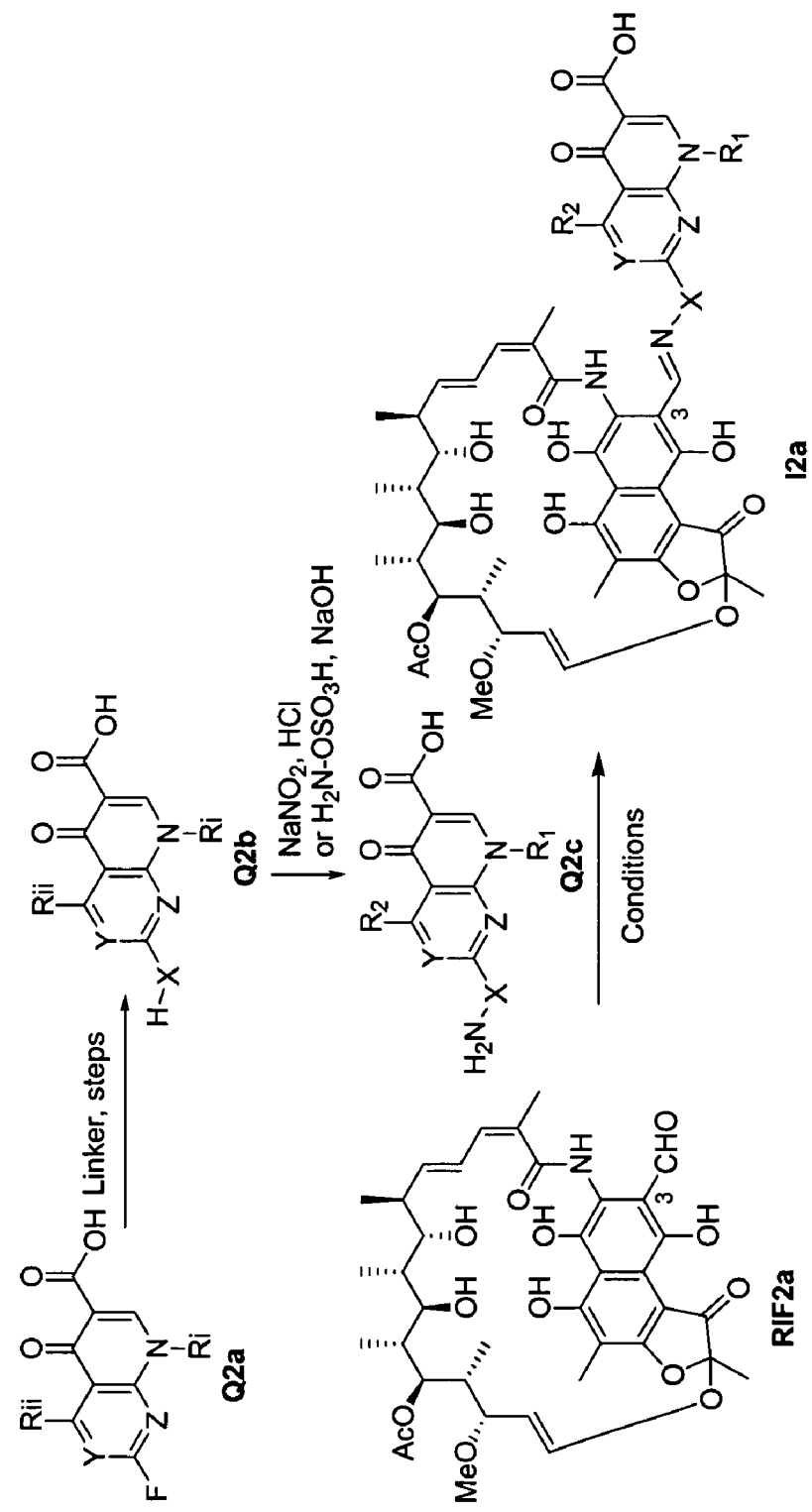
FIG. 4 shows Scheme 2, wherein a rifamycin derivative (RIF2a, 3-formylrifamycin) reacts with a hydrazine quinolone (Q2c) compound. The quinolone can be prepared in a two-step sequence as shown starting from commercially available quinolone (Q2a), displacement by the linker "X" followed by amination.

One specific example for the preparation of compounds of Formula I of this invention is illustrated by Scheme 2 in FIG. 4, where 3-formyl rifamycin SV (RIF2a) reacts with a quinolone compound (Q2c) to give product (I2a). The quinolones (Q2c) can be readily prepared starting from fluoroquinolone core (Q2a) and a nucleaphilic amine linker "X" by following the known literature procedures (such as, Domagala, J. M. et al: *J. Med. Chem.* 1991, 34, 1142-1154; Sanchez, J. P. et al: *J. Med. Chem.* 1988, 31, 983-991) to give quinolone (Q2b). The quinolone (Q2b) may be also commercially available from chemical vendors, like LKT Laboratories, Inc. St. Paul, Minn. 55114, USA. The starting quinolone core (Q2a) or a quinolone pharmacophore fragment is commercially available from Louston International Inc., Linwood, Pa. 19061, USA. The nucleophilic amine linkers can be purchased from chemical venders, like Aldrich Chemical Company, Milwaukee, Wis. 53201, USA or readily prepared starting from commercially available chemicals by following the known literature procedures practiced by someone who is skilled in the art. The hydrazino quinolone (Q2c) can be prepared from the quinolones (Q2b) with a linker "X" already in place, wherein linker "X" has an chemically reactive amino group, like —$NH_2$ or >NH. The hydrazine formation can be done using a two-step procedure, which is nitrosylation of the amine (Q2b) with a nitrosylating agent, like sodium nitrite in aqueous acidic solution, followed by reduction, like reduction with zinc to hydrazine, or a one-step conversion using hydroxylamine O-sulfate in the presence of a base, like NaOH. It will be apparent to one skilled in the art that 3-formyl rifamycin SV (RIF2a) can be replaced by other rifamycin analogs of formula (RIF1) and the quinolone compound (Q2c) can be replaced by other antibiotics derivatives within the gyrase/topoisomerase IV inhibitor family. The reaction is performed in a protic or aprotic solvent. Examples of solvents suitable for this reaction are THF, DMSO, DMF, NMP, ethanol, isopropanol, methanol, dioxane, acetonitrile, acetic acid, water or any combination of the above. The reaction can be performed at a temperature between –20 to 120° C. The preferred temperature is room temperature.

Figure 5:
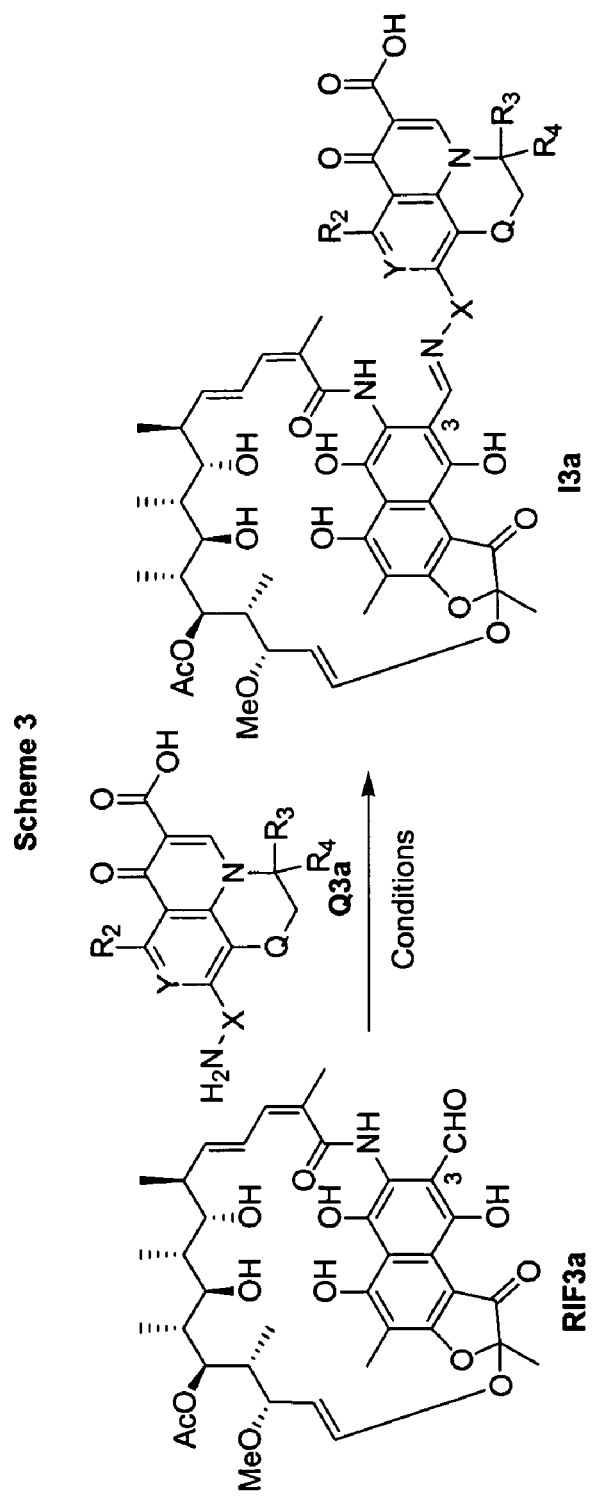
FIG. 5 shows Scheme 3, wherein a rifamycin derivative (RIF3a) reacts with a quinolone compound (Q3a) in a similar fashion as shown in FIG. 4 to produce the inventive compounds Formula I.

Similarly, the current inventive compounds (I3a) can be prepared through a chemical synthetic process by replacing quinolone (Q2c) with a different quinolone (Q3a), as shown in Scheme 3 in FIG. 5.

Specific Compositions

The compounds of the current invention may be better understood with reference to the following examples, which are representative of some of the embodiments of the invention, and are not intended to limit the invention.

All starting material used in these examples are either purchased from commercial sources or prepared according to published procedures. Operations involving moisture and/or oxygen sensitive materials are conducted under an atmosphere of nitrogen. Flash chromatography is performed using silica gel 60 as normal phase adsorbent or C18 silica gel as reverse phase adsorbent. Thin layer chromatography ("TLC") and preparative thin layer chromatography ("PTLC") are performed using pre-coated plates purchased from E. Merck and spots are visualized with ultraviolet light followed by an appropriate staining reagent. Nuclear magnetic resonance ("NMR") spectra are recorded on a Varian 400 MHz magnetic resonance spectrometer. $^1$H NMR chemical shift are given in parts-per million ($\delta$) downfield from TMS using the residual solvent signal ($CHCl_3=\delta$ 7.27, $CH_3OH=\delta$ 3.31) as internal standard. $^1$H NMR information is tabulated in the following format: number of protons, multiplicity (s, singlet; d, doublet; t, triplet; q, quartet; m, multiplet; td, triplet of doublet; dt, doublet of triplet), coupling constant (s) (J) in hertz. The prefix app is occasionally applied in cases where the true signal multiplicity is unresolved and prefix br indicates a broad signal. Electrospray ionization mass spectra are recorded on a Finnegan LCQ advantage spectrometer.

EXAMPLE 4

3-[4-(3-Carboxy-1-cyclopropl-6-fluoro-4-oxo-1,4-dihydroquinolin-7-yl)piperazin-1-yl-aminomethylenyl]rifamycin SV:

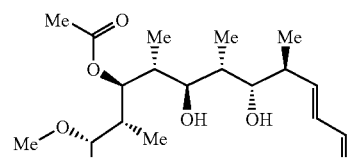

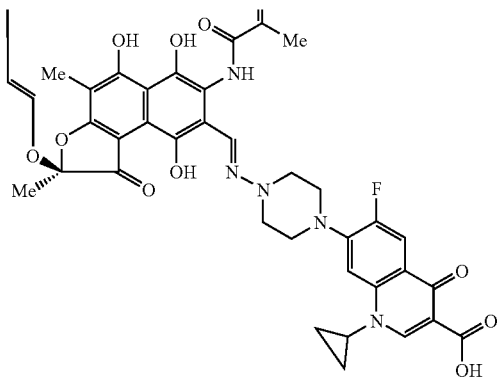

3-[4-(3-Carboxy-1-cyclopropl-6-fluoro-4-oxo-1,4-dihydroquinolin-7-yl)piperazin-1-yl-aminomethylenyl]rifamycin SV was synthesized as follows:

Step 1. 7-(4-Aminopiperazin-1-yl)-1-cyclopropyl-6-fluoro-4-oxo-1,4-dihydroquinoline-3-carboxylic acid: To a stirred suspension of 1-cyclopropyl-6-fluoro-4-oxo-7-piperazin-1-yl-1,4-dihydroquinoline-3-carboxylic acid (ciprofloxacin) (500 mg, 1.5 mmol) in 3 mL acetic acid was added 0.5 mL 3 N HCl solution (1.5 mmol). The solution was cooled to 4° C. and a solution of sodium nitrite (0.13 g, 1.9 mmol) in water (1 mL) was added drop-wise. The suspension was diluted with more solvent to facilitate stirring, and it was allowed to slowly warm up to room temperature and stirring was maintained at this temperature for 5 hours. The suspension was basified by addition of solid sodium acetate. The mixture was cooled in an ice bath and zinc powder (590 mg, 9 mmol) was added in portions. The resultant suspension was allowed to slowly warm up to room temperature and stirring was maintained for 18 hours. The suspension was filtered through a layer of celite and the filtrate containing product was used for step 2 without further purification, ESI MS m/z 347 (M+H$^+$).

Step 2. 3-[4-(3-Carboxy-1-cyclopropyl-6-fluoro-4-oxo-1, 4-dihydroquinolin-7-yl)-piperazin-1-yl-aminomethylenyl] rifamycin SV: At room temperature, to a stirred solution of 3-formylrifamycin SV (100 mg, 0.14 mmol) in ethanol was added the product solution as described in step 1. After the reaction was complete, the resultant solution was partitioned between dichloromethane and 10% citric acid solution. The separated organic layer was washed with 10% citric acid solution (1×), dried over sodium sulfate, concentrated in vacuo to give a red solid, 10% portion of which was purified by preparative thin layer chromatography (10% methanol in dichloromethane in the presence of 1% acetic acid) to give the title compound as an orange solid (4.5 mg, 25%). ESI MS m/z 1054 (M+H$^+$); $^1$H NMR (400 MHz, CD$_3$OD) $\delta$ 8.44 (s, 1H), 7.95 (s, 1H), 7.81 (s, 1H), 7.55 (d, J=13.4 Hz, 1H), 7.47 (d, J=5.4 Hz, 1H), 6.78-6.59 (m, 2H), 6.24 (d, J=13.1 Hz, 1H), 6.07 (dd, J=14.2 Hz and 3.3 Hz, 1H), 5.02 (d, J=11.0 Hz, 1H), 4.96 (dd, J=13.1 Hz and 4.6 Hz, 1H), 3.75 (d, J=9.5 Hz, 1H), 3.63 (br s, 1H), 3.53 (br s, 2H), 3.43 (br d, J=8.6 Hz, 4H), 3.30 (d, J=7.5 Hz, 1H), 3.20 (m, 2H), 3.02 (d, J=9.3 Hz, 1H), 2.96 (s, 3H), 2.32 (br s, 1H), 2.22 (s, 3H), 2.16 (br s, 3H), 1.98 (s, 3H), 1.84 (br s, 3H), 1.58 (br d, J=7.1 Hz, 1H), 1.39 (br d, J=3.0 Hz, 1H), 1.27-1.12 (m, 3H), 0.92 (d, J=6.7 Hz, 3H), 0.91 (d, J=5.5 Hz, 3H), 0.46 (d, J=6.9 Hz, 3H), −0.53 (d, J=5.3 Hz, 3H).

EXAMPLE 5

3-[4-(3-Carboxy-1-cyclopropl-6-fluoro-4-oxo-1,4-dihydroquinolin-7-yl)-piperazin-1-yl-aminomethyl-enyl]rifamycin S:

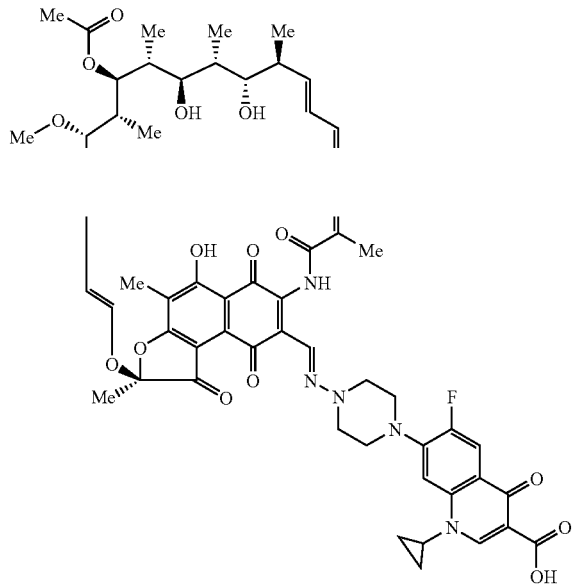

3-[4-(3-Carboxy-1-cyclopropl-6-fluoro-4-oxo-1,4-dihydroquinolin-7-yl)-piperazin-1-yl-aminomethylenyl]rifamycin SV (100 mg), which was prepared as described in Example 4, was dissolved in 5 mL of ethyl acetate. To the resultant solution was added 5 mL PBS buffer, followed by $K_3Fe(CN)_6$ (500 mg, 1.5 mmol). The reaction mixture was allowed to stir at room temperature for one hour, and partitioned between ethyl acetate and water. The separated organic layer was washed with 10% citric acid (2×), dried over sodium sulfate, concentrated in vacuo to afford a dark brown solid, ⅓ portion of which was purified by preparative thin layer chromatography (10% methanol in dichloromethane in the presence of 1% acetic acid) to give the title compound as a purple-black solid (3.4 mg, 16%). ESI MS m/z 1052 (M+H$^+$); $^1$H NMR (400 MHz, CDCl$_3$) δ 12.74 (s, 1H), 10.16 (br s, 1H), 8.80 (s, 1H), 8.08 (d, J=12.4 Hz, 1H), 7.90 (s, 1H), 7.41 (br s, 1H), 7.83 (dd, J=15.9 Hz and 11.5 Hz, 1H), 6.38 (d, J=10.8 Hz, 1H), 6.07 (d, J=12.5 Hz, 1H), 5.98 (dd, J=15.4 Hz and 4.5 Hz, 1H), 5.11 (d, J=9.9 Hz, 1H), 5.06 (dd, J=11.5 Hz and 4.3 Hz, 1H), 4.00 (d, J=3.2 Hz, 1H), 3.85 (d, J=8.3 Hz, 1H), 3.68-3.40 (complex pattern), 3.09 (s, 3H), 3.00 (d, J=9.5 Hz, 1H), 2.40 (br s, 1H), 2.29 (s, 3H), 2.09 (s, 3H), 1,81-1.22 (complex pattern), 1.02 (d, J=7.1 Hz, 3H), 0.85 (d, J=6.9 Hz, 3H), 0.57 (d, J=7.3 Hz, 3H), 0.14 (d, J=6.3 Hz, 3H).

EXAMPLE 6

(R/S)-3-[1-(8-chloro-3-carboxy-1-cyclopropyl-6-fluoro-4-oxo-1,4-dihydroquinolin-7-yl)-pyrrolidin-3-ylhydrazinomethylenyl]rifamycin SV:

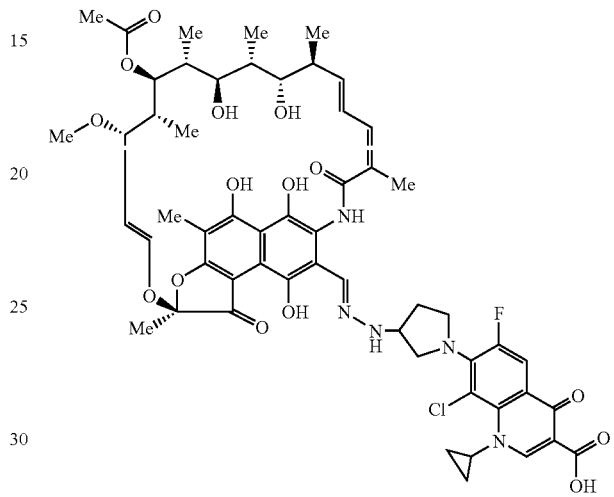

To a stirred solution of (R/S)-7-(3-aminopyrrolidin-1-yl)-8-chloro-1-cyclopropyl-6-fluoro-4-oxo-1,4-dihydroquinoline-3-carboxylic acid hydrochloride (clinafloxacin hydrochloride, 120 mg, 0.30 mmol) in 1 N NaOH (0.8 mL) at 4° C., was added a solution of hydroxylamine-O-sulfonic acid (24 mg) in water (0.2 mL). The resulting mixture was allowed to stir at this temperature for 2 hours. The suspension was acidified with acetic acid to pH 6.0. To this resultant stirred suspension was added 3-formylrifamycin SV (12.5 mg, 0.017 mmol). The mixture was allowed to stir at room temperature for 2 hours and partitioned between dichloromethane and 10% citric acid. The separated organic layer was washed with 10% citric acid (2×), dried over sodium sulfate, concentrated in vacuo to afford an orange solid, which was purified by preparative thin layer chromatography (10% methanol in dichloromethane with presence of 1% acetic acid) to give the title compound as an orange solid (5.3 mg). ESI MS m/z 1088 (M+H$^+$); $^1$H NMR (400 MHz, CDCl$_3$) δ 13.37 (br s, 1H), 13.15 (2s, 1H), 12.72 (2s, 1H), 12.02 (2s, 1H), 8.88 (2s, 1H), 8.45 (2s, 1H), 7.95 (2s, 1H), 6.59 (dd, J=15.4 Hz and 11.2 Hz, 1H), 6.41 (d, J=11.0 Hz, 1H), 6.19 (d, J=12.5 Hz, 1H), 5.98 (m, 1H), 5.62 (br s, 1H), 5.08 (m, 1H), 4.93 (d, J=10.8 Hz), 4.31 (br s, 1H), 4.11 (m, 1H), 3.94 (m, 1H), 3.90 (m, 1H), 3.80 (m, 1H), 3.67 (d, J=5.7 Hz, 1H), 3.60-3.41 (complex m., 4H), 3.04 (s, 3H), 3.02 (m, 1H), 2.40 (m, 1H), 2.20 (2s, 3H), 2.06 (2s, 3H), 1.79 (2s, 3H), 1.73 (m, 3H), 1.56 (m, 1H), 1.40-1.20 (complex m., 4H), 1.01 (2d, 3H), 0.88 (2d, 3H), 0.62 (2d, 3H), −0.30 (2d, 3H).

EXAMPLE 7

(R/S)-3-[4-(3-Carboxy-1-cyclopropyl-6-fluoro-8-methoxy-4-oxo-1,4-dihydroquinolin-7-yl)-2-methyl-piperazin-1-yl-aminomethylenyl]rifamycin SV:

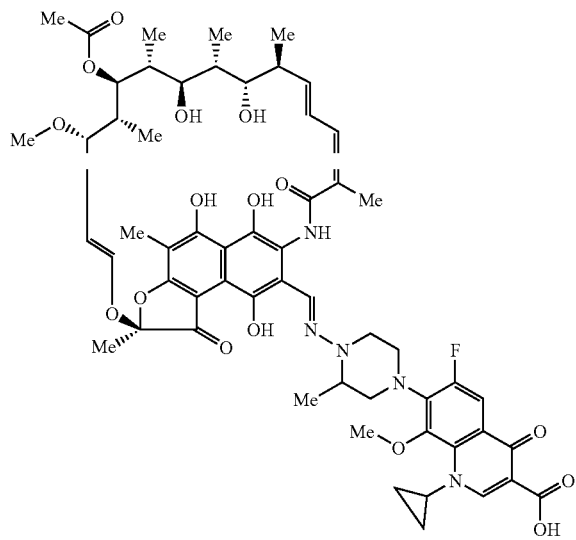

The title compound was prepared by using the same procedure as described for the preparation of Example 4, except (R/S)-1-cyclopropyl-6-fluoro-8-methoxy-7-(3-methylpiperazin-1-yl)-4-oxo-1,4-dihydroquinoline-3-carboxylic acid (gatifloxacin) was used in place of 1-cyclopropyl-6-fluoro-4-oxo-7-(piperazin-1-yl)-1,4-dihydro-quinoline-3-carboxylic acid (ciprofloxacin). The product was isolated as an orange solid. ESI MS m/z 1098 (M+H$^+$); $^1$H NMR (400 MHz, CDCl$_3$) δ 13.37 (s, 1H), 13.21 (s, 1H), 12.06 (2s, 1H), 8.84 (s, 1H), 8.36 (s, 1H), 7.92 (2s, 1H), 6.61 (dd, 1H), 6.43 (m, 1H), 6.20 (2H), 5.97 (m, 1H), 5.11 (dd, J=7.1 Hz and 12.4 Hz, 1H), 4.96 (d, J=10.7 Hz, 1H), 4.02 (m, 1H), 3.86-3.20 (complex pattern), 3.05 (2s, 3H), 3.02 (m, 1H), 2.40 (m, 1H), 2.24 (s, 3H), 2.11 -2.04 (m, 6H), 1.81 (2s, 3H), 1.72 (m, 1H), 1.46-1.21 (complex pattern, 4H), 1.18 (2s, 3H), 1.06-0.96 (m+2d, 2H+3H), 0.90 (2d, 3H), 0.64 (2d, 3H), −0.25 (2d, 3H).

EXAMPLE 8

(R/S)-3-[4-(3-Carboxy-1-ethyl-6,8-difluoro-8-4-oxo-1,4-dihydroquinolin-7-yl)-2-methyl-piperazin-1-yl-aminomethylenyl]rifamycin SV:

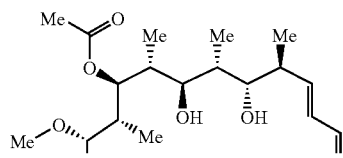

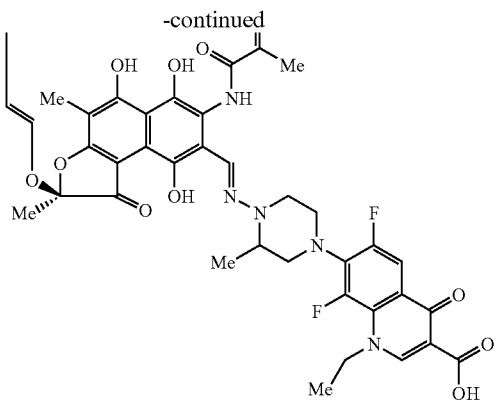

The title compound was prepared by using the same procedure as described for the preparation of Example 4, except (R/S)-1-ethyl-6,8-difluoro-7-(3-methyl-piperazin-1-yl)-4-oxo-1,4-dihydro-quinoline-3-carboxylic acid hydrochloride (lomefloxacin hydrochloride) was used in place of 1-cyclopropyl-6-fluoro-4-oxo-7-piperazin-1-yl-1,4-dihydro-quinoline-3-carboxylic acid (ciprofloxacin). The product was isolated as an orange solid in 55% yield. ESI MS m/z 1074 (M+H$^+$); $^1$H NMR (400 MHz, CDCl$_3$) δ 13.35 (s, 1H), 13.20 (2s, 1H), 12.05 (2s, 1H), 8.61 (s, 1H), 8.32 (s, 1H), 8.98 (m, 1H), 6.60 (dd, J=15.1 Hz and 11.9 Hz, 1H), 6.47 (m, 1H), 6.20 (m, 1H), 5.96 (m, 1H), 5.10 (dd, J=12.5 Hz and 8.0 Hz), 4.95 (d, J=9.8 Hz, 1H), 4.88 (m, 2H), 3.81-3.14 (complex pattern, 8H), 3.04 (s, 3H), 3.03 (m, 1H), 2.39 (m, 1H), 2.23 (s, 3H), 2.07 (m, 6H), 1.80 (2d, 3H), 1.72 (m, 2H), 1.57 (m, 3H), 1.29-1.15 (m, 5H), 1.02 (2d, 3H), 0.89 (2d, 3H), −0.26 (2d, 3H).

EXAMPLE 9

(R/S)-3-[1-[3-Carboxy-1-(2,4-difluoro-phenyl)-6-fluoro-4-oxo-1,4-dihydro-[1,8]naphthyridin-7-yl]-pyrrolidinyl-3-hydrazinomethylenyl]rifamycin SV:

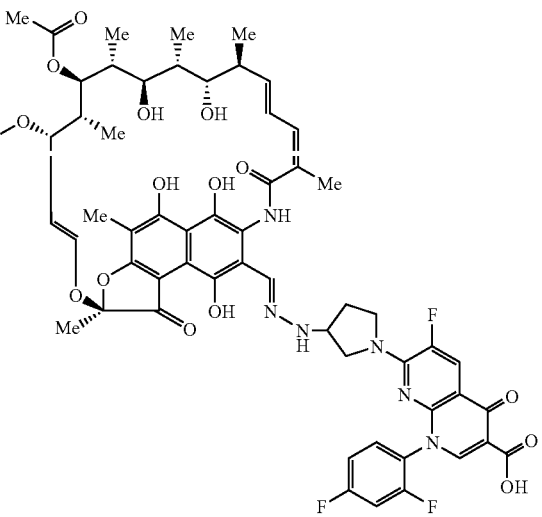

The title compound was prepared by using the same procedure as described for the preparation of Example 6, except (R/S)-7-(3-aminopyrrolidin-1-yl)-1-(2,4-difluoro-phenyl)-6-fluoro-4-oxo-1,4-dihydro-[1,8]naphthyridine-3-carboxylic acid was used in place of (R/S)-7-(3-aminopyr-rolidin-1-yl)-8-chloro-1-cyclopropyl-6-fluoro-4-oxo-1,4-dihydro-quinoline-3-carboxylic acid hydrochloride. The title compound was isolated as an orange solid. ESI MS m/z 1127 (M+H$^+$); $^1$H NMR (400 MHz, CDCl$_3$) δ 13.31 (2s, 1H), 13.15 (s, 1H), 12.46 (2s, 1H), 12.06 (2s, 1H), 8.60 (br s, 1H), 8.45 (bs s, 1H), 8.01 (m, 1H), 7.42 (m, 1H), 7.06 (m, 2H), 6.48 (m, 1H), 6.32 (m, 1H), 6.20 (m, 1H), 5.87 (m, 1H), 5.09 (dd, J=12.5 Hz and 7.3 Hz, 1H), 4.93 (d, J=10.1 Hz, 1H), 4.15-3.17 (complex m., 6H), 3.04 (s, 3H), 3.03 (m, 1H), 2.36 (m, 1H), 2.23 (s, 3H), 2.10-1.93 (m, 6H), 1.78 (br s, 3H), 1.70 (m, 1H), 1.54 (m, 2H), 1.37 (m, 2H), 1.01 (2d, 3H), 0.77 (2d, 3H), 0.62 (2d, 3H), -0.29 (2d, 3H).

EXAMPLE 10

3-[4-[3-Carboxy-1-(2,4-difluoro-phenyl)-6-fluoro-4-oxo-1,4-dihydro-[1,8]naphthyridine-7-yl]-piperazin-1-ylaminomethylenyl]rifamycin S:

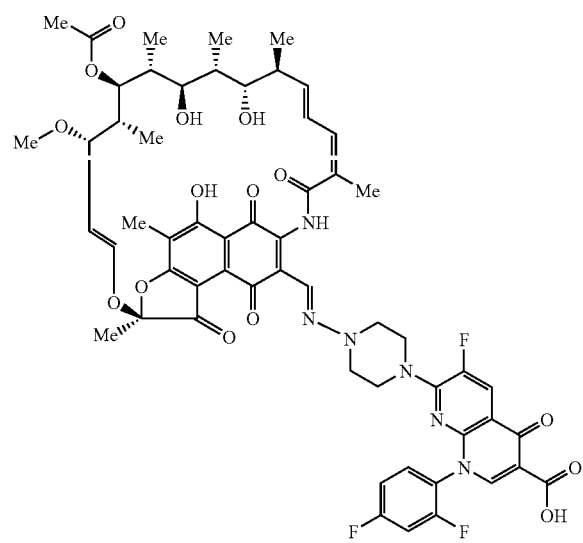

The title compound was prepared by using the same procedure as described for the preparation of Example 5, except 1-(2,4-difluoro-phenyl)-6-fluoro-4-oxo-7-(piperazin-1-yl)-1,4-dihydro-[1,8]naphthyridine-3-carboxylic acid was used in place of 1-cyclopropyl-6-fluoro-4-oxo-7-piperazin-1-yl-1,4-dihydro-quinoline-3-carboxylic acid (ciprofloxa-cin). The title compound was isolated as a purple-black solid. ESI MS m/z 1125 (M+H$^+$); $^1$H NMR (400 MHz, CDCl$_3$) δ 12.72 (s, 1H), 9.79 (s, 1H), 8.69 (s, 1H), 8.16 (d, J=13.5 Hz, 1H), 7.78 (br s, 1H), 7.41 (m, 1H), 7.14 (m, 1H), 6.79 (m, 1H), 6.36 (d, J=11.1 Hz, 1H), 6.06 (d, J=12.6 Hz, 1H), 5.96 (m, 1H), 5.13-4.99 (m, 2H), 3.86-3.69 (complex pattern, 6H), 3.44 (br s, 1H), 3.28 (m, 4H), 3.08 (s, 3H), 2.99 (d, J=10.1 Hz, 1H), 2.38 (br s, 1H), 2.28 (s, 3H), 2.10-1.96 (m, 6H), 1.76 (s, 3H), 1.70 (m, 4H), 1.47 (m, 2H), 1.01 (d, J=7.1 Hz, 3H), 0.78 (m, 3H), 0.54 (d, J=7.2 Hz, 3H), 0.12 (d, J=5.6 Hz, 3H).

EXAMPLE 11

(R/S)-3-[1-(3-Carboxy-1-cyclopropyl-6-fluoro-4-oxo-1,4-dihydroquinolin-7-yl)-pyrrolidin-3-yl-N'-(1-methyl-piperidin-4-yl)-hydrazinomethylenyl]rifamy-cin SV:

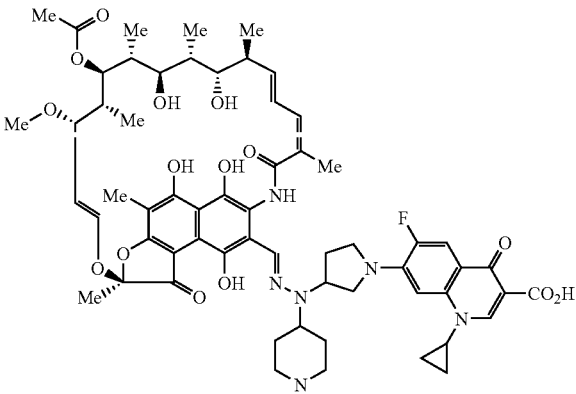

(R/S)-3-[1-(3-Carboxy-1-cyclopropyl-6-fluoro-4-oxo-1,4-dihydroquinolin-7-yl)-pyrrolidin-3-yl-N'-(1-methyl-piperidin-4-yl)-hydrazinomethylenyl]rifamycin SV can be prepared as follows:

Step 1. 8-Chloro-1-cyclopropyl-6-fluoro-7-[3-(1-methyl-piperidin-4-ylamino)-pyrrolidin-1-yl]-4-oxo-1,4-dihydro-quinoline-3-carboxylic acid: To a stirred suspension of (R/S)-7-(3-aminopyrrolidin-1-yl)-8-chloro-1-cyclopropyl-6-fluoro-4-oxo-1,4-dihydroquinoline-3-carboxylic acid hydrochloride (clinafloxacin hydrochloride) (70 mg, 0.19 mmol) in dichloromethane at room temperature, was added sodium acetate (24 mg), acetic acid (100 μL), and N-methyl-4-piperidone (30 μL). This was allowed to stir at room temperature for 30 min, and sodium triacetoxyborohydride (50 mg) was added. The resultant mixture was allowed to stir for 18 h. The solvent was evaporated in vacuo, and the crude product was used directly for next step.

Step 2. (R/S)-3-[1-(3-Carboxy-1-cyclopropyl-6-fluoro-4-oxo-1,4-dihydroquinolin-7-yl)-pyrrolidin-3-yl-N'-(1-methyl-piperidin-4-yl)-hydrazinomethylenyl]rifamycin SV: The product obtained as described in step 1 was dissolved in acetic acid (2 mL). To this, was added 3 N HCl (50 μL), followed by a solution of sodium nitrite (22 mg) in water (0.5 mL). The resultant mixture was allowed to stir at room temperature for 2 h. The solvent was evaporated in vacuo, and residue was dissolved in 5% Na$_2$HPO$_4$ solution. The aqueous solution was extracted with dichloromethane in the presence of 20% IPA (2×). The combined organic extracts were dried over sodium sulfate, and concentrated in vacuo to give a white solid. This was dissolved in 50% acetic acid in water (2 mL). To the resultant solution was added zinc powder (50 mg, 0.76 mmol), and was allowed to stir at room temperature for 10 min, and 50° C. for 30 min. The reaction mixture was cooled, and zinc was filtered. The filtrate was diluted with 4 mL of ethanol. To the resultant solution was added sodium acetate to pH 5, followed by 3-formylrifamy-cin (50 mg), and the solution was allowed to stir at room temperature for 40 min. The mixture was partitioned between dichloromethane and 5% Na$_2$HPO$_4$ solution. The organic layer was separated, dried over sodium sulfate, concentrated in vacuo, and the residue was purified by PTLC (CH$_2$Cl$_2$/MeOH/HOAc/Et$_3$N; 90:10:1:1) to yield the title product as a brown solid (10 mg, 13%). ESI MS m/z 1151 (M+H$^+$).

EXAMPLE 12

(R/S)-3-[4-(3-Carboxy-1-cyclopropyl-6-fluoro-8-methoxy-4-oxo-1,4-dihydroquinolin-7-yl)-2-methylpiperazin-1-yl-aminomethylenyl]rifamycin S:

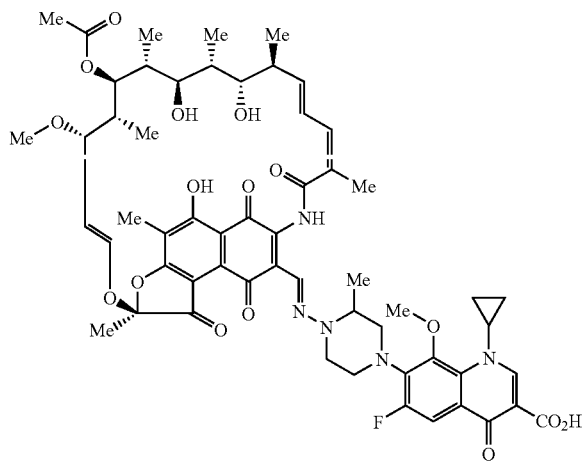

The title compound was prepared by using a similar procedure as described for the preparation of Example 5, except (R/S)-1-cyclopropyl-6-fluoro-8-methoxy-7-(3-methylpiperazin-1-yl)-4-oxo-1,4-dihydroquinoline-3-carboxylic acid (gatifloxacin) was used in place of 1-cyclopropyl-6-fluoro-4-oxo-7-(piperazin-1-yl)-1,4-dihydro-quinoline-3-carboxylic acid (ciprofloxacin). The product was isolated as black solid. ESI MS m/z 1096 (M+H$^+$).

EXAMPLE 13

3-[6-(3-Carboxy-1-cyclopropyl-6-fluoro-8-methoxy-4-oxo-1,4-dihydroquinolin-7-yl)-octahydropyrrolo[3,4-b]pyridin-1-yl-aminomethylenyl]rifamycin S:

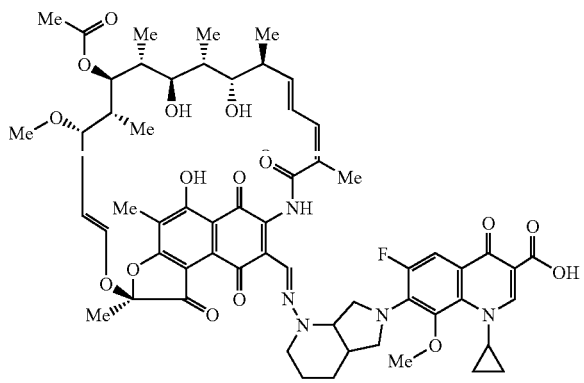

The title compound was prepared by using a similar procedure as described for the preparation of Example 5, except 1-cyclopropyl-6-fluoro-8-methoxy-7-(octahydropyrrolo[3,4-b]pyridin-6-yl)-4-oxo-1,4-dihydro-quinoline-3-carboxylic acid (moxifloxacin) was used in place of 1-cyclopropyl-6-fluoro-4-oxo-7-piperazin-1-yl-1,4-dihydro-quinoline-3-carboxylic acid (ciprofloxacin). The product was isolated as a purple black solid in 46% yield. ESI MS m/z 1122 (M+H$^+$); $^1$H NMR (400 MHz, CDCl$_3$) δ 12.78 (s, 1H), 8.77 (s, 1H), 7.82-7.77 (m, 2H), 6.75 (m, 1H), 6.30 (d, J=10.9 Hz, 1H), 6.03 (d, J=10.9 Hz, 1H), 5.95 (d, J=15.6 Hz, 1H), 5.08 (d, J=9.51 Hz, 1H), 5.02 (dd, J=11.9 Hz and 4.5 Hz, 1H), 4.18 (q, J=6.2 Hz, 1H), 3.97 (m, 2H), 3.89-3.76 (complex pattern, 3H), 3.60 (d J=7.5 Hz, 1H), 3.56 (s, 3H), 3.50-3.19 (complex pattern), 3.06 (s, 3H), 3.00 (d, J=9.6 Hz, 1H), 2.5 (m, 1H), 2.40 (m, 1H), 2.25 (s, 3H), 2.05 (s, 3H), 1.86-1.10 (complex pattren), 1.01 (d, J=6.2 Hz, 3H), 0.83 (d, J=7.0 Hz, 3H), 0.55 (d, J=6.9 Hz, 3H), 0.12 (br s, 3H).

EXAMPLE 14

3-[4-[3-Carboxy-1-(2,4-difluoro-phenyl)-6-fluoro-4-oxo-1,4-dihydro-[1,8]naphthyridine-7-yl]-piperazin-1-ylaminomethylenyl]rifamycin SV:

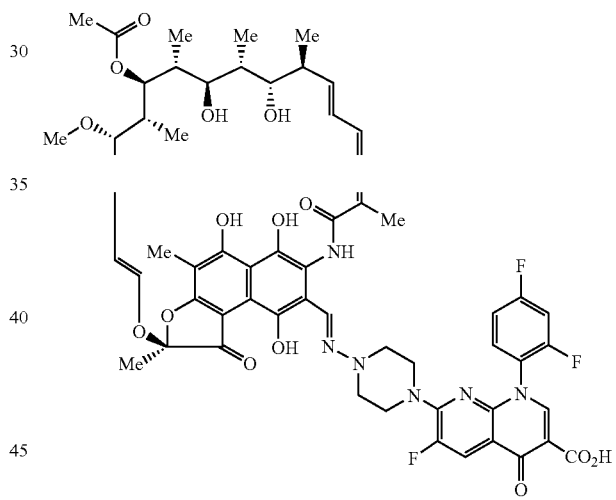

The title compound was prepared by using the same procedure as described for the preparation of Example 4, except 1-(2,4-difluoro-phenyl)-6-fluoro-7-piperazin-1-yl-4-oxo-1,4-dihydro-[1,8]naphthyridine-3-carboxylic acid was used in place of 1-cyclopropyl-6-fluoro-4-oxo-7-piperazin-1-yl-1,4-dihydroquinoline-3-carboxylic acid (ciprofloxacin). The title compound was isolated as a purple-black solid. ESI MS m/z 1095 (M+-MeOH); $^1$H NMR (400 MHz, CDCl$_3$) δ 13.37 (s, 1H), 13.19 (s, 1H), 12.91 (s, 1H), 12.14 (s, 1H), 8.69 (s, 1H), 8.36 (d, J=5.47 Hz, 1H), 8.18 (d, J=12.52 Hz, 2H), 7.41 (m, 1H), 7.13 (m, 1H), 6.57 (m, 1H), 6.40 (d, J=11.73 Hz, 1H), 6.19 (d, J=12.52 Hz, 1H), 5.92 (m, 1H), 5.30 (s, 1H), 5.10 (dd, J$_1$=6.26 Hz, J$_2$=12.52 Hz, 1H), 4.94 (d, J=10.95 Hz, 1H) 3.76 (m, 5H), 3.66 (m, 2H), 3.50 (m, 1H), 3.16 (m, 4H), 3.03 (s, 3H), 3.00 (m, 1H), 2.23 (s, 3H), 2.09 (m, 4H), 2.07 (s, 3H), 1.80 (s, 3H), 1.66-1.50 (m, 5H), 1.00 (d, J=6.26 Hz, 3H), 0.79 (dd, J$_1$=7.04 Hz, J$_2$=14.08 Hz, 3H) 0.59 (d, J=7.04 Hz, 3H), −0.30 (d, J=5.47 Hz, 3H).

EXAMPLE 15

(R/S)-3-[1-(3-Carboxy-1-cyclopropyl-6-fluoro-4-oxo-1,4-dihydroquinolin-7-yl)-pyrrolidin-3-yl-N'-methylhydrazinomethylenyl]rifamycin SV:

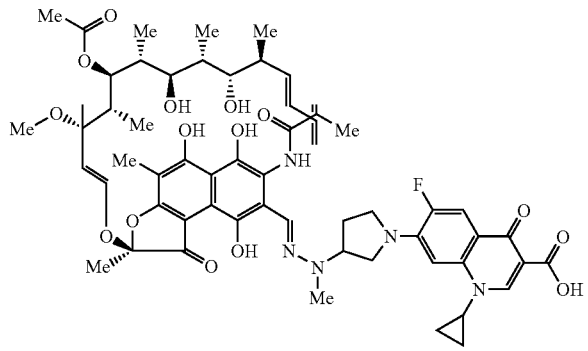

(R/S)-3-[1-(3-Carboxy-1-cyclopropyl-6-fluoro-4-oxo-1,4-dihydroquinolin-7-yl)-pyrrolidin-3-yl-N'-methylhydrazinomethylenyl]rifamycin SV can be prepared as follows:

Step 1. (R/S)-7-[3-(tert-Butoxycarbonyl-methyl-amino)-pyrrolidin-1-yl]-1-cyclopropyl-6-fluoro-4-oxo-1,4-dihydro-quinoline-3-carboxylic acid: To a stirred suspension of 7-chloro-1-cyclopropyl-6-fluoro-4-oxo-dihydroquinoline-3-carboxylic acid (700 mg, 2.5 mmol) in 5 mL pyridine was added 3-(tert-butoxycarbonylamino)pyrrolidine (1.00 g, 5.0 mmol) and refluxed at 100° C. for 24 hours. The reaction was cooled to room temperature, MeOH (30 ml) was added and after 20 minutes the title compound precipitated as white solid in a 57% yield. ESI MS m/z 446 [M+H]$^+$; $^1$H NMR (400 MHz, DMSO-d$_6$) δ 9.08 (s, 1H), 8.32 (d, J=14.08 Hz, 1H), 7.60 (d, J=7.82 Hz, 1H), 4.26 (m, 3H), 4.17-4.04 (m, 2H), 3.83 (m, 2H), 3.31 (s, 3H), 2.66 (m, 1H) 1.94 (s, 9H), 1.81 (m, 2H), 1.65 (m, 2H).

Step 2. (R/S)-1-Cyclopropyl-6-fluoro-7-(3-methylamino-pyrrolidin-1-yl)-4-oxo-1,4-dihydro-quinoline-3-carboxylic acid: The product from step 1 was stirred in a solution of 25% trifluoroacetic acid in dichloromethane for one hour. The solvent was removed in vacuo to give the title product which was used without further purification. ESI MS m/z: [M+H]+=346; $^1$H NMR (400 MHz, DMSO) δ 8.91 (br s, 1H), 8.57 (s, 1H), 7.82 (d, J=14.08 Hz, 1H), 7.09 (d, J=7.82 Hz, 1H), 3.92 (m, 2H), 3.75 (m, 3H), 3.63 (m, 1H), 2.66 (m, 3H), 2.36 (m, 1H), 2.22 (m, 1H), 1.30 (m, 2H), 1.15 (m, 2H).

Step 3. (R/S)-1-Cyclopropyl-6-fluoro-7-[3-(N-methylhydrazino)-pyrrolidin-1-yl]-4-oxo-1,4-dihydro-quinoline-3-carboxylic acid: To a stirred suspension of 1-cyclopropyl-6-fluoro-7-(3-methylaminopyrrolidin-1-yl)-4-oxo-1,4-dihydro-quinoline-3-carboxylic acid (256 mg, 0.74 mmol) in 1 mL acetic acid was added 3 N HCl solution (0.270 mL, 1.5 mmol). The solution was cooled to 4° C. and a solution of sodium nitrite (0.221 g, 3.20 mmol) in water (3 mL) was added dropwise. The suspension was allowed to slowly warm up to room temperature and stirring was maintained at this temperature for 2 hours. The suspension was poured into 0.5 N HCl (50 mL) and extracted with three 50 mL portions of dichloromethane to give the pure nitroso intermediate. The intermediate was then taken up in 5 mL acetic acid and 5 mL water and zinc powder was added (197 mgs, 3.0 mmol) and stirred for 3 hours. The suspension was filtered through a layer of celite, washing with MeOH and the filtrate containing product was used for step 4 without further purification. ESI MS m/z 361 (M+H$^+$).

Step 4. (R/S)-3-[1-(3-Carboxy-1-cyclopropyl-6-fluoro-4-oxo-1,4-dihydroquinolin-7-yl)-pyrrolidin-3-yl-N'-methylhydrazinomethylenyl]rifamycin SV: At room temperature, to a stirred solution of 3-formylrifamycin SV (169 mg, 0.23 mmol) in methanol was added the product solution as described in step 3. After the reaction was complete, the resultant solution was partitioned between dichloromethane and 5% citric acid solution. The separated organic layer was washed with 5% citric acid solution (1×), dried over sodium sulfate, concentrated in vacuo to give a red solid, which was purified by preparative thin layer chromatography (10% methanol in dichloromethane in the presence of 1% acetic acid) to give the title compound as an red solid (12.3 mg, 1.5% yield). ESI MS m/z 1068 (M+H)$^+$; $^1$H NMR (400 MHz, CDCl$_3$) δ 12.80 (s, 1H), 12.31 (s, 1H), 8.80 (d, J=7.82 Hz, 1H), 8.32 (s, 1H), 8.08 (dd, J$_1$=7.82, J$_2$=14.08 Hz, 1H), 7.11 (d, J=7.04 Hz, 1H), 6.78-6.56 (m, 2H), 6.47 (d, J=12.52 Hz, 1H), 6.24 (m, 1H), 5.37 (m, 1H) 5.20 (d, J=10.95 Hz, 1H), 4.53 (m, 2H), 4.20-3.75 (m, 10H), 3.31 (s, 3H), 3.32 (m, 2H), 3.21 (s, 3H) 2.66 (m, 1H), 2.43 (s, 3H), 2.41 (m, 3H), 2.33 (m, 6H), 2.28 (m, 1H), 2.07 (s, 3H), 1.98 (m, 1H), 1.83 (m, 1H), 1.67 (m, 1H), 1.61 (m, 1H), 1.46 (m, 1H), 1.28 (d, J=6.26 Hz, 3H), 1.09 (d, J=7.04 Hz, 3H) 0.92 (m, 3H), 0.01 (apt. t, 3H).

EXAMPLE 16

(R/S)-3-[(4-{1-[1-(3-Carboxy-1-cyclopropyl-6-fluoro-8-methoxy-4-oxo-1,4-dihydro-quinoline-7-yl)-pyrrolidin-3-yl-cyclopropyl]-methyl)-amino}-piperidin-1-ylimino)-methyl]-rifamycin S:

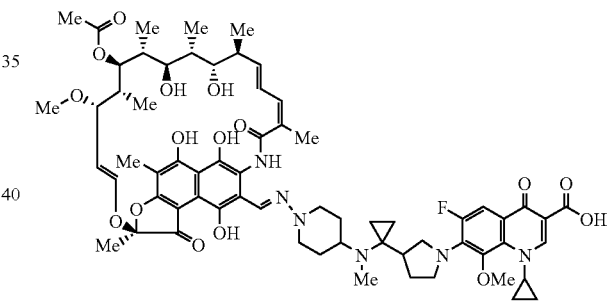

Step 1. 4-Methylamino-piperidine-1-carboxylic acid tert-butyl ester: To a stirred solution of 4-oxo-piperidine-1-carboxylic acid tert-butyl ester (2.0 g, 10 mmol) and methyl amine (2.0 M in MeOH, 20 mL, 40 mmol) in methanol (7.0 mL) was added MgSO$_4$ (1.0 g) and stirred at room temperature for 2 h. NaBH$_3$CN (304 mg, 4.8 mmol) was added in two portions. The resulting solution was stirred at room temperature for 30 minutes and then partitioned between ethyl acetate and water. The separated organic layer was washed with brine, dried over sodium sulfate and concentrated in vacuo to give product as colorless oil (1.6 g).

Step 2. 4-(Acryloyl-ethyl-amino)-piperidine-1-carboxylic acid tert-butyl ester: To a solution of 4-methylamino-piperidine-1-carboxylic acid tert-butyl ester (1.6 g, 7.5 mmol) in dichloromethane (15 mL) was added NaHCO$_3$ (1.5 g, 17.9 mmol), followed by acryloyl chloride (0.66 mL, 8.1 mmol) at 0° C. After stirring at room temperature for 30 min, the solution was partitioned between ethyl acetate and water. The separated organic layer was washed with brine, dried over sodium sulfate and concentrated in vacuo to give product as colorless oil (2.0 g).

Step 3. 4-[(1-Benzyl-pyrrolidine-3-carbonyl)-methyl-amino]-piperidine-1-carboxylic acid tert-butyl ester: To a solution of 4-(acryloyl-ethyl-amino)-piperidine-1-carboxylic acid tert-butyl ester (2.0 g, 7.5 mmol) and N-(methoxymethyl)-N-(trimethylsilylmethyl)benzylamine (1.92 mL, 7.5 mmol) in dichloromethane (20 mL) was added trifluoroacetic acid (50 µL, 0.44 mmol) at room temperature. The resulting solution was stirred overnight and concentrated in vacuo to give colorless oil, which was purified by flash chromatography on silica gel with gradient elution of 2-10% methanol in dichloromethane to give product as oil (2.0 g, 66%). ESI MS m/z 402.3 (M+H$^+$).

Step 4: 4-{[1-(1-Benzyl-pyrrolidin-3-yl)-cyclopropyl]-methyl-amino}-piperidine-1-carboxylic acid tert-butyl ester: A stirred solution of ethylmagnesium bromide (3.0 M in ethyl ether, 2.1 mL, 6.3 mmol) in THF (17.0 mL) was cooled to −78° C. To this solution was added a solution of titanium (IV) isopropoxide (0.76 mL, 2.6 mmol) in THF (1.7 mL) dropwise with the temperature below −70° C. After stiring for three minutes, the solution of 4-[(1-benzyl-pyrrolidine-3-carbonyl)-methyl-amino]-piperidine-1-carboxylic acid tert-butyl ester (1.0 g, 2.5 mmol) in THF (1.7 mL) was added. The resulting solution was slowly warmed to room temperature, heated at reflux for one hour and then cooled to 8° C. Ethylmagnesium bromide (3.0 M in ethyl ether, 1.8 mL, 5.4 mmol) was added followed by a solution of titanium (IV) isopropoxide (0.66 mL, 2.2 mmol) in THF (1.0 mL) rapidly. The reaction mixture was stirred at room temperature for one hour and partitioned between ethyl acetate and water. The separated organic layer was washed with brine, dried over sodium sulfate and concentrated in vacuo. The residue was purified by preparative thin layer chromatography (60% ethyl acetate in hexane with 0.5% triethylamine) to give pale yellow oil (390 mg, 38%). ESI MS m/z 414.3 (M+H$^+$).

Step 5. 4-[Methyl-(1-pyrrolidin-3-yl-cyclopropyl)-amino]-piperidine-1-carboxylic acid tert-butyl ester: To a solution of 4-{[1-(1-benzyl-pyrrolidin-3-yl)-cyclopropyl]-methyl-amino}-piperidine-1-carboxylic acid tert-butyl ester (390 mg, 0.39 mmol) in acetic acid (12.0 mL) was added 30% Pd/C (150 mg). The resulting mixture was hydrogenated using a parr shaker under 50 Psi for 25 hours. The catalyst was filtered and solvent removed, residue was basified with 20% NaOH solution and extracted with ethyl acetate. The combined organic extracts were dried, concentrated in vacuo to a pale yellow oil (~300 mg) which could be used in next step directly. ESI MS m/z 324.3 (M+H$^+$).

Step 6: 7-(3-{1-[(1-tert-Butoxycarbonyl-piperidin-4-yl)-methyl-amino]-cyclopropyl}-pyrrolidin-1-yl)-1-cyclopropyl-6-fluoro-8-methoxy-4-oxo-1,4-dihydro-quinoline-3-carboxylic acid: A solution of 4-[methyl-(1-pyrrolidin-3-yl-cyclopropyl)-amino]-piperidine-1-carboxylic acid tert-butyl ester (100 mg, 0.31 mmol) in acetonitrile (30.0 mL) was added 1-cyclopropyl-6,7-difluoro-8-methoxy-4-oxo-1,4-dihydro-quinoline-3-carboxylic acid (98 mg, 0.33 mmol) and DBU (0.23 mL, 1.53 mmol). The suspension was heated to 75° C. overnight. The reaction mixture was partitioned between ethyl acetate and 5% citric acid. The separated organic layer was washed with brine, dried over sodium sulfate and concentrated in vacuo. The residue was purified by preparative thin layer chromatography (10% methanol in dichloromethane) to give the title compound as a yellow solid (102 mg, 62%). ESI MS m/z 599.3 (M+H$^+$).

Step 7: 1-Cyclopropyl-6-fluoro-8-methoxy-7-{3-[1-(methyl-piperidin-4-yl-amino)-cyclopropyl]-pyrrolidin-1-yl}-4-oxo-1,4-dihydro-quinoline-3-carboxylic acid: To a stirred solution of 7-(3-{1-[(1-tert-butoxycarbonyl-piperidin-4-yl)-methyl-amino]-cyclopropyl}-pyrrolidin-1-yl)-1-cyclopropyl-6-fluoro-8-methoxy-4-oxo-1,4-dihydro-quinoline-3-carboxylic acid in dichloroethane (2.0 mL) was added trifluoroacetic acid (1.0 mL, ~13 mmol) at 0° C. during a period of 5-6 minutes. The resulting solution was stirred at room temperature for one hour. The solvent was removed to yield yellow oil, which was partitioned between CH$_2$Cl$_2$ and sat. aq NaHCO$_3$. The separated aqueous phase was extracted with CH$_2$Cl$_2$. The combined organic layer was washed with brine, dried over sodium sulfate and concentrated in vacuo. The product was isolated as a yellow solid (85 mg, 100%). ESI MS m/z 499.4 (M+H$^+$).

Step 8: (R/S)-3-[(4-{1-[1-(3-Carboxy-1-cyclopropyl-6-fluoro-8-methoxy-4-oxo-1,4-dihydro-quinoline-7-yl)-pyrrolidin-3-yl-cyclopropyl]-methyl)-amino}-piperidin-1-ylimino)-methyl]-rifamycin S: A solution of hydroxylamine-O-sulfonic acid (130 mg, 1.14 mmol) in H$_2$O (0.9 mL) was added dropwise to a solution of 1-cyclopropyl-6-fluoro-8-methoxy-7-{3-[1-(methyl-piperidin-4-yl-amino)-cyclopropyl]-pyrrolidin-1-yl}-4-oxo-1,4-dihydro-quinoline-3-carboxylic acid (475 mg, 0.95 mmol) in 1 N aq NaOH (5.5 mL) at 0° C. The resulted solution was stirred at same temperature for about one hour. To the reaction solution was added acetic acid (1.0 mL), methanol (10.0 mL), followed by a solution of 3-formyl rifamycin (480 mg, 0.66 mmol) in methanol. The resulted suspension was stirred at room temperature for 3 hours. The orange solid was filtered and washed successfully with water. The solid was further triturated with 70% MeOH in H$_2$O (10 mL×2) to give an orange solid (590 mg). ESI MS m/z 1189.6 (M-MeO)$^+$, 1221.6 (M+H)$^+$. $^1$H NMR (400 MHz, CDCl$_3$) δ (~1:1 two diastereomers) 14.20 (s, 1H), 13.52 (s, 1H), 13.26, 13.25 (two siglets, 1H), 13.22 (s, 1H), 11.98, 11.97 (two siglets, 1H), 8.73 (s 1H), 8.22 (s, 1H), 7.75 (d, J=13.6 Hz, 1H), 6.54 (dd, J=11.2, 15.2 Hz, 1H), 6.39-6.36 (m, 1H), 6.19 (d, J=12.8 Hz, 1H), 5.94-5.87 (m, 1H), 5.06 (dd, J=6.0, 12.8 Hz, 1H), 4.89 (d, J=10.8 Hz, 1H), 3.98-3.93 (m, 1H), 3.80-3.75 (m, 1H), 3.72 (d, J=9.2 Hz, 1H), 3.64 (d, J=12.0 Hz, 1H), 3.60-3.51 (m, 2H), 3.50 (s, 2H), 3.50-3.40 (m, ~5H), 3.00 (s, 3H), 3.02-2.96 (m, 1H), 2.67-2.51 (m, 4H), 2.38 (s, 3H), 2.37-2.31 (m, 1H), 2.03 (s, 3H), 2.02 (app s, 6H), 1.95-1.88 (m, 2H), 1.76 (s, 3H), 1.60-1.20 (m, ~8H), 1.09-1.02 (m, 2H), 0.98-0.95 (m, 3H), 0.82 (d, J=6.4 Hz, 3H), 0.81-0.64 (m, 6H), 0.56 (d, J=6.4 Hz, 3H), −0.35 (d, J=6.8 Hz, 3H).

EXAMPLE 17

(R/S)-3-{[4-({1-[1-(3-Carboxy-8-chloro-1-cyclopropyl-6-fluoro-4-oxo-1,4-dihydro-quinolin-7-yl)-pyrrolidin-3-yl]-cyclopropyl}-methyl-amino)-piperidin-1-ylimino]-methyl}-rifamycin SV:

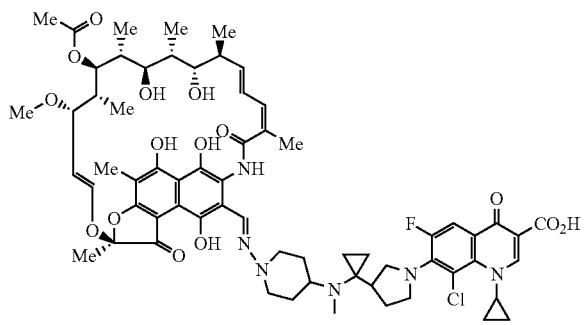

The title compound was prepared by using the same procedure as described for the preparation of Example 16 except 8-chloro-1-cyclopropyl-6,7-difluoro-4-oxo-1,4-dihydro-quinoline-3-carboxylic acid was used in place of 1-cyclopropyl-6,7-difluoro-8-methoxy-4-oxo-1,4-dihydro-quinoline-3-carboxylic acid. The product was isolated as an orange solid in 14% yield. ESI MS m/z 1193 (M+H$^+$); $^1$H NMR (400 MHz, CDCl$_3$) δ 14.66 (s, 1H), 13.57 (s, 1H), 13.31 (s, 1H), 13.26 (s, 1H), 12.01 (s, 1H), 8.86 (s, 1H), 7.93 (d, J=13.6 Hz, 1H), 6.61-6.54 (m, 1H), 6.41 (d, J=10.0 Hz, 1H), 6.23 (d, 12.8 Hz, 1H), 5.98-5.92 (m, 1H), 5.10 (dd, J=12.4 Hz and 6.8 Hz, 1H), 4.93 (d, J=10.4 Hz, 1H), 4.30 (m, 1H), 4.00 (m, 1H), 3.77 (d, J=9.6 Hz, 1H), 3.70-3.39 (m, 8H), 3.04 (s, 3H), 3.04-3.02 (m, 1H), 2.72-2.53 (m, 4H), 2.42 (s, 3H), 2.23 (s, 3H), 2.08 (s, 3H), 2.067 (s, 3H), 2.066 (s, 3H), 1.97-1.13 (m, 9H), 1.80 (s, 3H), 1.01 (d, J=7.2 Hz, 3H), 0.86 (d, J=7.2 Hz, 3H), 0.61 (d, J=6.8 Hz, 3H), 1.02-0.60 (m, 4H), 0.31 (d, J=7.2 Hz, 3H).

EXAMPLE 18

3-[4-(3-Carboxy-1-ethyl-6-fluoro-4-oxo-1,4-dihydroquinolin-7-yl)-piperazin-1-yl-aminomethylenyl]-rifamycin SV:

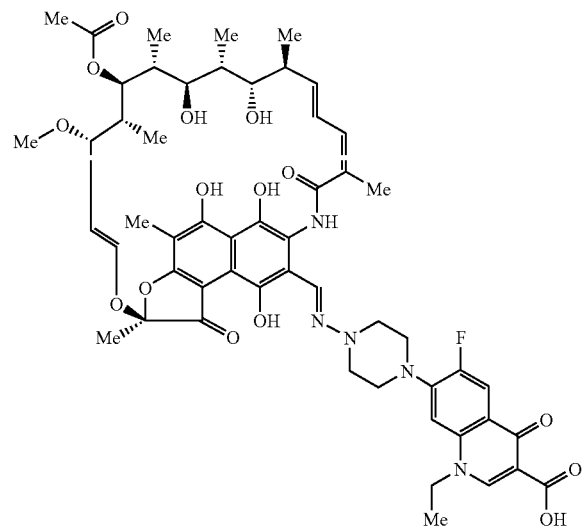

The title compound was prepared by using the same procedure as described for the preparation of Example 4 except 1-ethyl-6-fluoro-4-oxo-7-piperazin-1-yl-1,4-dihydro-quinoline-3-carboxylic acid was used instead of 1-cyclopropyl-6-fluoro-4-oxo-7-piperazin-1-yl-1,4-dihydroquinoline-3-carboxylic acid (ciprofloxacin). The product was isolated as an orange solid. MS: (M+H$^+$) 1042; $^1$H NMR (400 MHz, CDCl$_3$) δ 13.19 (s, 1H), 13.01 (s, 1 H), 8.65 (s, 1H), 8.39 (s, 1H), 8.06 (d, J=12.6 Hz, 1H), 6.84 (m, 1H), 6.61 (dd, J=15.4 and 11.5 Hz, 1H), 6.41 (d, J=11.0 Hz, 1H), 6.19 (d, J=12.3 Hz, 1H), 5.97 (dd, J=15.5 and 5.6 Hz, 1H), 5.10 (dd, J=12.4 and 6.2 Hz, 1H), 4.94 (d, J=10.5 Hz, 1H), 4.32 (m, 1 H), 3.51-3.24 (complex pattern), 3.02 (s, 3H), 2.99 (m, 1H), 2.89 (m, 1H), 2.39 (m, 1H), 2.21 (s, 1H), 2.08 (s, 1H), 2.04 (s, 1H), 1.79 (s, 1H), 1.69 (m, 1H), 1.54 (m, 1H), 1.35 (m, 1H), 1H), 1.00 (d, J=6.9 Hz, 3H), 0.88 (d, J=7.1 Hz, 3H), 0.60 (d, J=6.4 Hz, 3H), −0.29 (d, J=7.1 Hz, 3H).

EXAMPLE 19

3-[4-(3-Carboxy-1-ethyl-6-fluoro-4-oxo-1,4-dihydro-[1,8]naphthyridine-7-yl)-piperazin-1-yl-aminomethylenyl]-rifamycin SV:

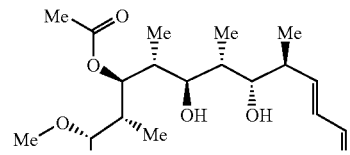

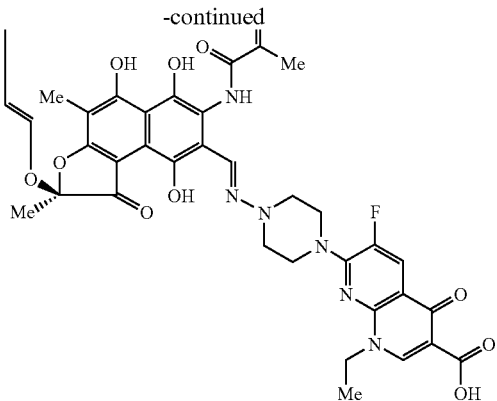

The title compound was prepared by using the same procedure as described for the preparation of Example 4 except 1-ethyl-6-fluoro-4-oxo-7-piperazin-1-yl-1,4-dihydro-[1,8]naphthyridine-3-carboxylic acid was used instead of 1-cyclopropyl-6-fluoro-4-oxo-7-piperazin-1-yl-1,4-dihydro-quinoline-3-carboxylic acid (ciprofloxacin). The product was isolated as an orange solid 4. MS: (M+H$^+$) 1043; $^1$H NMR (400 MHz, CDCl$_3$) δ 13.15 (s, 1H), 12.96 (s, 1H), 12.07 (s, 1H), 8.66 (s, 1H), 8.36 (s, 1H), 8.11 (d, J=12.5 Hz, 1H), 6.60 (dd, J=15.5 and 11.6 Hz, 1H), 6.42 (d, J=10.9 Hz, 1H), 6.19 (d, J=11.7 Hz, 1H), 5.79 (dd, J=15.0 and 4.5 Hz, 1H), 5.09 (dd, J=12.5 and 7.3 Hz, 1H), 4.92 (d, J=9.9 Hz, 1H), 4.41 (m, 2H), 4.00 (m, 4H), 3.76 (d, J=9.5 Hz, 1H), 3.46 (d, J=5.5 Hz, 1H), 3.32 (m, 4H), 3.01 (s, 1H), 2.99 (m, 1H), 2.38 (m, 1H), 2.20 (s, 3H), 2.08 (s, 3H), 2.04 (s, 3H), 1.78 (s, 1H), 1.67 (m, 1H), 1.51 (tr, J=6.9 Hz, 3H), 1.32 (m, 1H), 0.99 (d, J=6.2 Hz, 3H), 0.84 (d, J=7.1 Hz, 3H), 0.59 (d, J=7.1 Hz, 3H), −0.32 (d, J=7.1 Hz, 1H).

EXAMPLE 20

3-[4-(3-Carboxy-1-cyclopropyl-6-fluoro-8-methoxy-4-oxo-1,4-dihydroquinolin-7-yl)-piperazin-1-yl-aminomethylenyl]-rifamycin SV:

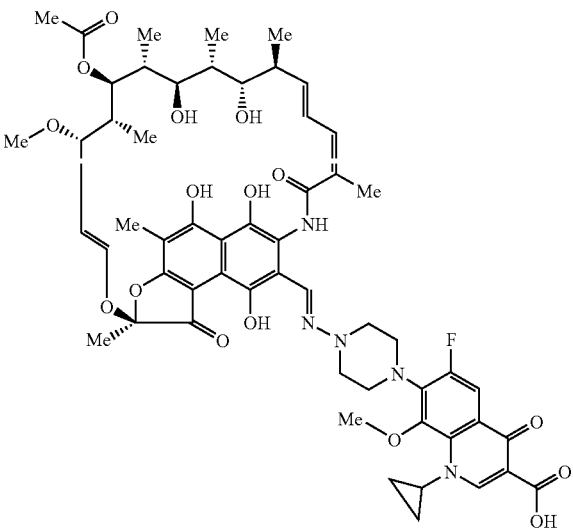

The title compound was prepared by using the same procedure as described for the preparation of Example 4 except 1-cyclopropyl-6-fluoro-8-methoxy-4-oxo-7-piperazin-1-yl-1,4-dihydro-quinoline-3-carboxylic acid was used instead of 1-cyclopropyl-6-fluoro-4-oxo-7-piperazin-1-yl-1,4-dihydro-quinoline-3-carboxylic acid (ciprofloxacin). The product was isolated as an orange solid. MS: (M+H$^+$) 1084; $^1$H NMR (400 MHz, CDCl$_3$) δ 13.47 (s, 1H), 13.20 (s, 1H), 13.13 (s, 1H), 12.06 (s, 1H), 8.80 (s, 1H), 8.38 (s, 1H), 7.90 (d, J=13.5 Hz, 1H), 6.62 (dd, J=15.1 and 11.2 Hz, 1H), 6.42 (d, J=11.9 Hz, 1H), 6.20 (d, J=11.7 Hz, 1H), 5.98 (dd, J=15.7 and 5.0 Hz, 1H), 5.11 (dd, J=12.6 and 7.2 Hz, 1H), 4.94 (d, J=10.9 Hz, 1H), 4.01 (m, 1H), 3.80 (m, 1H), 3.78 (s, 1H), 3.68-3.16 (complex pattern), 3.02 (s, 1H), 3.01 (m, 1H), 2.40 (m, 1H), 2.21 (s, 3H), 2.08 (s, 3H), 2.04 (s, 3H), 1.78 (s, 3H), 1.71 (m, 1H), 1.54 (m, 1H), 1.34 (m, 1H), 1.22 (m, 2H), 1.01 (d, J=6.9 Hz, 3H), 0.92 (d, J=7.0 Hz, 3H), 0.61 (d, J=7.2 Hz, 3H), −0.30 (d, J=6.2 Hz, 3H).

EXAMPLE 21

(R/S)-3-[1-(3-Carboxy-1-cyclopropyl-6-fluoro-8-methoxy-4-oxo-1,4-dihydroquinolin-7-yl)-pyrrolidinyl-3-hydrazino-methylenyl]-rifamycin SV:

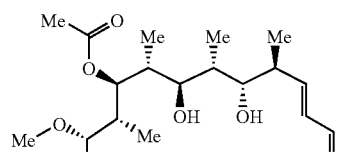
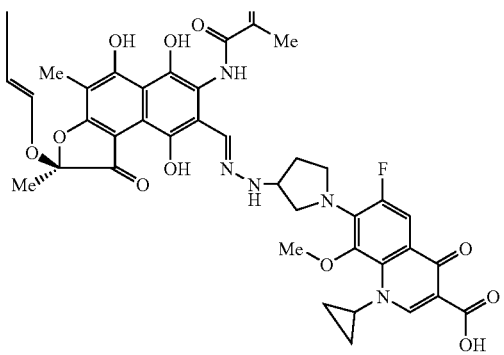

The title compound was prepared by using the same procedure as described for the preparation of Example 6 except 7-(3-amino-pyrrolidin-1-yl)-1-cyclopropyl-6-fluoro-8-methoxy-4-oxo-1,4-dihydro-quinoline-3-carboxylic acid was used instead of 7-(3-aminopyrrolidin-1-yl)-8-chloro-1-cyclopropyl-6-fluoro-4-oxo-1,4-dihydroquinoline-3-carboxylic acid (clinafloxacin). The product was isolated as a mixture of diastereomers as an orange solid (34% yield). MS: (M+H$^+$) 1084.

EXAMPLE 22

(R/S)-3-[1-(3-Carboxy-1-cyclopropyl-6-fluoro-8-methoxy-4-oxo-1,4-dihydroquinolin-7-yl)-pyrrolidinyl-3-methylhydrazino-methylenyl]-rifamycin SV:

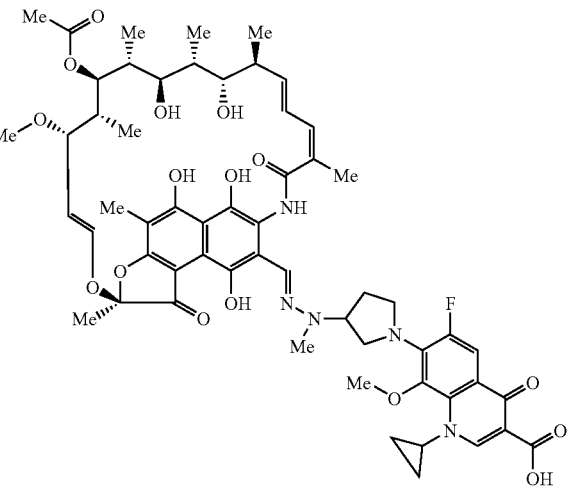

The title compound was prepared by using the same procedure as described for the preparation of Example 15 except 1-cyclopropyl-6-fluoro-8-methoxy-7-(3-methylamino-pyrrolidin-1-yl)-4-oxo-1,4-dihydro-quinoline-3-carboxylic acid was used instead of 1-Cyclopropyl-6-fluoro-7-[3-(N-methyl-hydrazino)-pyrrolidin-1-yl]-4-oxo-1,4-dihydro-quinoline-3-carboxylic acid in the step 4. The product was isolated as a mixture of diastereomers as an orange solid (43% yield). MS: (M+H$^+$) 1098.

EXAMPLE 23

(R/S)-3-[4-(3-Carboxy-1-cyclopropyl-6-fluoro-8-methoxy-4-oxo-1,4-dihydroquinolin-7-yl)-3-carboxy-piperazin-1-yl-aminomethylenyl]-rifamycin SV:

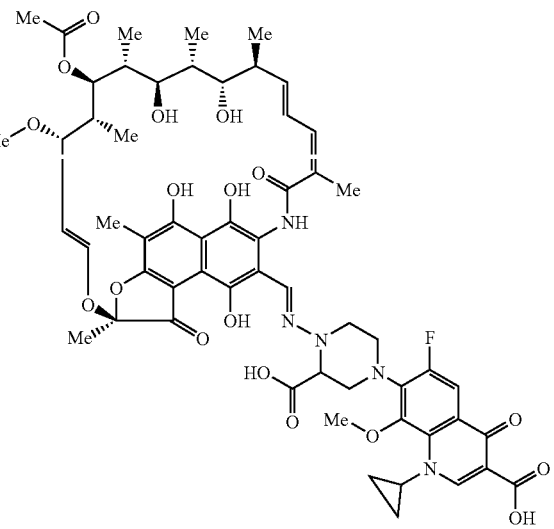

The title compound was prepared by using the same procedure as described for the preparation of Example 4 except 7-(3-carboxy-piperazin-1-yl)-1-cyclopropyl-6-fluoro-8-methoxy-4-oxo-1,4-dihydro-quinoline-3-carboxylic acid was used instead of 1-cyclopropyl-6-fluoro-4-oxo-7-piperazin-1-yl-1,4-dihydro-quinoline-3-carboxylic acid (ciprofloxacin). The product was isolated as a mixture of diastereomers as an orange solid (25% yield). MS: (M+H+) 1128.

EXAMPLE 24

(R/S)-3-[1-(3-Carboxy-1-cyclopropyl-6-fluoro-8-methoxy-4-oxo-1,4-dihydroquinolin-7-yl)-piperidin-3-hydrazino-methylenyl]-rifamycin SV:

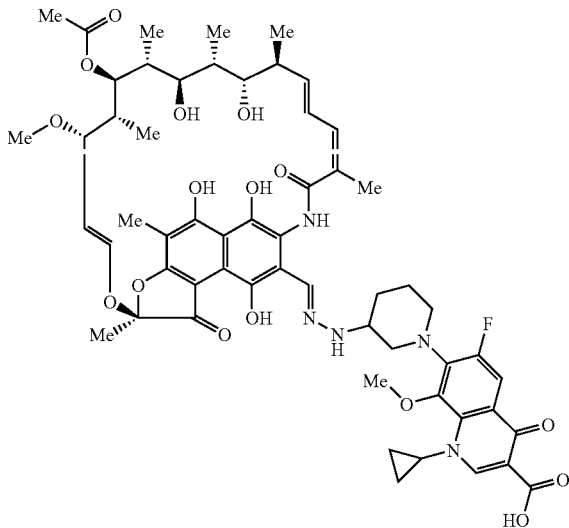

The title compound was prepared by using the same procedure as described for the preparation of Example 6 except 7-(3-amino-piperidin-1-yl)-1-cyclopropyl-6-fluoro-8-methoxy-4-oxo-1,4-dihydro-quinoline-3-carboxylic acid was used instead of 7-(3-aminopyrrolidin-1-yl)-8-chloro-1-cyclopropyl-6-fluoro-4-oxo-1,4-dihydroquinoline-3-carboxylic acid (clinafloxacin). The product was isolated as a mixture of diastereomers as an orange solid (47% yield). MS: (M+H+) 1098.

EXAMPLE 25

3-{4-[1-(3-Carboxy-1-cyclopropyl-6-fluoro-8-methoxy-4-oxo-1,4-dihydroquinolin-7-yl)-piperazin-4-yl]-piperidin-1-yl-aminomethylenyl}-rifamycin SV:

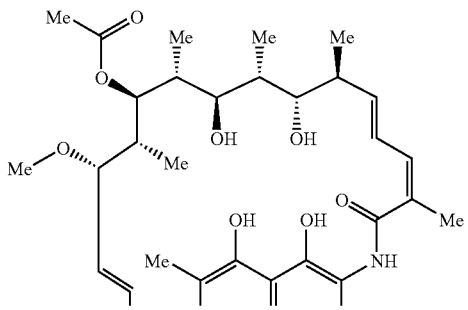

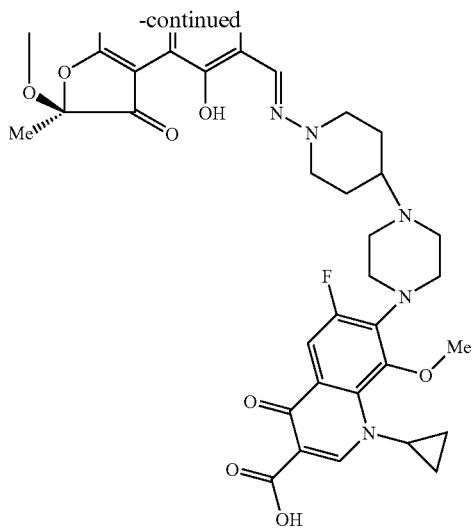

The title compound was prepared by using the same procedure as described for the preparation of Example 4 except 1-cyclopropyl-6-fluoro-8-methoxy-4-oxo-7-(4-piperidin-4-yl-piperazin-1-yl)-1,4-dihydro-quinoline-3-carboxylic acid (prepared through reductive amination of 1-cyclopropyl-6-fluoro-8-methoxy-4-oxo-7-piperazin-1-yl-1,4-dihydro-quinoline-3-carboxylic acid and BOC piperidone, followed by deprotection, Domagala, J. M. et al: *J. Med. Chem.* 1991, 34, 1142-1154; Sanchez, J. P. et al: *J. Med. Chem.* 1988, 31, 983-991) was used instead of 1-cyclopropyl-6-fluoro-4-oxo-7-piperazin-1-yl-1,4-dihydro-quinoline-3-carboxylic acid (ciprofloxacin). The product was isolated as an orange solid. MS: (M+H+) 1167; $^1$H NMR (400 MHz, CDCl$_3$) δ 13.49 (s, 1H), 13.24 (s, 1H), 12.01 (s, 1H), 8.79 (s, 1H), 8.26 (s, 1H), 7.86 (d, J=12.4 Hz, 1H), 6.59 (dd, J=15.8 and 11.1 Hz, 1H), 6.40 (d, J=10.7 Hz, 1H), 6.21 (d, J=8.7 Hz, 1H), 5.95 (dd, J=15.7 and 5.0 Hz, 1H), 5.11 (dd, J=12.7 and 7.2 Hz, 1H), 4.93 (d, J=11.2 Hz, 1H), 4.00 (m, 1H), 3.74 (s, 3H), 3.70 (m, 1H), 3.60 (m, 1H), 3.45 (m, 4H), 3.02 (s, 3H), 2.99 (m, 1H), 2.83-2.32 (complex pattern), 2.21 (s, 3H), 2.06 (s, 3H), 2.04 (s, 3H), 1.94 (m, 1H), 1.78 (s, 3H), 1.70 (m, 1H), 1.54 (m, 1H), 1.37 (m, 1H), 1.20 (d, J=6.9 Hz, 3H), 1.00 (d, J=7.0 Hz, 3H), 0.87 (d, J=6.9 Hz, 3H), 0.60 (d, J=6.3 Hz, 3H), −0.30 (d, J=7.0 Hz, 3H).

EXAMPLE 26

(R/S)-3-{4-[1-(3-Carboxy-1-cyclopropyl-6-fluoro-8-methoxy-4-oxo-1,4-dihydroquinolin-7-yl)-pyrrolidin-3-ylamino]-piperidin-1-yl-aminomethylenyl}-rifamycin SV:

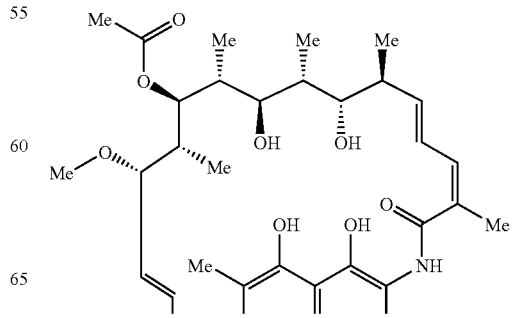

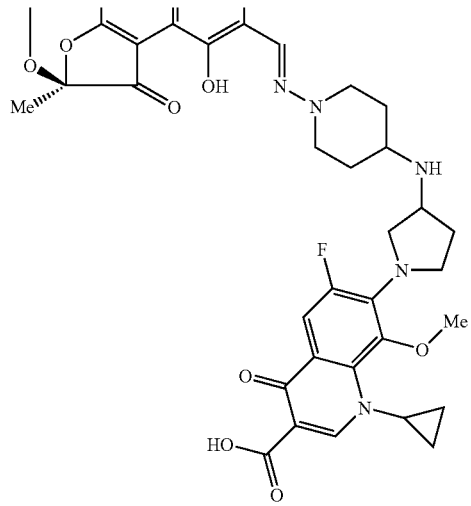

The title compound was prepared by using the same procedure as described for the preparation of Example 4 except 1-cyclopropyl-6-fluoro-8-methoxy-4-oxo-7-[3-(piperidin-4-ylamino)-pyrrolidin-1-yl]-1,4-dihydro-quinoline-3-carboxylic acid [prepared similarly as 1-cyclopropyl-6-fluoro-8-methoxy-4-oxo-7-(4-piperidin-4-yl-piperazin-1-yl)-1,4-dihydro-quinoline-3-carboxylic acid in example 25] was used instead of 1-cyclopropyl-6-fluoro-4-oxo-7-piperazin-1-yl-1,4-dihydro-quinoline-3-carboxylic acid (ciprofloxacin). The product was isolated as a mixture of diastereomers in an orange. MS: (M+H⁺) 1167.

EXAMPLE 27

3-{4-[1-(3-Carboxy-1-cyclopropyl-6-fluoro-8-methoxy-4-oxo-1,4-dihydroquinolin-7-yl)-piperidin-4-yl]-piperazin-1-yl-aminomethylenyl}-rifamycin SV:

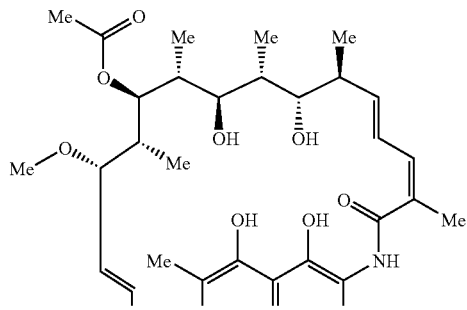

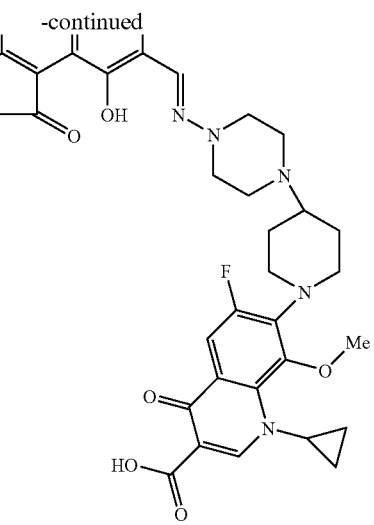

The title compound was prepared by using the same procedure as described for the preparation of Example 4 except 1-cyclopropyl-6-fluoro-8-methoxy-4-oxo-7-(4-piperazin-1-yl-piperidin-1-yl)-1,4-dihydro-quinoline-3-carboxylic acid [prepared similarly as 1-cyclopropyl-6-fluoro-8-methoxy-4-oxo-7-(4-piperidin-4-yl-piperazin-1-yl)-1,4-dihydro-quinoline-3-carboxylic acid in example 25] was used instead of 1-cyclopropyl-6-fluoro-4-oxo-7-piperazin-1-yl-1,4-dihydro-quinoline-3-carboxylic acid (ciprofloxacin). The product was isolated as an orange solid. MS: (M+H⁺) 1167; $^1$H NMR (400 MHz, CDCl$_3$) δ 13.46 (s, 1H), 13.22 (s, 1H), 12.04 (s, 1H), 8.80 (s, 1H), 8.29 (s, 1H), 7.88 (d, J=11.8 Hz, 1H), 6.61 (dd, J=15.8 and 11.9 Hz, 1H), 6.39 (d, J=10.9 Hz, 1H), 6.21 (d, J=12.4 Hz, 1H), 5.95 (dd, J=16.8 and 4.7 Hz, 1H), 5.11 (dd, J=12.7 and 6.9 Hz, 1H), 4.94 (d, J=9.9 Hz, 1H), 4.01 (m, 1H), 3.76 (s, 3H), 3.64 (m, 3H), 3.48 (d, J=7.1 Hz, 2H), 3.22 (m, 4H), 3.12 (m, 1H), 3.03 (s, 3H), 3.00 (m, 1H), 2.79 (m, 3H), 2.38 (m, 1H), 2.22 (s, 3H), 2.05 (s, 3H), 1.98 (m, 1H), 1.79 (s, 3H), 1.71 (m, 3H), 1.55 (m, 1H), 1.35 (m, 1H), 1.21 (d, J=7.2 Hz, 2H), 1.01 (d, J=7.0 Hz, 3H), 0.89 (d, J=7.1 Hz, 3H), 0.60 (d, J=7.3 Hz, 3H), −0.30 (d, J=6.1 Hz, 3H).

EXAMPLE 28

(R/S)-3-{3-[1-(3-carboxy-1-cyclopropyl-6-fluoro-8-methoxy-4-oxo-1,4-dihydroquinolin-7-yl)-piperazin-4-yl]-pyrrolidinyl-1-hydrazino-methylenyl}-rifamycin SV:

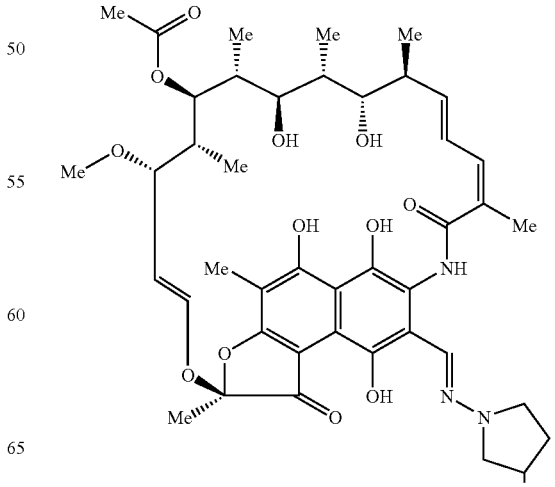

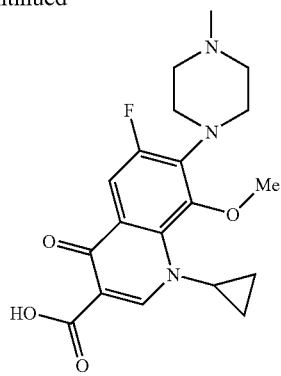

The title compound was prepared by using the same procedure as described for the preparation of Example 4 except 1-cyclopropyl-6-fluoro-8-methoxy-4-oxo-7-(4-pyrrolidin-3-yl-piperazin-1-yl)-1,4-dihydro-quinoline-3-carboxylic acid [prepared similarly as 1-cyclopropyl-6-fluoro-8-methoxy-4-oxo-7-(4-piperidin-4-yl-piperazin-1-yl)-1,4-dihydro-quinoline-3-carboxylic acid in example 25] was used instead of 1-cyclopropyl-6-fluoro-4-oxo-7-piperazin-1-yl-1,4-dihydro-quinoline-3-carboxylic acid (ciprofloxacin). The product was isolated as a mixture of diastereomers in an orange solid. MS: (M+H$^+$) 1153.

EXAMPLE 29

(R/S)-3-[1-(3-Carboxy-1-cyclopropyl-6-fluoro-8-methoxy-4-oxo-1,4-dihydroquinolin-7-yl)-pyrrolidinyl-3-isopropylhydrazino-methylenyl]-rifamycin SV:

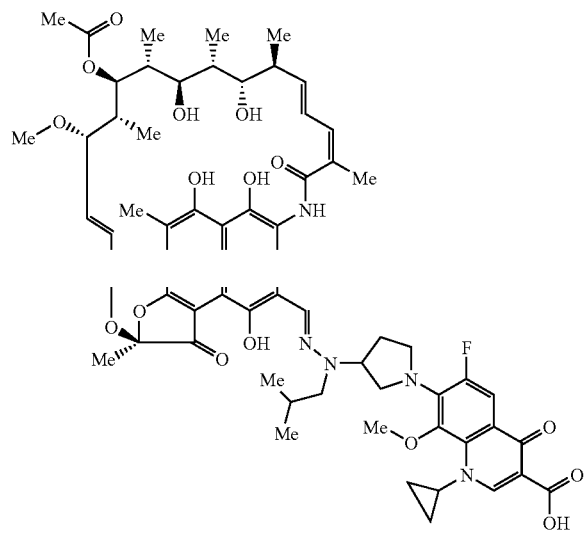

The title compound was prepared by using a similar procedure as described for the preparation of Example 22. The product was isolated as a mixture of diastereomers as an orange solid (65% yield). MS: (M+H$^+$) 1140.

EXAMPLE 30

(R/S)-3-[1-(3-carboxy-1-cyclopropyl-6-fluoro-8-methoxy-4-oxo-1,4-dihydroquinolin-7-yl)-pyrrolidinyl-3-(pyridin-2-ylmethyl)hydrazino-methylenyl]-rifamycin SV:

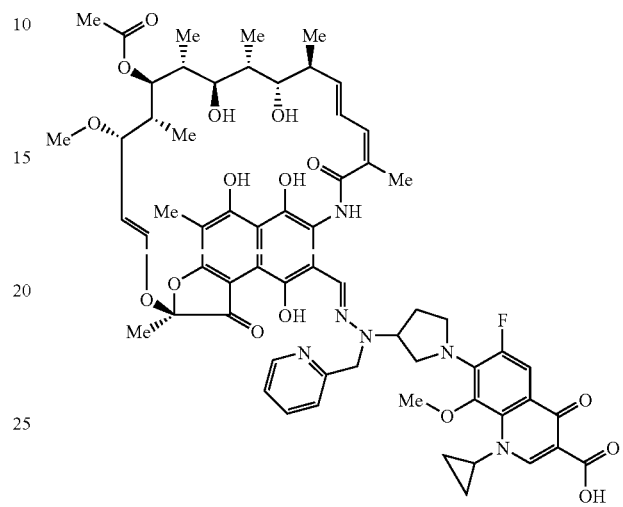

The title compound was prepared by using a similar procedure as described for the preparation of Example 22. The product was isolated as a mixture of diastereomers as an orange solid. MS: (M+H$^+$) 1175.

EXAMPLE 31

(R/S)-3-{4-[1-(3-Carboxy-8-chloro-1-cyclopropyl-6-fluoro-4-oxo-1,4-dihydroquinolin-7-yl)-pyrrolidin-3-ylcarbamoyl]-piperidin-1-yl-aminomethylenyl}-rifamycin SV:

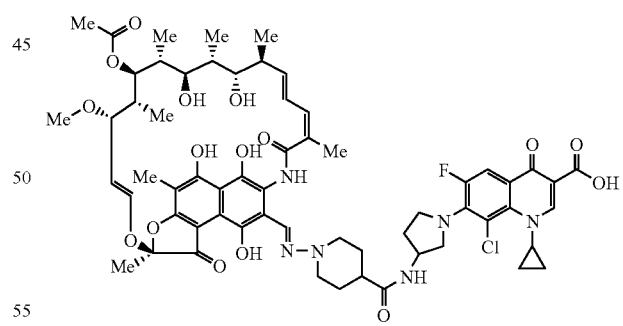

Step 1. 3-[(4-Carboxy)-piperidin-1-yl-aminomethylenyl]-rifamycin SV: 3-[(4-Carboxy)-piperidin-1-yl-aminomethylenyl]-rifamycin SV was prepared by using the same procedure as described for the preparation of Example 4 except isonipecotic acid was used instead of 1-cyclopropyl-6-fluoro-4-oxo-7-piperazin-1-yl-1,4-dihydro-quinoline-3-carboxylic acid (ciprofloxacin). The product was isolated as an orange solid. MS: (M+H$^+$) 852.

Step 2. 3-[(4-Carboxy-2,5-dioxo-pyrrolidin-1-yl-ester)-piperidin-1-yl-aminomethylenyl]-rifamycin SV: To a solution of 3-[(4-carboxy)-piperidin-1-yl-aminomethylenyl]-rifamycin SV (130 mg, 0.153 mmol) in THF was added EDC (74 mg, 0.38 mmol), N-hydroxy succinimide (62 mg, 0.534 mmol) and DMAP (4 mg, 0.03 mmol). The resulting mixture was heated in a 35° C. oil bath for 18 hours before adding large amount of dichloromethane and water. The separated organic phase was further washed with water (2×), brine (1×), dried over $Na_2SO_4$, concentrated in vacuo to give desired product as an orange solid. It was used in the next step without further purification. MS: (M+H$^+$) 949.

Step 3. 3-{4-[1-(3-Carboxy-8-chloro-1-cyclopropyl-6-fluoro-4-oxo-1,4-dihydroquinolin-7-yl)-pyrrolidin-3-ylcarbamoyl]-piperidin-1-yl-aminomethylenyl}-rifamycin SV: To a stirred solution of 3-[(4-carboxy-2,5-dioxo-pyrrolidin-1-yl-ester)-piperidin-1-yl-aminomethylenyl]-rifamycin SV (0.07 mmol) in DMF was added 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl) (62 mg, 0.15 mmol) and N-methyl morpholine (39 mg, 0.38 mmol). The resulting mixture was heated in a 35° C. oil bath for 18 hours before the addition of dichloromethane and water. The aqueous layer was adjusted to pH 4 using 0.5 N HCl. The separated aqueous layer was further extracted with dichloromethane (3×). The combines organic phase was washed with brine (1×), dried over $Na_2SO_4$, concentrated in vacuo to give an orange solid, which was purified by preparative thin layer chromatography (10% methanol in dichloromethane) to give title product as an orange solid. MS: (M+H$^+$) 1199.

EXAMPLE 32

3-{4-[4-(3-Carboxy-1-cyclopropyl-6-fluoro-8-methoxy-4-oxo-1,4-dihydroquinolin-7-yl)-piperazine-1-yl-carbonyl]-piperidin-1-yl-aminomethylenyl}-rifamycin SV:

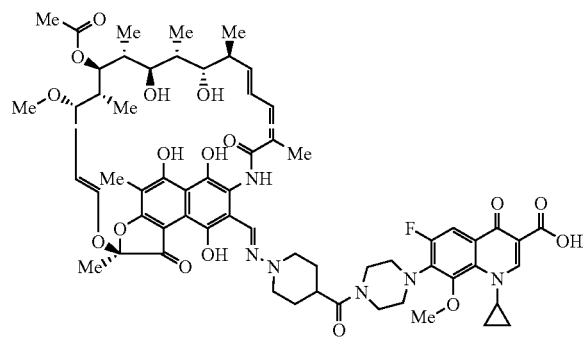

The title compound was prepared by using the same procedure as described for the preparation of Example 31 except 1-cyclopropyl-6-fluoro-8-methoxy-4-oxo-7-piperazin-1-yl-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The product was isolated as an orange solid. MS: (M+H$^+$) 1195; $^1$H NMR (400 MHz, CDCl$_3$)δ 13.45 (s, 1H), 13.21 (s, 1H), 13.14 (s, 1H), 12.05 (s, 1H), 8.81 (s, 1H), 8.36 (s, 1H), 7.91 (d, J=11.8 Hz, 1H), 6.60 (dd, J=15.1 and 12.0 Hz, 1H), 6.40 (d, J=10.8 Hz, 1H), 6.20 (d, J=12.6 Hz, 1H), 5.96 (dd, J=15.6 and 5.6 Hz, 1H), 5.10 (dd, J=12.4 and 6.2 Hz, 1H), 4.93 (d, J=10.3 Hz, 1H), 4.00 (m, 1H), 3.87-3.31 (complex pattern), 3.02 (s, 3H), 2.99 (m, 1H), 2.74 (m, 1H), 2.62 (m, 1H), 2.37 (m, 1H), 2.21 (s, 3H), 2.04 (s, 3H), 1.98 (m, 2H), 1.77 (s, 3H), 1.68 (m, 1H), 1.39 (m, 1H), 1.21 (d, J=7.4 Hz, 3H), 1.00 (d, J=6.2 Hz, 3H), 0.88 (d, J=6.1 Hz, 3H), 0.60 (d, J=6.5 Hz, 3H), −0.3 (d, J=6.9 Hz, 3H).

EXAMPLE 33

(R/S)-3-{4-[1-(3-Carboxy-1-cyclopropyl-6-fluoro-8-methoxy oxo-1,4-dihydroquinolin-7-yl)-pyrrolidin-3-yl]-piperazin-1-yl-aminomethylenyl}-rifamycin SV:

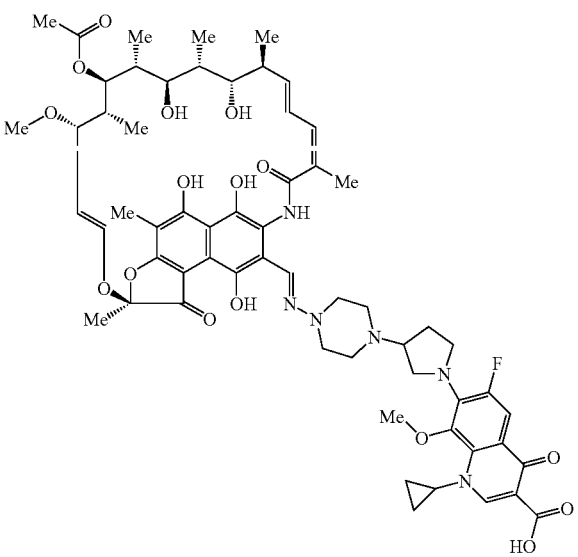

The title compound was prepared by using the same procedure as described for the preparation of Example 4 except 1-cyclopropyl-6-fluoro-8-methoxy-4-oxo-7-(3-piperazin-1-yl-pyrrolidin-1-yl)-1,4-dihydro-quinoline-3-carboxylic acid [prepared similarly as 1-cyclopropyl-6-fluoro-8-methoxy-4-oxo-7-(4-piperidin-4-yl-piperazin-1-yl)-1,4-dihydro-quinoline-3-carboxylic acid in example 25] was used instead of 1-cyclopropyl-6-fluoro-4-oxo-7-piperazin-1-yl-1,4-dihydro-quinoline-3-carboxylic acid (ciprofloxacin). The product was isolated as a mixture of diastereomers as an orange solid. MS: (M+H$^+$) 1153.

EXAMPLE 34

(R/S)-3-{4-[1-(3-Carboxy-1-(2,3-difluoro-phenyl)-6-fluoro-4-oxo-1,4-dihydro[1,8]naphthyridine-7-yl)-pyrrolidin-3-yl]-piperazin-1-yl-aminomethylenyl}-rifamycin SV:

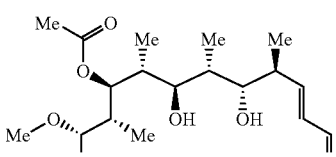

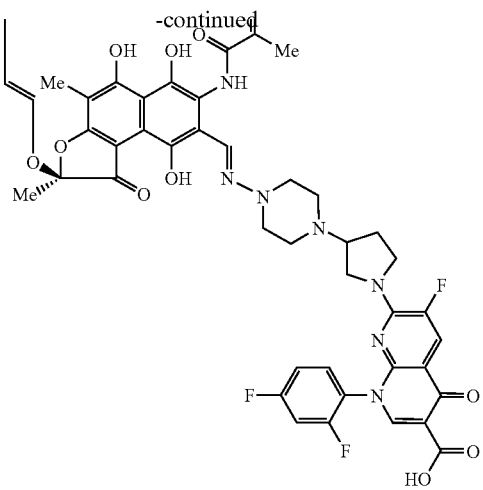

The title compound was prepared by using a similar procedure as described for the preparation of Example 33. The product was isolated as an orange solid in 32% yield. MS: (M+H$^+$) 1196; $^1$H NMR (400 MHz, CDCl$_3$) δ 13.43 (s, 1H), 13.19 (s, 1H), 13.12 (s, 1H), 12.01 (s, 1H), 8.60 (s, 1H), 8.26 (s, 1H), 8.00 (d, J=12.7 Hz, 1H), 7.39 (m 1H), 7.05 (m, 1H), 6.58 (dd, J=14.6 and 10.9 Hz, 1H), 6.28 (d, J=11.1 Hz, 1H), 6.19 (d, J=12.5 Hz, 1H), 5.93 (dd, J=15.0 and 5.0 Hz, 1H), 5.09 (dd, J=12.5 and 6.6 Hz, 1H), 4.92 (d, J=11.0 Hz, 1H), 3.75 (d, J=9.3 Hz, 1H), 3.63 (d, J=3.6 Hz, 1H), 3.47 (m, 3H), 3.14 (m, 3H), 3.01 (s, 3H), 2.99 (m, 1H), 2.69 (m, 2H), 2.37 (m, 1H), 2.19 (s, 3H), 2.03 (s, 3H), 1.77 (s, 3H), 1.68 (m, 3H), 1.51 (m, 1H), 1.32 (m, 1H), 0.99 (d, J=7.1 Hz, 3H), 0.84 (d, J=6.3 Hz, 3H), 0.57 (d, J=6.8 Hz, 3H), −0.32 (d, J=7.2 Hz, 3H).

EXAMPLE 35

3-[4-(3-Carboxy-1-cyclopropyl-6-fluoro-4-oxo-1,4-dihydro-[1,8]naphthyridine-7-yl)-piperazin-1-yl-aminomethylenyl]-rifamycin SV:

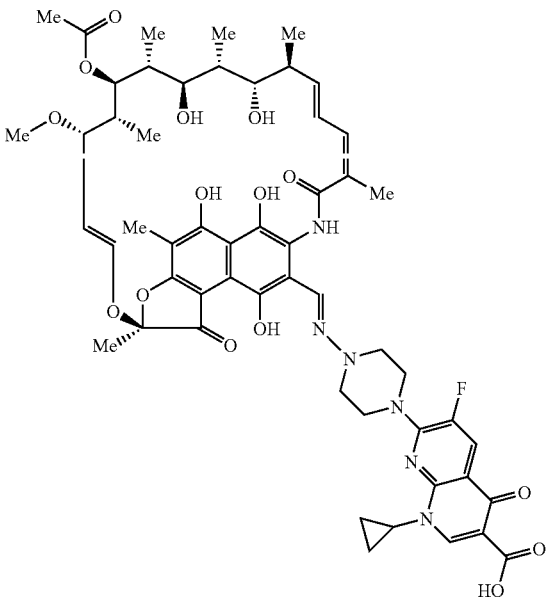

The title compound was prepared by using the same procedure as described for the preparation of Example 4 except 1-cyclopropyl-6-fluoro-4-oxo-7-piperazin-1-yl-1,4-dihydro-[1,8]naphthyridine-3-carboxylic acid was used instead of 1-cyclopropyl-6-fluoro-4-oxo-7-piperazin-1-yl-1,4-dihydro-quinoline-3-carboxylic acid (ciprofloxacin). The product was isolated as an orange solid in 62% yield. MS: (M+H$^+$) 1055; $^1$H NMR (400 MHz, CDCl$_3$) δ 13.40 (s, 1H), 13.16 (s, 1H), 12.99 (s, 1H), 12.08 (s, 1H), 8.7 (s, 1H), 8.37 (s, 1H), 8.09 (d, J=13.5 Hz, 1H), 6.60 (dd, J=14.6 and 10.7 Hz, 1H), 6.42 (d, J=10.8 Hz, 1H), 6.19 (d, J=12.6 Hz, 1H), 5.97 (dd, J=14.8 and 4.5 Hz, 1H), 5.10 (dd, J=12.6 and 7.2 Hz, 1H), 4.93 (d, J=11.2 Hz, 1H), 4.05 (m, 4H), 3.77-3.17 (complex pattern), 3.01 (s, 3H), 2.99 (m, 1H), 2.39 (m, 1H), 2.20 (s, 3H), 2.04 (s, 3H), 1.78 (s, 3H), 1.68 (m, 2H), 1.54 (m, 1H), 1.36 (m, 2H), 1.07 (m, 2H), 0.99 (d, J=6.2 Hz, 3H), 0.85 (d, J=6.1 Hz, 3H), 0.59 (d, J=6.8 Hz, 3H), −0.31 (d, J=6.1 Hz, 3H).

EXAMPLE 36

(R/S)-3-{4-[1-(3-Carboxy-1-(2,4-difluoro-phenyl)-6-fluoro-4-oxo-1,4-dihydro-[1,8]naphthyridine-7-yl)-pyrrolidin-3-yl-carbonyl]-piperazin-1-yl-aminomethylenyl}-rifamycin SV:

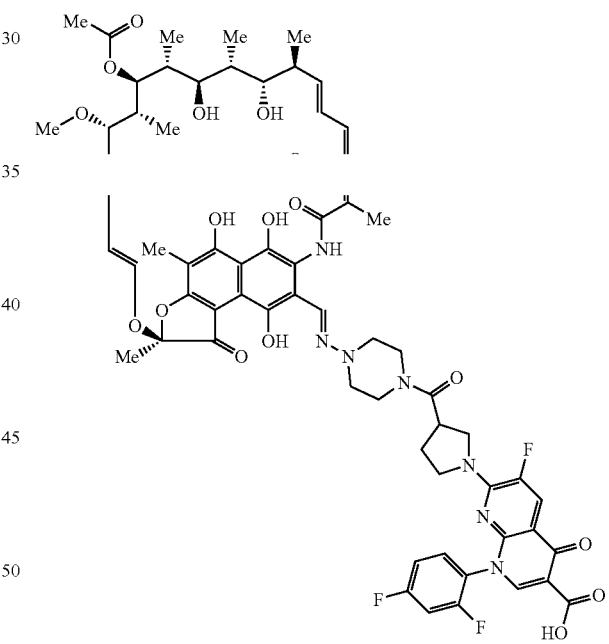

The title compound was prepared by using the same procedure as described for the preparation of Example 4 except 1-(2,4-difluoro-phenyl)-6-fluoro-4-oxo-7-[3-(piperazine-1-carbonyl)-pyrrolidin-1-yl]-1,4-dihydro-[1,8]naphthyridine-3-carboxylic acid [prepared similarly as 1-cyclopropyl-6-fluoro-8-methoxy-4-oxo-7-(4-piperidin-4-yl-piperazin-1-yl)-1,4-dihydro-quinoline-3-carboxylic acid in example 25] was used instead of 1-cyclopropyl-6-fluoro-4-oxo-7-piperazin-1-yl-1,4-dihydro-quinoline-3-carboxylic acid (ciprofloxacin). The product was isolated as an orange solid in 7% yield. MS: (M+H$^+$) 1224.

EXAMPLE 37

(R/S)-3-{4-[1-(3-Carboxy-1-cyclopropyl-6-fluoro-8-methoxy-4-oxo-1,4-dihydroquinoline-7-yl)-pyrrolidin-3-yl-cyclopropyl]-piperazin-1-yl-aminomethylenyl}-rifamycin SV:

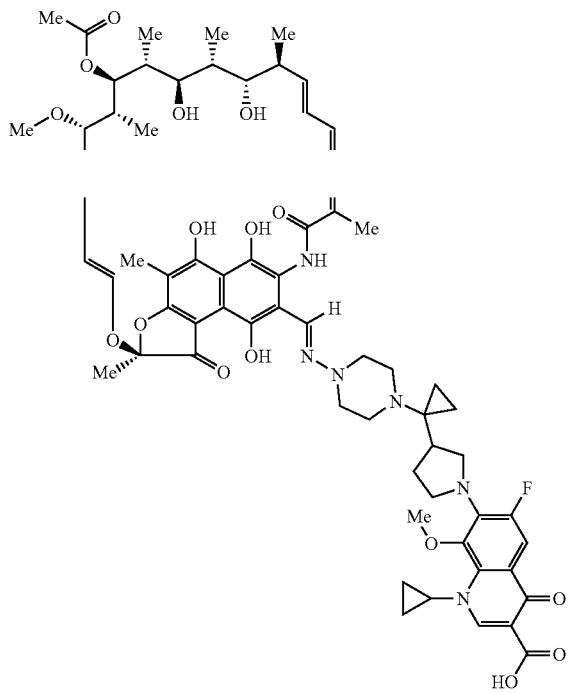

The title compound was prepared by using the same procedure as described for the preparation of Example 4 except 1-cyclopropyl-6-fluoro-8-methoxy-4-oxo-7-[3-(1-piperazin-1-yl-cyclopropyl)-pyrrolidin-1-yl]-1,4-dihydro-quinoline-3-carboxylic acid (prepared similarly as the preparation of the quinolone in Example 16) was used instead of 1-cyclopropyl-6-fluoro-4-oxo-7-piperazin-1-yl-1,4-dihydro-quinoline-3-carboxylic acid (ciprofloxacin). The product was isolated as a mixture of diastereomers as an orange solid (10% yield). MS: (M+H$^+$) 1193.

EXAMPLE 38

(R/S)-3-{4-[1-(3-Carboxy-8-chloro-1-cyclopropyl-6-fluoro-4-oxo-1,4-dihydroquinoline-7-yl)-pyrrolidin-3-yl-cyclopropyl]-piperazin-1-yl-aminomethylenyl}-rifamycin SV:

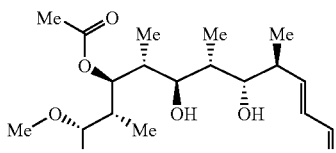

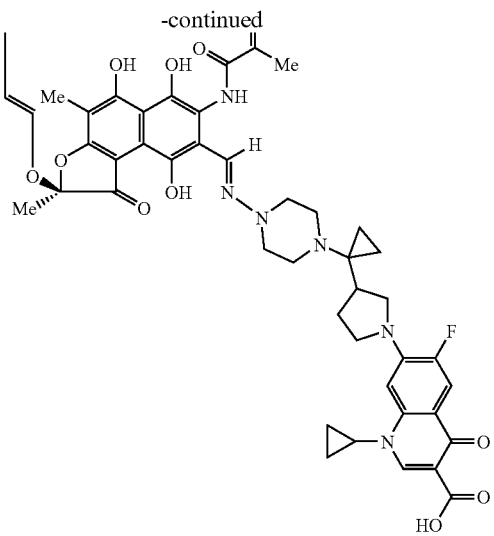

The title compound was prepared by using a similar procedure as described for the preparation of Example 37. The product was isolated as a mixture of diastereomers in an orange solid (10% yield). MS: (M+H$^+$) 1197.

EXAMPLE 39

(R/S)-3-[1-(3-Carboxy-8-chloro-1-cyclopropyl-6-fluoro-4-oxo-1,4-dihydroquinolin-7-yl)-pyrrolidin-3-yl-methyl-hydrazino-methylenyl]-rifamycin SV:

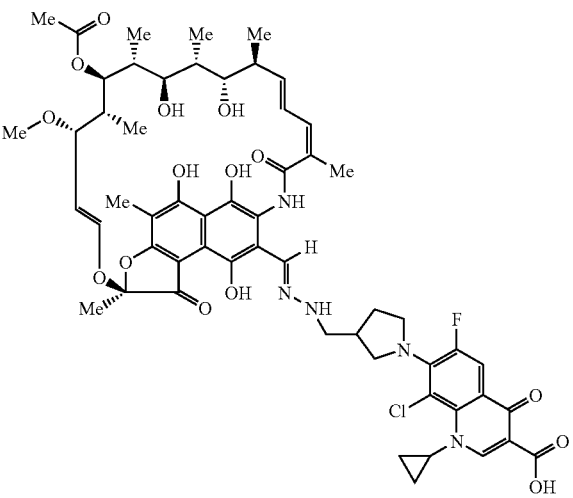

The title compound was prepared by using the same procedure as described for the preparation of Example 6 except 7-(3-aminomethyl-pyrrolidin-1-yl)-8-chloro-1-cyclopropyl-6-fluoro-4-oxo-1,4-dihydro-quinoline-3-carboxylic acid (prepared by following procedure: Domagala, J. M. et al: *J. Med. Chem.* 1991, 34, 1142-1154; Sanchez, J. P. et al: *J. Med. Chem.* 1988, 31, 983-991) was used instead of 7-(3-aminopyrrolidin-1-yl)-8-chloro-1-cyclopropyl-6-fluoro-4-oxo-1,4-dihydroquinoline-3-carboxylic acid (clinafloxacin). The product was isolated as a mixture of diastereomers as an orange solid. MS: (M+H$^+$) 1102.

EXAMPLE 40

3-[4-(3-Carboxy-8-chloro-1-cyclopropyl-6-fluoro-4-oxo-1,4-dihydroquinolin-7-yl)-piperazin-1-yl-aminomethylenyl]-rifamycin SV:

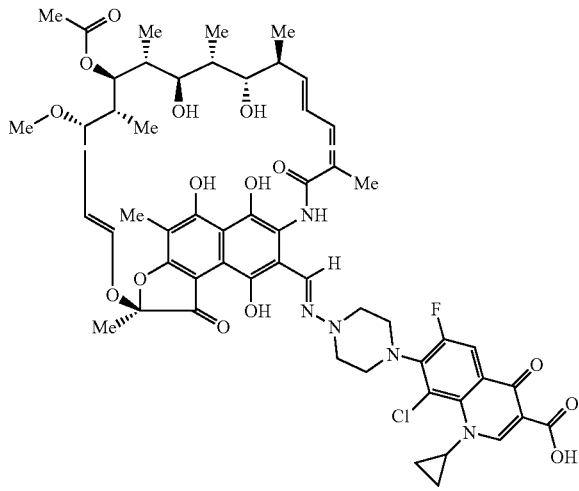

The title compound was prepared by using the same procedure as described for the preparation of Example 4 except 8-chloro-1-cyclopropyl-6-fluoro-4-oxo-7-piperazin-1-yl-1,4-dihydro-quinoline-3-carboxylic acid (prepared by following procedures: Domagala, J. M. et al: *J. Med. Chem.* 1991, 34, 1142-1154; Sanchez, J. P. et al: *J. Med. Chem.* 1988, 31, 983-991) was used instead of 1-cyclopropyl-6-fluoro-4-oxo-7-piperazin-1-yl-1,4-dihydro-quinoline-3-carboxylic acid (ciprofloxacin). The product was isolated as an orange solid in 29% yield. MS: (M+H⁺) 1088; ¹H NMR (400 MHz, CDCl₃) δ 13.45 (s, 1H), 13.21 (s, 1H), 13.13 (s, 1H), 12.07 (s, 1H), 8.90 (s, 1H), 8.38 (s, 1H), 8.07 (d, J=11.7 Hz, 1H), 6.62 (dd, J=15.5 and 11.8 Hz, 1H), 6.41 (d, J=11.1 Hz, 1H), 6.21 (d, J=12.4 Hz, 1H), 5.98 (dd, J=16.6 and 5.5 Hz, 1H), 5.11 (dd, J=12.6 and 7.3 Hz, 1H), 4.94 (d, J=10.6 Hz, 1H), 4.33 (m, 1H), 3.79 (d, J=9.4 Hz, 1H), 3.64 (d, J=4.8 Hz, 1H), 3.60-3.13 (complex pattern), 3.03 (s, 3H), 2.99 (m, 1H), 2.40 (m, 1H), 2.21 (s, 3H), 2.07 (s, 1H), 2.05 (s, 3H), 1.78 (s, 3H), 1.72 (m, 1H), 1.52 (m, 1H), 1.35 (m, 1H), 1.31 (d, J=7.9 Hz, 2H), 1.01 (d, J=6.3 Hz, 3H), 0.96 (d, J=3.7 Hz, 2H), 0.92 (d, J=7.1 Hz, 3H), 0.62 (d, J=6.9 Hz, 3H), −0.29 (d, J=6.9 Hz, 3H).

EXAMPLE 41

3-{4-[1-(3-Carboxy-1-cyclopropyl-6-fluoro-8-methoxy-4-oxo-1,4-dihydroquinolin-7-yl)-pyrrolidin-3-yl-ethylamino]-piperidin-1-yl-aminomethylenyl}-rifamycin SV:

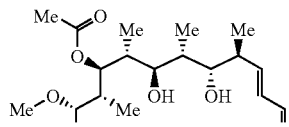

-continued

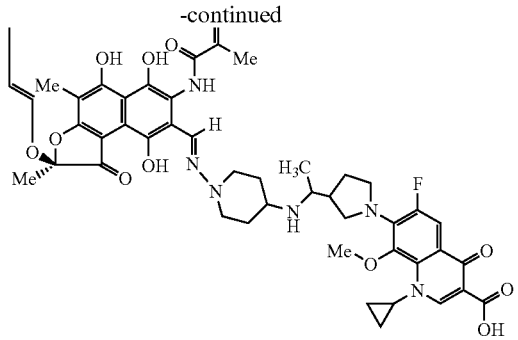

The title compound was prepared by using a similar procedure as described for the preparation of Example 25 except 1-cyclopropyl-6-fluoro-8-methoxy-4-oxo-7-{3-[1-(piperidin-4-ylamino)-ethyl]-pyrrolidin-1-yl}-1,4-dihydroquinoline-3-carboxylic acid [prepared similarly as 1-cyclopropyl-6-fluoro-8-methoxy-4-oxo-7-(4-piperidin-4-yl-piperazin-1-yl)-1,4-dihydro-quinoline-3-carboxylic acid in example 25]. The product was isolated as a mixture of diastereomers as an orange solid (48% yield). MS: (M+H⁺) 1195.

EXAMPLE 42

3-({1-[1-(3-Carboxy-1-cyclopropyl-6-fluoro-8-methoxy-4-oxo-1,4-dihydro-quinolin-7-yl)-pyrrolidin-3-yl]-ethyl}-hydrazinomethylenyl)-rifamycin SV:

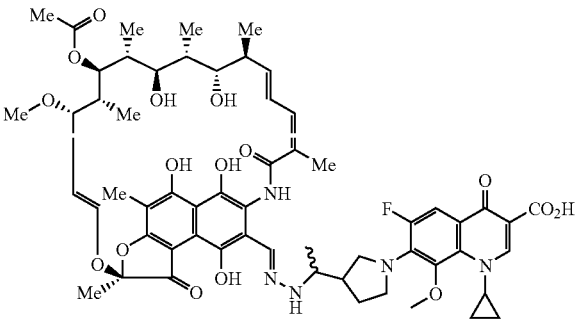

Step 1. N-[1-(1-Benzyl-pyrrolidin-3-yl)-ethyl]-N'-tert-butoxycarbonyl-hydrazinecarboxylic acid tert-butyl ester: To a stirred solution of 1-(1-benzyl-pyrrolidin-3-yl)-ethanone (500 mg, 2.5 mmol) in MeOH (5 mL) were added t-butyl carbazate (264 mg, 2 mmol) and acetic acid (0.1 mL, 2 mmol) and stirred overnight at room temperature. After the mixture was cooled to 0° C., p-TsOH (950 mg, 5 mmol) and NaBH₃CN (471 mg, 7.5 mmol) were added to the mixture and stirred for 1 h at 0° C. and warmed to room temperature and stirred for 3 h. The reaction mixture was cooled to 0° C. and the reaction was quenched with saturated NaHCO₃ solution. The solvent was removed under reduced pressure, resultant residue was diluted with water and extracted with CH₂Cl₂. The combined organic layer was dried over MgSO₄, filtered and evaporated. The residue was dissolved in anhydrous THF, followed by the addition of triethylamine (0.7 mL, 5 mmol) and di-tert-butyl dicarbonate (600 mg, 2.8 mmol) and stirred overnight at room temperature. The reaction mixture was evaporated under reduced pressure and the residue was purified with flash silica gel column chromatography (CH₂Cl₂: MeOH: triethylamine=200:10:1) to give the desired product (700 mg, 67%). ESI MS m/z 420 (M+H⁺).

Step 2. N-[1-(Pyrrolidin-3-yl)-ethyl]-N'-tert-butoxycarbonyl-hydrazinecarboxylic acid tert-butyl ester: To a solution of N-[1-(1-benzyl-pyrrolidin-3-yl)-ethyl]-N'-tert-butoxycarbonyl-hydrazinecarboxylic acid tert-butyl ester (700 mg, 1.67 mmol) in AcOH (20 mL) was added 20% palladium hydroxide (600 mg) and the mixture was stirred overnight under a hydrogen balloon. The catalyst was filtered through a pad of celite and the filtrate was evaporated under reduced pressure. The residue was dissolved in CH₂Cl₂ and washed with 2 N NaOH. The organic layer was dried over MgSO₄, filtered, and evaporated to give the desired product (400 mg). ¹H NMR (400 MHz, CD₃OD) δ3.04-2.83 (m, 5H), 2.21-1.73 (m, 1H), 1.50-0.95 (m, 23H).

Step 3. 7-{3-[1-(N',N'-Di-tert-butoxycarbonyl-hydrazino)-ethyl]-pyrrolidin-1-yl}-1-cyclopropyl-6-fluoro-8-methoxy-4-oxo-1,4-dihydro-quinoline-3-carboxylic acid: To a solution of N-[1-(pyrrolidin-3-yl)-ethyl]-N'-tert-butoxycarbonyl-hydrazinecarboxylic acid tert-butyl ester (750 mg) in CH₃CN (10 mL) were added and 1-cyclopropyl-6,7-difluoro-8-methoxy-4-oxo-1,4-dihydro-quinoline-3-carboxylic acid (300 mg) and triethylamine and refluxed overnight. The mixture was cooled to 0° C. and quenched with 0.5 N HCl and extracted with CH₂Cl₂. The combined organic layer was dried over MgSO₄, filtered and evaporated. The resulting residue was purified with flash silica gel column chromatography to give the desired product (320 mg, 58%).

Step 4. 3-({1-[1-(3-Carboxy-1-cyclopropyl-6-fluoro-8-methoxy-4-oxo-1,4-dihydro-quinolin-7-yl)-pyrrolidin-3-yl]-ethyl}-hydrazinomethyl)-rifamycin SV: To a stirred solution of 7-{3-[1-(N',N'-Di-tert-butoxycarbonyl-hydrazino)-ethyl]-pyrrolidin-1-yl}-1-cyclopropyl-6-fluoro-8-methoxy-4-oxo-1,4-dihydro-quinoline-3-carboxylic acid (320 mg) in dichloroethane (4 mL) was added trifluoacetic acid (2 mL). This was stirred for 1 h at room temperature. The solvent was evaporated under reduced pressure and the residue was dissolved in MeOH (5 mL). To the resultant solution were added AcOH (1.2 mL), water (1.2 mL), NaOAc (300 mg) and 3-formyl rifamycinSV (180 mg) and allowed to stir overnight at room temperature. To the heterogeneous reaction mixture was added water and the resulting solid was filtered and washed with water. The filter cake was dissolved in MeOH (2 mL) and AcOH (0.1 mL) and ascorbic acid (0.1 mL) were added at 0° C. The resulting cold solution was triturated with water and the resulting solid was filtered to give the desired product (150 mg) as a four distereomeric mixture. ESI MS m/z 1112 (M+H⁺).

EXAMPLE 43

(R/S)-3-[1-[3-Carboxy-1-(2,4-difluoro-phenyl)-6-fluoro-4-oxo-1,4-dihydro-[1,8]naphthyridin-7-yl]-pyrrolidinyl-3-N'-methylhydrazinomethylenyl]rifamycin SV:

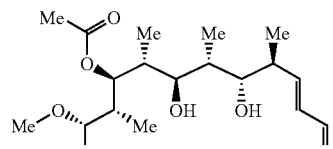

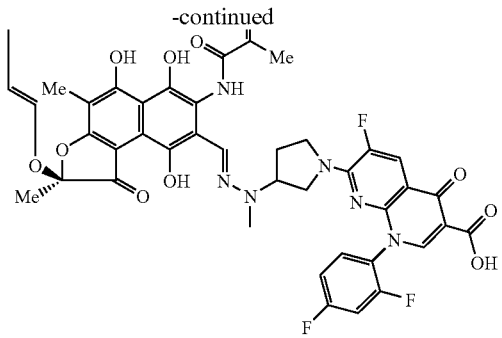

The title compound was prepared by following a similar procedure as employed for the preparation of Example 15. The product was obtained as an orange solid (15 mg). ESI MS m/z 1141 (M+H+); ¹H NMR (400 MHz, CDCl₃) δ 13.50 (br s, OH) 12.39 (s, OH), 8.94 (m, 1H), 8.37 (m, 2H), 7.59 (m, 1H), 7.40 (m, 4H), 6.59 (m, 1H), 6.52 (m, 2H), 6.22 (m, 1H), 5.40 (m, 1H), 5.22 (m, 1H), 4.35 (m, 3H), 4.01 (m, 4H), 3.81 (m, 4H), 3.35 (s, 3H), 3.14 (m, 3H), 2.66 (m, 2H), 2.53 (s, 3H), 2.37 (s, 3H), 2.34-1.86 (br m, 2H), 2.10 (s, 3H), 1.70 (m, 2H), 1.55 (m, 3H), 1.31 (m, 3H), 1.19-1.05 (m, 3H), 0.946 (m, 3H), 0.06 (m, 3H).

EXAMPLE 44

(R/S)-3-[9-fluoro-3-methyl-10-(3-methyl-piperazin-1-hydrazinomethylenyl)-7-oxo-7H-pyrido[1,2,3-de]-1,4-benzoxazine-6-carboxylic acid]rifamycin SV:

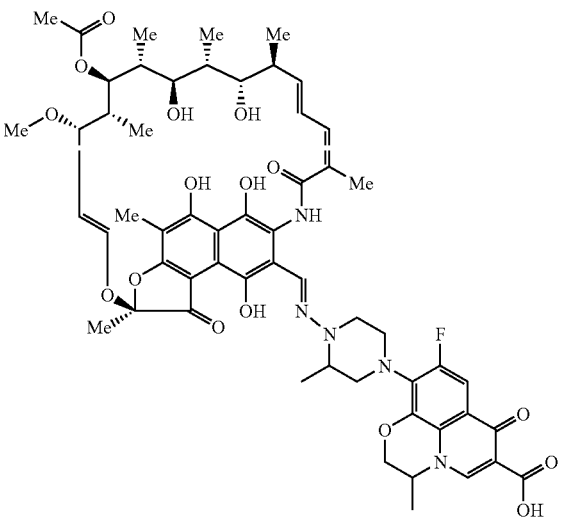

Step 1. 9-fluoro-3-methyl-10-(3-methyl-piperazine)-7-oxo-7H-pyrido[1,2,3-de]-1,4-benzoxazine-6-carboxylic acid: To a solution of 9,10-difluoro-2,3-dihydro-3-methyl-7-oxo-7H-pyrido[1,2,3-de]-1,4-benzoxazine-6-carboxylic acid (1.4 g, 4.99 mmol) in pyridine (15 ml) was added 2-methyl piperazine (1.00 g, 9.99 mmol) and refluxed at 100° C. for 24 hours. The reaction mixture was cooled and the product crashed out of solution providing the pure desired product (1.0 g, 55% yield). ESI MS m/z: [M+H]+ 362.

Step 2. 9-Fluoro-3-methyl-10-(3-methyl-4-hydrazino-piperazine)-7-oxo-7H-pyrido[1,2,3-de]-1,4-benzoxazine-6- carboxylic acid: To a solution of 9-fluoro-3-methyl-10-(3-methyl-piperazine)-7-oxo-7H-pyrido[1,2,3-de]-1,4-benzoxazine-6-carboxylic acid (300 mg, 0.83 mmol) in 1 mL acetic acid was added 0.3 mL 3 N HCl solution. The solution was cooled to 0° C. and a solution of sodium nitrite (257 mgs, 3.73 mmol) in water (1.5 mL) was added drop-wise. The suspension was allowed to slowly warm up to room temperature and stirring was maintained at this temperature for 12 hours. The suspension was diluted with 5% citric acid, and extracted three times with 20% isopropanol/dichloromethane. The combined extracts were dried with $Na_2SO_4$ and filtered, and concentrated in vacuo. The resultant solid was taken up in 1:1 $AcOH/H_2O$ (15 ml) and zinc powder (217 mgs, 3.32 mmol) was added in portions and the resultant mixture was stirred for 12 hours. The suspension was filtered through a layer of celite, washed with MeOH and the filtrate containing product was used for next step without further purification, ESI MS m/z 377 (M+H+).

Step 3. (R/S)-3-[9-fluoro-3-methyl-10-(3-methyl-piperazin-1-hydrazinomethylenyl)-7-oxo-7H-pyrido[1,2,3-de]-1,4-benzoxazine-6-carboxylic acid]rifamycin SV: To a solution of 9-fluoro-3-methyl-10-(3-methyl-4-hydrazinopiperazine)-7-oxo-7H-pyrido[1,2,3-de]-1,4-benzoxazine-6-carboxylic acid in methanol, was added solid sodium acetate to pH=5, followed by 3-formylrifamycin SV (150 mg, 0.20 mmol) and stirred for 15 hours. The resultant solution was partitioned between dichloromethane and 10% citric acid solution. The separated organic layer was washed with 10% citric acid solution (1×), dried over sodium sulfate, concentrated in vacuo to give a red solid, which was purified by preparative thin layer chromatography in 5% methanol/chloroform to give the title compound as an orange solid (40 mg). ESI MS m/z 1084 (M+H+); $^1$H NMR (400 MHz, $CDCl_3$) δ 13.31 (s, 1H) 8.90 (s, 1H), 8.58 (s, 1H), 8.04 (d, J=11.73 Hz, 1H), 6.90-6.81 (m, 1H), 6.80-6.40 (m, 4H), 5.41-5.34 (m, 1H), 5.24 (m, 1H), 4.84-4.60 (m, 3H), 4.12-3.40 (m, 10H), 3.32 (s, 3H), 3.30 (m, 1H), 2.67 (m, 2H), 2.51 (s, 3H), 2.34 (m, 6H), 2.08 (m, 3H), 2.07-1.94 (m, 2H), 1.90 (m, 2H), 1.66 (m, 3H), 1.54 (m, 3H), 1.43 (m, 4H), 1.30 (m, 4H), 1.17 (m, 4H), 0.91 (m, 3H).

EXAMPLE 45

(R/S)-3-[4-[1-[1-(3-Carboxy-1-cyclopropyl-7-fluoro-8-chloro-4-oxo-4H-quinolin-7-yl)pyrrolidin-3-yl]cycloprop-1-ylamino]piperidin-1-ylaminomethylenyl]rifamycin SV:

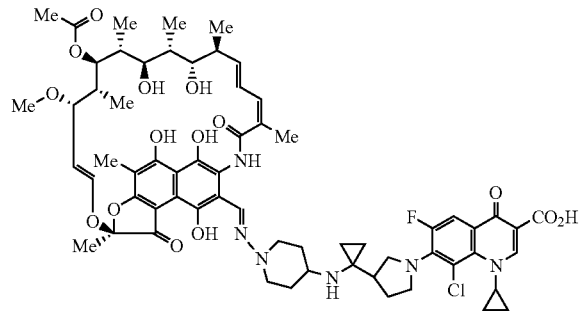

Step 1. 4-Benzylaminopiperidine-1-carboxylic acid tert-butyl ester: To a stirred solution of 4-oxo-piperidine-1-carboxylic acid tert-butyl ester (30.0 g, 151 mmol) and benzylamine (16.4 mL, 151 mmol) in methanol (500 mL) was added acetic acid (20 mL, 349 mmol). After 30 minutes, $NaBH_3CN$ (18.9 g, 301 mmol) was added in three portions. The resulting solution was stirred at RT overnight, then concentrated in vacuo. The resulting yellow oil was partitioned between 1:1$H_2O$—$CH_2Cl_2$ (300 mL). The aqueous was separated, extracted with $CH_2Cl_2$ (3×100 mL), and the combined organic layer was washed with brine, dried ($Na_2SO_4$), and concentrated in vacuo. The oil was purified by chromatography (10:1 to 2:1 hexanes-EtOAc) to afford a white crystalline solid (31.3 g, 72%). ESI MS m/z 290.9 (M); $^1$H NMR (400 MHz, $CDCl_3$) δ 7.36-7.32 (m, 5H, Ph), 4.08 (d, J=19.8 Hz, 2H), 4.04 (s, 2H, Bn), 3.16 (app t, J=11.7 Hz, 1H), 2.66-2.57 (br m, 2H), 2.00 (app d, J=11.7 Hz, 2H), 1.45 (dd, J=11.0, 21.9 Hz, 2H), 1.35 (s, 9H, t-Bu). $^{13}$C NMR (400 MHz, $CDCl_3$) δ 154.5 (C=O), 129.9 (Ph), 129.52 (Ph), 129.49 (Ph), 129.1 (Ph), 80.4 (t-Bu), 54.9 (pip), 48.2 (pip), 41.7 (broad, pip), 28.0 (t-Bu).

Step 2. 4-(N-Acryloyl-N-benzylamino)piperidine-1-carboxylic acid tert-butyl ester: To a stirred solution of 4-benzylaminopiperidine-1-carboxylic acid tert-butyl ester (30 g, 103 mmol) and acrylic acid (12.4 mL, 181 mmol, 1.8 equiv) in dichloromethane (500 mL) was added 1-(3-dimethylaminopropyl)-3-ethylcarbodiimide hydrochloride (43.3 g, 226 mmol, 2.2 equiv) followed by 4-dimethylaminopyridine (1.8 g, 15.0 mmol, 0.15 equiv). After stirring at room temperature overnight, $H_2O$ (200 mL) was added. The organic layer was separated and washed with brine, dried ($Na_2SO_4$) and concentrated in vacuo. The solid residue was purified by chromatography (10:1 to 1:1 hexanes-EtOAc) to afford a white crystalline solid (33.0 g, 93%). ESI MS m/z 367.1 (M+Na); $^1$H NMR (400 MHz, $CDCl_3$) δ 7.40-7.61 (m, 5H, Ph), 6.81-6.71 and 6.51-6.39 (two multiplets, total 2H), 5.81 and 5.68 (two doublets, J=9.53, total 1H), 4.80 (app t, J=11.7 Hz, 1H), 4.69 and 4.62 (two broad singlets, total 2H, Bn), 4.19 and 4.01 (two broad singlets, total 2H), 2.82 (br s, 2H), 1.73 and 1.71 (two broad singlets, total 2H), 1.55 and 1.49 (two broad singlets, total 2H), 1.48 (s, 9H, t-Bu). $^{13}$C NMR (400 MHz, $CDCl_3$) δ 166.9 (C=O), 154.4 (C=O), 138.0 (Ph), 128.9 (vinyl), 128.6 (vinyl), 128.2 (Ph), 127.1 (Ph), 125.6 (Ph), 79.4 (t-Bu), 52.0 (Bn), 46.4 (pip), 42.9 (br, pip), 29.3 (pip), 28.2 (t-Bu).

Step 3. (R/S)-N-Benzyl-N-(1-tert-butoxycarbonylpiperidin-4-yl)-1-benzylpyrrolidine-3-carboxamide. To a stirred solution of 4-(N-acryloyl-N-benzylamino)piperidine-1-carboxylic acid tert-butyl ester (30 g, 87 mmol) and N-benzyl-N-(methoxymethyl)-N-trimethylsilylmethylamine (33.4 mL, 131 mmol, 1.5 equiv) in toluene (300 mL) was added trifluoroacetic acid (671 µL, 8.7 mmol, 0.1 equiv). The resulting solution was stirred at room temperature overnight, and concentrated. The oil was purified by chromatography (5:1 hexanes-EtOAc to 100% EtOAc) to afford a white solid (21.7 g, 52%). ESI MS m/z 478.3 (M+H). $^1$H NMR (400 MHz, $CDCl_3$) δ 7.47-7.21 (m, 10H), 4.68+4.60 (two s, total 2H), 4.41-4.11 (br m, 2H), 4.02 (app t, J=15.4 Hz, 1H), 3.85-3.69 (m, 2H), 3.25-3.12 (m, 1H), 3.10-2.59 (m, 6H), 2.42-1.96 (m, 3H), 1.83-1.73 (m, 2H), 1.66-1.56 (s+m, total 10H); $^{13}$C NMR (400 MHz, $CDCl_3$) δ 175.5+173.8 (C=O), 154.0+153.9 (C=O), 138.8 (Ph), 138.5 (Ph), 137.7 (Ph), 128.3 (Ph), 128.2 (Ph), 127.7 (Ph), 126.8 (Ph), 126.5 (Ph), 126.2 (Ph), 125.1 (Ph), 79.3+79.0 (t-Bu), 59.76, 59.69 (Bn), 57.8, 57.2 (Bn), 55.6, 55.3, 53.7 (pyr), 51.7 (pyr), 46.0 (pip), 42.9, 42.6 (br, pip), 39.7, 39.7, 30.7, 27.9 (t-Bu).

Step 4: (R/S)-N-Benzyl-N-[1-(1-benzylpyrrolidin-3-yl)cyclopropyl]-N-(1-tert-butoxycarbonylpiperidin-4-yl)amine. A solution of ethylmagnesium bromide (3.0 M in ethyl ether, 13.0 mL, 39.1 mmol, 2.5 equiv) in THF (100 mL) was cooled to −78° C. To this was added a solution of titanium (IV) isopropoxide (4.8 mL, 16.3 mmol, 1.04 equiv) in THF (10 mL) dropwise with the temperature below −70° C. After stirring for thirty minutes, a solution of (R/S)-N-benzyl-N-(1-tert-butoxycarbonylpiperidin-4-yl)-1-benzylpyrrolidine-3-carboxamide (7.5 g, 15.6 mmol) in THF (10 mL) was added. The resulting solution was warmed to RT, heated at reflux for one hour. The mixture was then cooled to 8° C., and ethylmagnesium bromide (3.0 M in ethyl ether, 11.0 mL, 33.1 mmol, 2.1 equiv) was added, followed immediately by a solution of titanium (IV) isopropoxide (4.2 mL, 14.2 mmol, 0.91 equiv) in THF (10 mL). The reaction mixture was stirred at room temperature for one hour then partitioned between 1:1 EtOAc—H$_2$O (500 mL). The organic layer was washed with brine, dried (Na$_2$SO$_4$) and concentrated in vacuo. The residue was purified by chromatography (5:1 hexanes-EtOAc to 100% EtOAc) to give a pale yellow oil (4.7 g, 61%). ESI MS m/z 490.3 (M+H). $^1$H NMR (400 MHz, CDCl$_3$) δ 7.34-7.11 (m, 10H), 4.18-3.98 (br m, 1H), 3.92 (app s, 2H), 3.64 (app t, J=13.2, 1H), 3.55 (d, J=12.5, 1H), 3.00-2.78 (m, 4H), 2.75-2.37 (m, 4H), 2.33-2.21 (m, 1H), 2.10-1.89 (m, 2H), 1.73-1.62 (m, 2H), 1.50-1.37 (s+m, 11H), 1.37-1.14 (m, 2H), 0.71 (app s, 1H), 0.60-0.49 (m, 1H). $^{13}$C NMR (400 MHz, CDCl$_3$) δ 154.20 (C=O), 143.1 (Ph), 138.8 (Ph), 128.5 (Ph), 128.4 (Ph), 127.9 (Ph), 127.7 (Ph), 126.6 (Ph), 125.9 (Ph), 78.8 (t-Bu), 60.6, 58.4, 55.5, 53.2, 48.9, 45.2, 43.3 (br), 42.7 (br), 38.6, 32.1 (br), 28.1 (t-Bu), 7.6 (c-Pr).

Step 5. (R/S)-4-(1-Pyrrolidin-3-ylcyclopropylamino)piperidine-1-carboxylic acid tert-butyl ester: To a solution of (R/S)-N-benzyl-N-[1-(1-benzylpyrrolidin-3-yl)cyclopropyl]-N-(1-tert-butoxycarbonylpiperidin-4-yl)amine (4.7 g, mmol) in acetic acid (50.0 mL) was added 30% Pd/C (340 mg). The resulting mixture was hydrogenated under 50 Psi for 20 hr. The catalyst was filtered off through Celite 545, and the filtrate was concentrated in vacuo. The residue was basified to pH=11 with 2 N NaOH, and the liberated free diamine was extracted (3×20 mL) with CH$_2$Cl$_2$. The organic was dried (Na$_2$SO$_4$) and concentrated to a light yellow glass. The product was then converted to a foamy solid by evacuating in the presence of a small amount of CH$_2$Cl$_2$ (2.6 g, 88%). ESI MS m/z 310.1 (M+H). $^1$H NMR (400 MHz, CDCl$_3$) δ 3.98 (br s, 2H), 3.06-2.86 (m, 3H), 2.83-2.66 (m, 3H), 2.64-2.55 (m, 1H), 2.50-2.33 (m, 1H), 1.91-1.73 (m, 4H), 1.41 (s, 9H), 1.24-1.19 (m, 3H), 1.03 (app t, J=7.3 Hz, 1H), 0.87-0.81 (m, 1H), 0.42 (s, 1H).

Step 6. 7-[3-[1-(1-tert-Butoxycarbonylpiperazin-4-ylamino)cyclopropyl]pyrrolidin-1-yl]-8-chloro-1,4-dihydro-1-cyclopropyl-6-fluoro-4-oxoquinoline-3-carboxylic acid: 4-(1-Pyrrolidin-3-ylcyclopropylamino)piperidine-1-carboxylic acid tert-butyl ester (600 mg, 1.94 mmol, 2 equiv) and 8-chloro-1,4-dihydro-1-cyclopropyl-6,7-difluoro-4-oxoquinoline-3-carboxylic acid (290 mg, 0.97 mmol) were dissolved in MeCN (5 mL) in the presence of triethylamine and heated a reflux for 18 hr. The reaction mixture was cooled and concentrated. The residue was purified by preparative TLC (10:1 CH$_2$Cl$_2$-MeOH) to afford 188 mg (33%) of pure product as a yellow crystalline solid. ESI MS m/z 589.1 (M+H). $^1$H NMR (400 MHz, CDCl$_3$) δ 8.77 (s, 1H), 7.70 (d, J=13.2 Hz, 1H), 4.29 (s, 2H), 3.95-3.90 (m, 3H), 3.54-3.45 (m, 3H), 3.03-2.92 (m, 1H), 2.91-2.65 (two multiplets, 3H), 2.01-1.89 (m, 1H), 1.81 (dd, J=12.5, 21.3 Hz, 2H), 1.52 (quintet, J=10.3, 1H), 1.38 (s, 9H), 1.26-1.10 (m, 3H), 1.02-0.97 (m, 1H), 0.86-0.78 (m, 1H), 0.67-0.47 (m, 4H).

Steps 7.3-[4-[1-[1-(3-Carboxy-1-cyclopropyl-7-fluoro-8-chloro-4-oxo-4H-quinolin-7-yl)pyrrolidin-3-yl]cycloprop-1-ylamino]piperidin-1-ylaminomethyl]rifamycin SV: 7-[3-[1-(1-tert-Butoxycarbonylpiperazin-4-ylamino) cyclopropyl]pyrrolidin-1-yl]-8-chloro-1,4-dihydro-1-cyclopropyl-6-fluoro-4-oxoquinoline-3-carboxylic acid (188 mg, 0.32 mmol) was dissolved in CH$_2$Cl$_2$ (5 mL), trifluoroacetic acid (500 µL, 6.5 mmol, ~20 equiv) was added, and the resulting solution was stirred for 3 hours. The reaction was concentrated to a yellow solid, then dissolved in 2N NaOH (2 mL). Hydroxylamine-O-sulfonic acid (43 mg, 0.38 mmol, 1.2 equiv) was added and the solution was allowed to stir overnight at RT. Acetic acid was added to the turbid mixture to pH=5, followed by 1 mL of MeOH. Then 3-formylrifamycin SV in MeOH (500 µL) was added in 0.2 equiv portions until all of the intermediate hydrazine was consumed (as determined by LCMS). The resulting bright orange-red mixture was stirred overnight at RT. The mixture was concentrated, and the residue was purified by preparative TLC (10:1 CH$_2$Cl$_2$-MeOH) give a red brown solid. A final purification was carried out by reverse phase chromatography (C-18, 25:75 MeCN—H$_2$O to 90:10 MeCN—H$_2$O, then 50:50 MeCN-MeOH) followed by lyophilization to afford 10.6 mg (3%) of final product as a vermillion colored solid. ESI MS m/z 1211.1 (M+H), 1179.7 (M-MeO); $^1$H NMR (400 MHz, CD$_3$OD) δ 8.95 (d, J=5.9 Hz, 1H), 8.20 (d, J=7.3 Hz, 1H), 7.87 (d, J=11.7 Hz, 1H), 7.33-7.20 (br s, 1H), 6.34 (d, J=9.5, 1H), 6.25 (d, J=13.2 Hz, 1H), 6.06 (dd, J=16.1, 6.6 Hz, 1H), 5.16 (d, J=10.3 Hz, 1H), 5.06 (dd, J=13.2, 8.07 Hz, 1H), 4.46-4.38 (br m, 1H), 3.96-3.87 (br m, 1H), 3.85 (d, J=10.3 Hz, 3H), 3.78-3.66 (br m, 3H), 3.65-3.52 (br m, 3H), 3.16-3.10 (br m, 1H), 3.05 (d, J=11.0 Hz, 2H), 3.00 (s, 3H), 2.94-2.79 (br m, 2H), 2.36-2.24 (br m, 2H), 2.22-2.10 (br m, 2H), 2.03-1.94 (br m, 2H), 1.93-1.81 (br m, 2H), 1.72 (s+m, total 6H), 1.71-1.58 (br m, 2H), 1.55-1.42 (br m, 2H), 1.33 (s+m, total 4H), 1.29 (s, 3H), 1.29-1.15 (br m, 1H), 1.14-0.97 (br m, 5H), 0.97, 3H), 0.92 (br s, 3H), 0.61 (br s, 3H), −0.22 (br s, 3H).

EXAMPLE 46

(R/S)-3-[4-[1-[1-(3-Carboxy-1-cyclopropyl-7-fluoro-8-methoxy-4-oxo-4H-quinolin-7-yl)pyrrolidin-3-yl] cycloprop-1-ylamino]piperidin-1-ylaminomethyl] rifamycin SV:

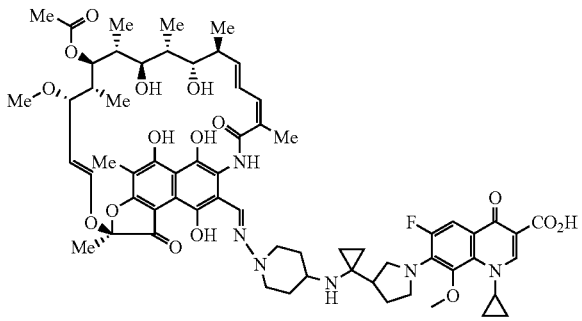

The title compound was synthesized by following the same procedure as described for the preparation of Example 45 except 1-cyclopropyl-1,4-dihydro-6,7-difluoro-8-methoxy-4-oxoquinoline-3-carboxylic acid was used in the place of 8-chloro-1,4-dihydro-1-cyclopropyl-6,7-difluoro-4-oxoquinoline-3-carboxylic acid in the step 6. The desired product was obtained as an orange solid. ESI MS m/z 1207.2 (M+H), 1175.7 (M-MeO); $^1$H NMR (400 MHz, CD$_3$OD) δ 8.75 (d, J=3.7 Hz, 1H), 8.24-8.14 (br m, 1H), 7.67 (dd, J=13.9, 8.1 Hz, 1H), 6.70-6.55 (br m, 1H), 6.42 (d, J=10.3 Hz, 1H), 6.25 (d, J=12.5 Hz, 1H), 5.93 (dd, J=15.4, 4.4 Hz, 1H), 5.08 (dd, J=12.5, 7.3 Hz, 1H), 5.04 (d, J=11.0 Hz, 1H), 4.11-4.02 (br m, 1H), 3.93-3.87 (br m, 1H), 3.77 (d, J=9.5 Hz, 1H), 3.56 (s+m, total 6H), 3.56-3.42 (br m, 1H), 3.52 (d, J=7.3 Hz, 1H), 3.00 (s+m, total 4H), 2.89-2.73 (br m, 3H), 2.73-2.65 (br m, 2H), 2.38-2.27 (br m, 1H), 2.16 (s, 3H), 2.06 (s, 3H), 2.03 (s+m, total 5H), 1.76 (s, 3H), 1.66-1.64 (m, 2H), 1.64-1.46 (m, 3H), 1.46-1.36 (m, 1H), 1.29-1.26 (br m, 3H), 1.26-1.19 (br m, 3H), 1.19-1.12 (br m, 3H), 0.95 (d, J=7.3 Hz, 3H), 0.85 (d, J=6.6 Hz, 3H), 0.76-0.69 (br m, 3H), 0.58 (d, J=5.1 Hz, 3H), −0.36 (J=6.6 Hz, 3H).

EXAMPLE 47

(R/S)-3-{[4-({1-[1-(3-Carboxy-1-(2,3-difluoro-phenyl)-6-fluoro-4-oxo-1,4-dihydro[1,8]naphthyridine-7-yl)-pyrrolidin-3-yl]-cyclopropyl}-methyl-amino)-piperidin-1-ylimino]-methyl}-rifamycin SV:

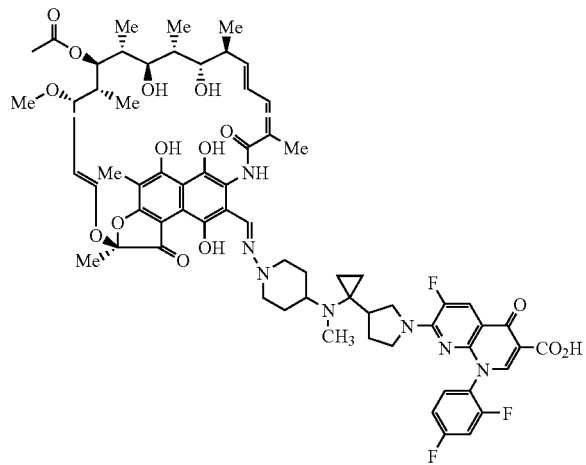

The title compound was prepared by using a similar procedure as described for the preparation of Example 16 except 7-chloro-1-(2,4-difluorophenyl)-6-fluoro-4-oxo-1,4-dihydro-[1,8]naphthyridine-3-carboxylic acid ethyl ester was used in place of 1-cyclopropyl-6,7-difluoro-8-methoxy-4-oxo-1,4-dihydro-quinoline-3-carboxylic acid in the step 6. The product was isolated as an orange solid. ESI MS m/z 1264.5 (M+H)$^+$. $^1$H NMR (400 MHz, CDCl$_3$) 1:1 mixture of diastereomers δ 13.54 (br s, 1H), 13.26 (br s, 1H), 13.23 (br s, 1H), 11.98 (br s, 1H), 8.61 (s, 1H), 8.22 (s, 1H), 7.98 (d, J=12.5 Hz, 1H), 7.37 (br s, 1H), 7.11-6.96 (m, 2H), 6.61-6.49 (m, 1H), 6.38 (d, J=11.0 Hz, 1H), 6.21 (d, J=12.5 Hz, 1H), 5.93 (d, J=14.1 Hz, 1H), 5.08 (dd, J=12.5, 7.0 Hz, 1H), 4.91 (d, J=10.2 Hz, 1H), 4.14-3.18 (m, 11H), 3.02 (s, 3H), 2.72-2.27 (m, 6H), 2.20 (s, 3H), 2.04 (s, 3H), 2.19-1.81 (m, 7H), 1.77 (m, 3H), 1.73-1.26 (m, 6H), 0.99 (d, J=6.3 Hz, 3H), 0.84 (d, J=6.3 Hz, 3H), 0.74-0.58 (m, 4H), 0.58 (d, J=6.3 Hz, 3H), −0.34 (d, J=7.0 Hz, 3H).

One skilled in the art readily appreciates that the disclosed invention is well adapted to carry out the mentioned and inherent objectives. Examples, pharmaceutical compositions, treatments, methods, procedures and techniques described herein are presented as representative of the preferred embodiments and are not intended as limitations of the scope of the invention. Thus, other uses will occur to those skilled in the art that are encompassed within the spirit and scope of the described invention.

What is claimed is:
1. A compound having a structural formula I:

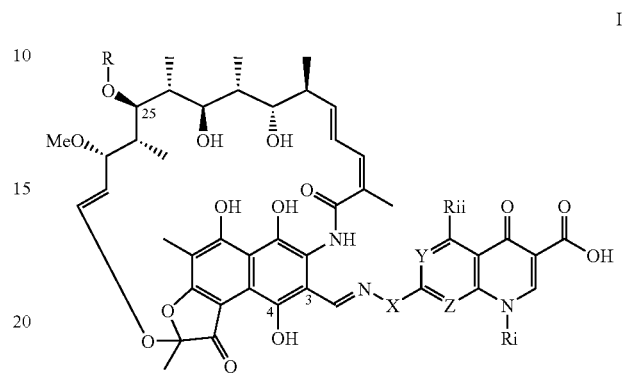

wherein:
X is a linker group selected from one or a combination of two to three of the following groups:
(a) (C$_1$-C$_6$)alkylene,
(b) (C$_3$-C$_8$)cycloalkylene,
(c) arylene,
(d) bivalent heterocyclic group containing 1 to 3 heteroatoms,
(e) —C(=O)—,
(f) —C(=N—O—R$_{11}$)—, wherein R$_{11}$ represents hydrogen, (C$_1$-C$_6$)alkyl, or substituted (C$_1$-C$_6$ alkyl),
(g) —C=N—,
(h) —O—,
(i) —S(O)$_n$—, wherein n is number between 0 and 2, and
(j) —N(R$_{12}$)—, wherein R$_{12}$ represents hydrogen, (C$_1$-C$_6$)alkyl, or substituted (C$_1$-C$_6$ alkyl),
wherein the carbon or nitrogen atoms of the linker group are optionally substituted by 1 to 3 substituents selected from (C$_1$-C$_6$)alkyl, substituted (C$_1$-C$_6$)alkyl, amino, (C$_1$-C$_6$)alkylamino, di(C$_1$-C$_6$)alkylamino, hydroxyl, or (C$_1$-C$_6$)alkoxy;
R$_i$ is (C$_1$-C$_6$)alkyl, (C$_3$-C$_6$)cycloalkyl, substituted (C$_3$-C$_6$) cycloalkyl, aryl, substituted aryl, heteroaryl, or substituted heteroaryl;
R$_{ii}$ is hydrogen, halogen, amino, nitro or methyl group;
Y is C—H, C—F, or N;
Z is C—H, C—F, C—CN, C—CF$_3$, C—Cl, C—Me, C—OMe, C—OCH$_2$F, C—OCHF$_2$, or N; and
R is hydrogen, or acetyl,
or a pharmaceutically acceptable salt of the structural formula I.

2. The compound of claim 1, wherein X is any one or a combination of the following structures:

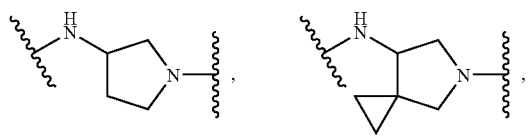

-continued
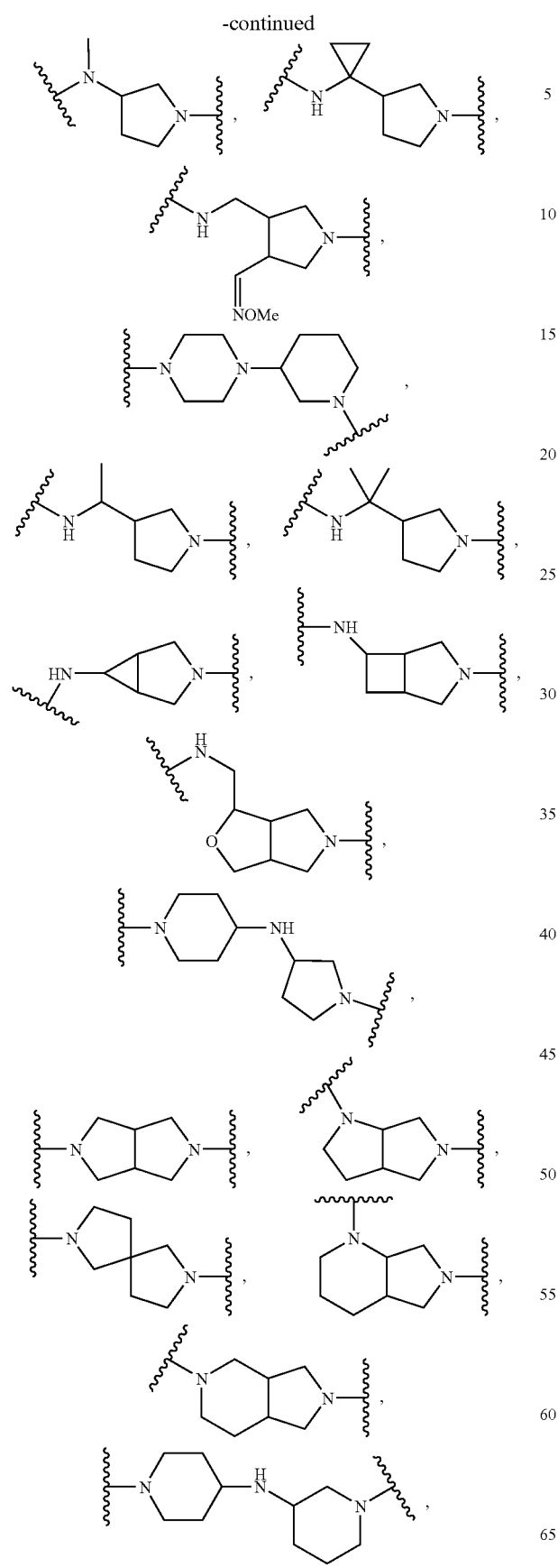
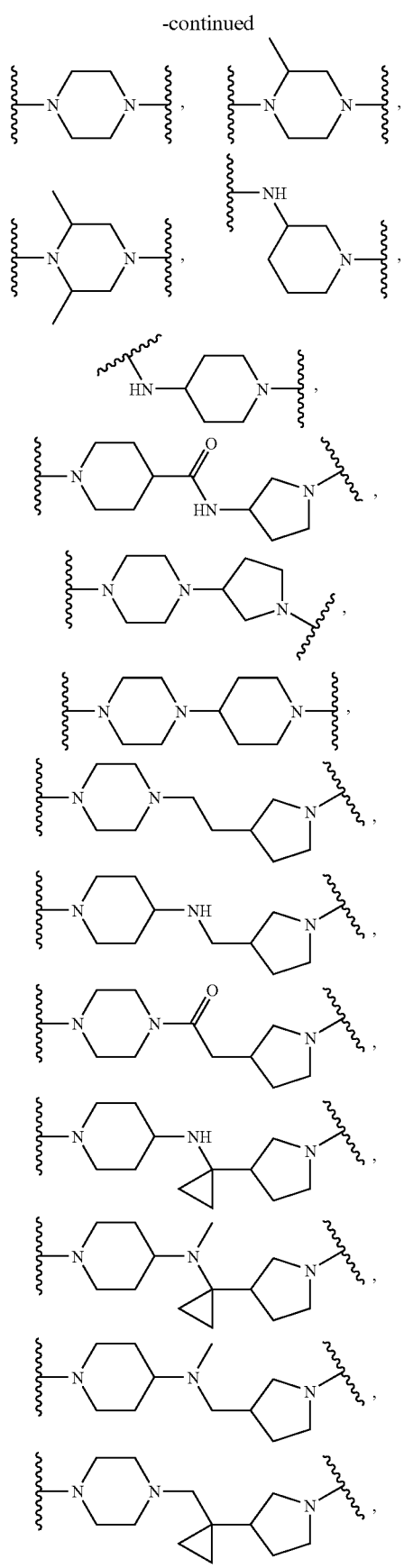

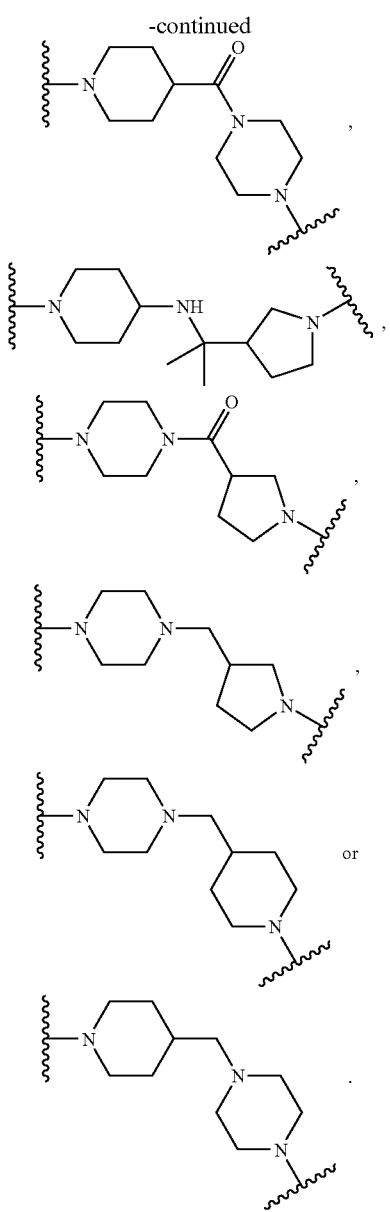

3. A rifamycin compound having a structural formula I:

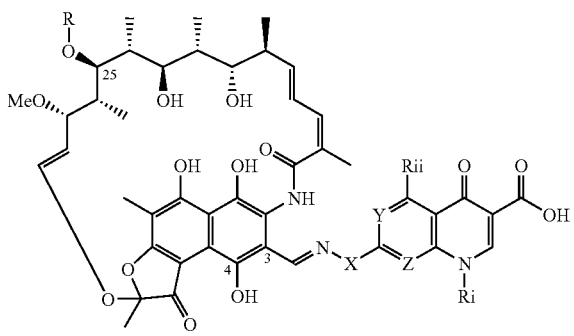

wherein,
$R_i$ is $(C_1-C_6)$alkyl, $(C_3-C_6)$cycloalkyl, substituted $(C_3-C_6)$ cycloalkyl, aryl, substituted aryl, heteroaryl, or substituted heteroaryl;

$R_{ii}$ is hydrogen, halogen, amino, nitro or methyl group;

Y is C—H, C—F, or N;

Z is C—H, C—F, C—CN, C—$CF_3$, C—Cl, C—Me, C—OMe, C—$OCH_2F$, C—$OCHF_2$, or N;

R is hydrogen or acetyl, and

X is a linker group selected from one or a combination of two to three of the following groups:

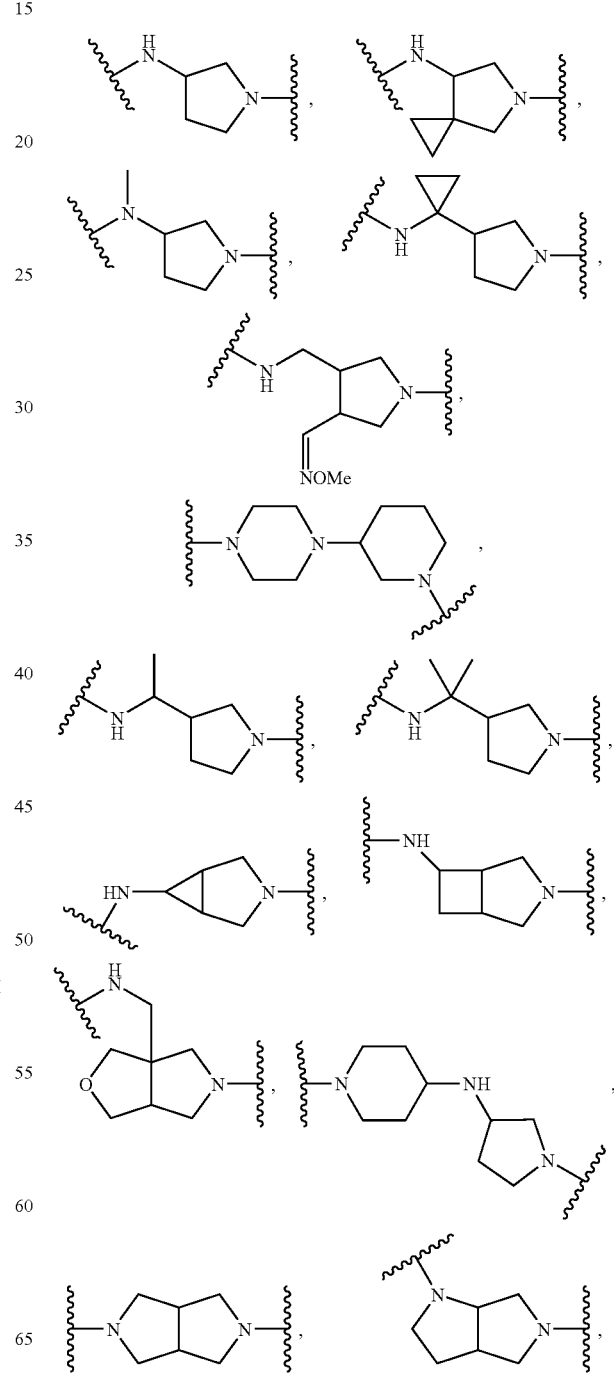

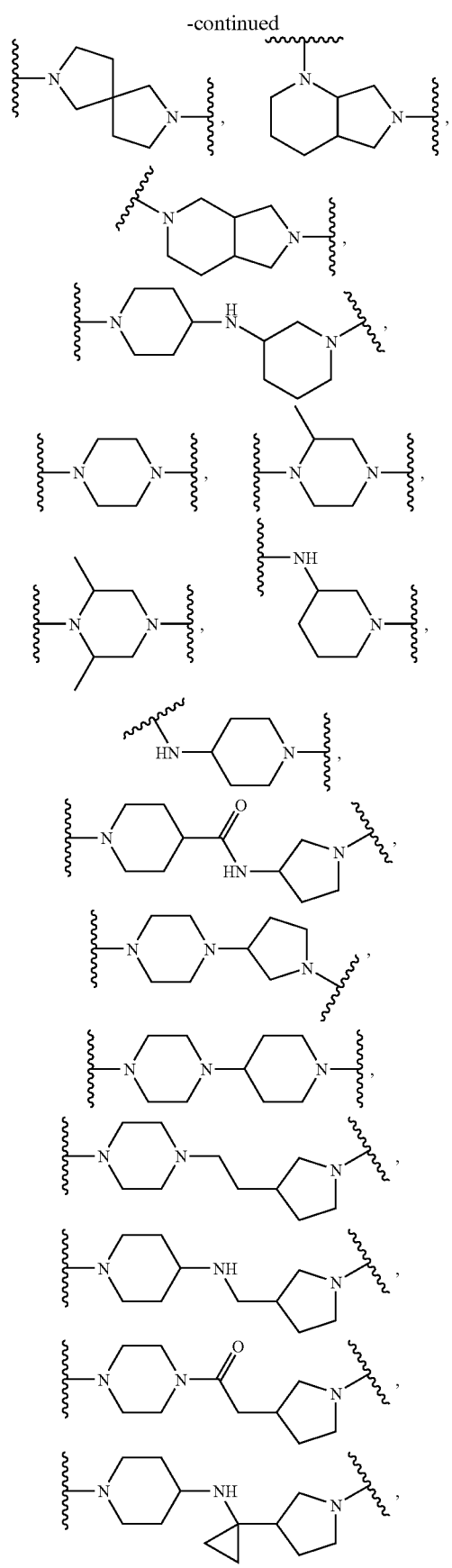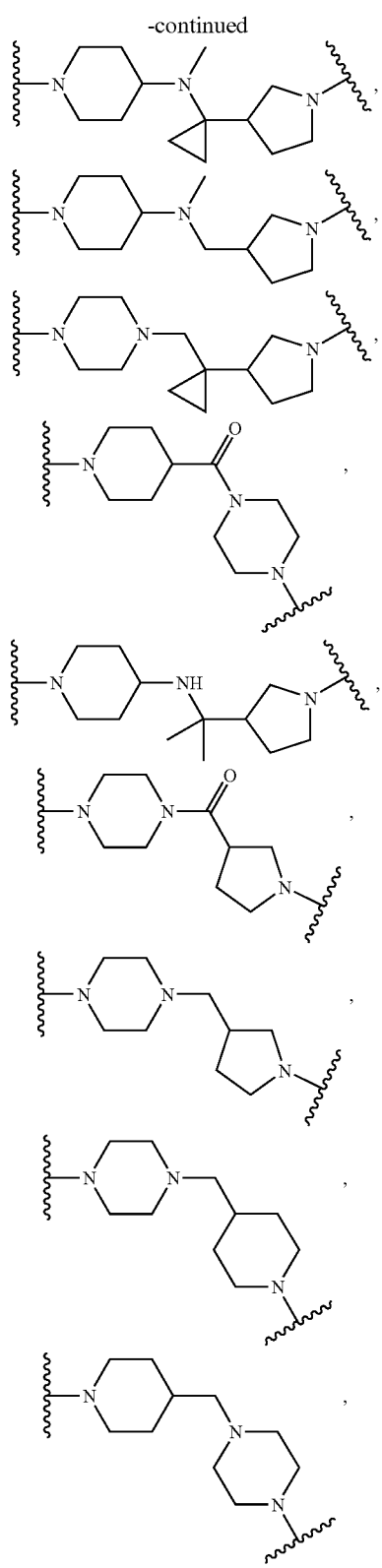
or a pharmaceutically acceptable salt of the structural formula I above.
4. A method of treating a bacterial infection in a subject comprising administering to the subject an effective amount of the compound of claim 1.

5. The method of claim 4, wherein the bacterial infection is caused by a drug-resistant bacterium.

6. A compound of the formula: 3-[4-(3-Carboxy-1-cyclopropl-6-fluoro-4-oxo-1,4-dihydroquinolin-7-yl)piperazin-1-yl-aminomethylenyl]rifamycin SV:

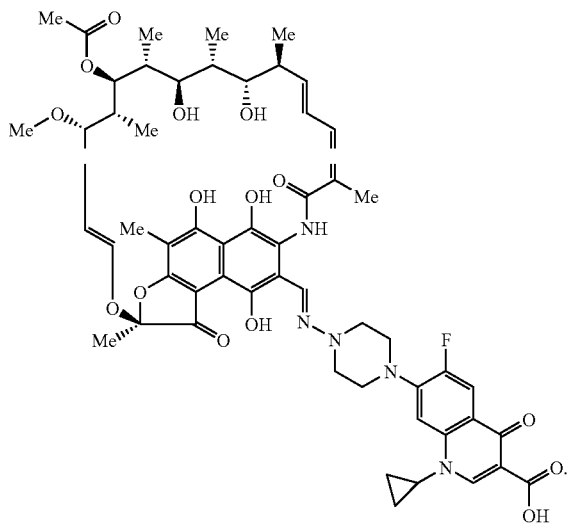

7. A compound of the formula: 3-[4-(3-Carboxy-1-cyclopropl-6-fluoro-4-oxo-1,4-dihydroquinolin-7-yl)-piperazin-1-yl-aminomethylenyl]rifamycin S:

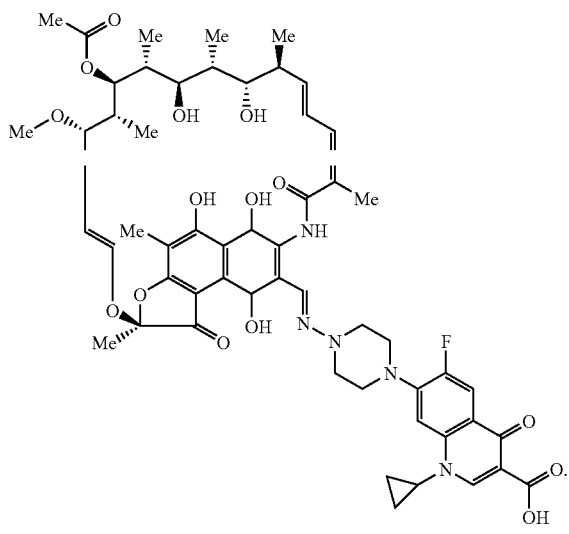

8. A compound of the formula: (R/S)-3-[1-(8-chloro-3-carboxy-1-cyclopropyl-6-fluoro-4-oxo-1,4-dihydroquinolin-7-yl)-pyrrolidin-3-ylhydrazinomethylenyl]rifamycin SV:

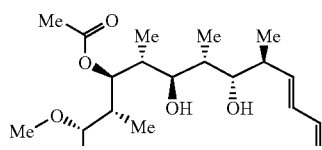

-continued

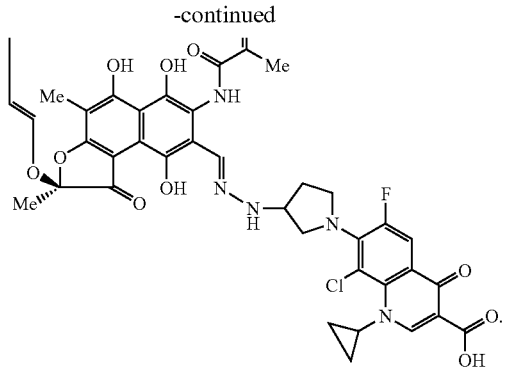

9. A compound of the formula: (R/S)-3-[4-(3-Carboxy-1-cyclopropyl-6-fluoro-8-methoxy-4-oxo-1,4-dihydroquinolin-7-yl)-2-methyl-piperazin-1-yl-aminomethylenyl]rifamycin SV:

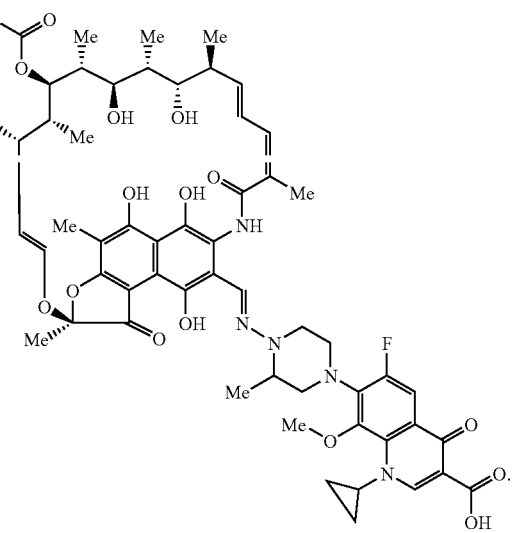

10. A compound of the formula: (R/S)-3-[4-(3-Carboxy-1-ethyl-6,8-difluoro-8-4-oxo-1,4-dihydroquinolin-7-yl)-2-methyl-piperazin-1-yl-aminomethylenyl]rifamycin SV:

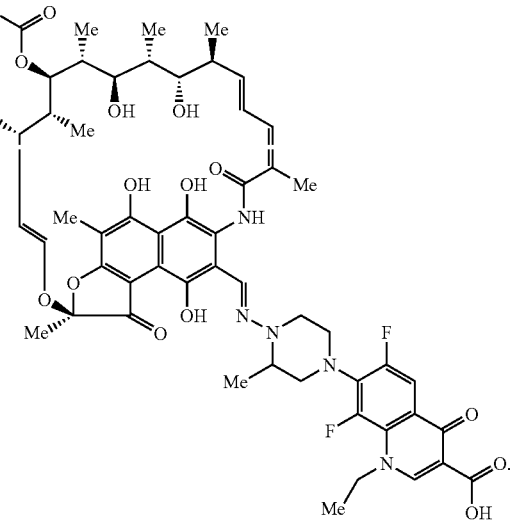

11. A compound of the formula: (R/S)-3-[1-[3-Carboxy-1-(2,4-difluoro-phenyl)-6-fluoro-4-oxo-1,4-dihydro-[1,8]naphthyridin-7-yl]-pyrrolidinyl-3-hydrazinomethylenyl]rifamycin SV:

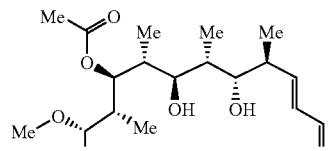

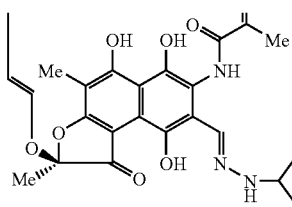

12. A compound of the formula: 3-[4-[3-Carboxy-1-(2,4-difluoro-phenyl)-6-fluoro-4-oxo-1,4-dihydro-[1,8]naphthyridine-7-yl]-piperazin-1-ylaminomethylenyl]rifamycin S:

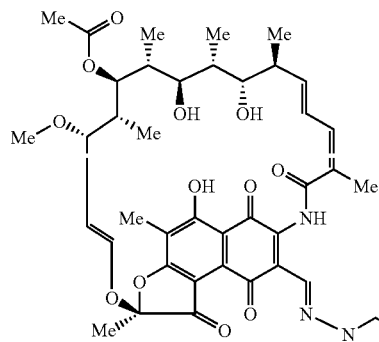

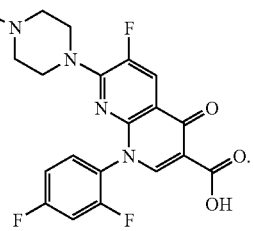

13. A compound of the formula: (R/S)-3-[1-(3-Carboxy-1-cyclopropyl-6-fluoro-4-oxo-1,4-dihydroquinolin-7-yl)-pyrrolidin-3-yl-N'-(1-methyl-piperidin-4-yl)-hydrazinomethylenyl]rifamycin SV:

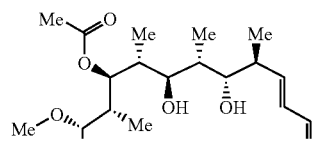

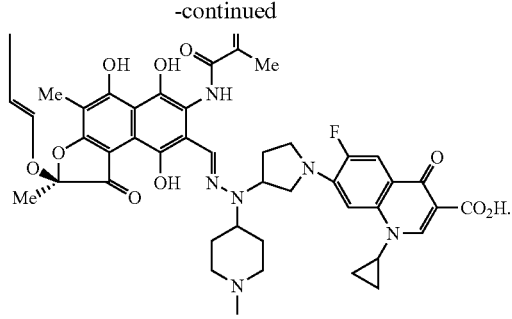

14. A compound of the formula: (R/S)-3-[4-(3-Carboxy-1-cyclopropyl-6-fluoro-8-methoxy-4-oxo-1,4-dihydroquinolin-7-yl)-2-methylpiperazin-1-yl-aminomethylenyl]rifamycin S:

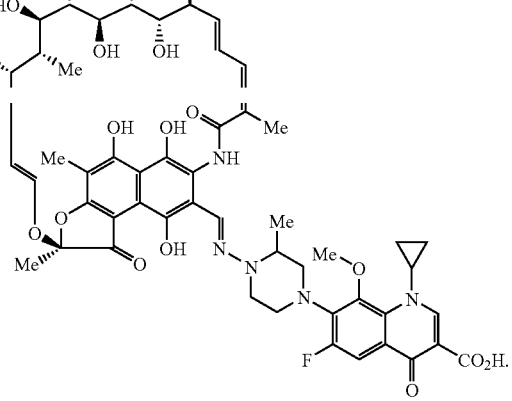

15. A compound of the formula: 3-[6-(3-Carboxy-1-cyclopropyl-6-fluoro-8-methoxy-4-oxo-1,4-dihydroquinolin-7-yl)-octahydropyrrolo[3,4-b]pyridin-1-yl-aminomethylenyl]rifamycin S:

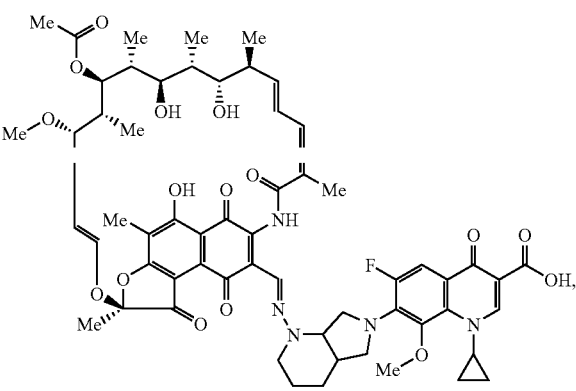

16. A compound of the formula: 3-[4-(3-Carboxy-1-cyclopropyl-6-fluoro-8-methoxy-4-oxo-1,4-dihydroquinolin-7-yl)-2-methyl-piperazin-1-yl-aminomethylenyl]-25-deacetyirifamycin S:

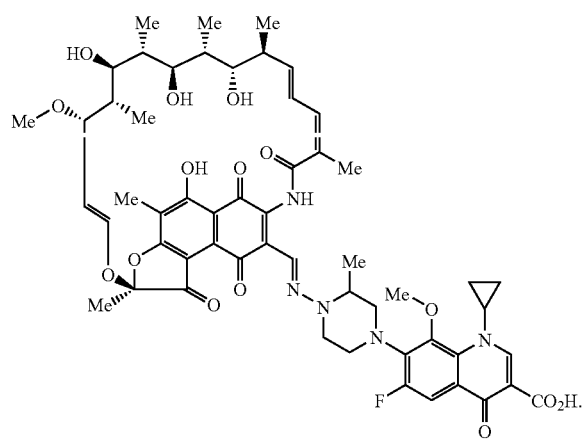

17. A compound of the formula: 3-[4-(3-Carboxy-1-cyclopropyl-6-fluoro-8-methoxy-4-oxo-1,4-dihydroquinolin-7-yl)-2-methyl-piperazin-1-yl-aminomethylenyl]-25-deacetylrifamycin SV:

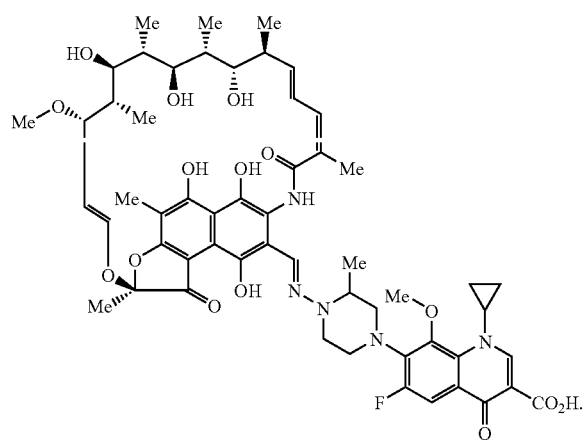

18. A compound of the formula: 3-[4-[3-Carboxy-1-(2,4-difluoro-phenyl)-6-fluoro-4-oxo-1,4-dihydro-[1,8]naphthyridine-7-yl]-piperazin-1-ylaminomethylenyl]rifamycin SV:

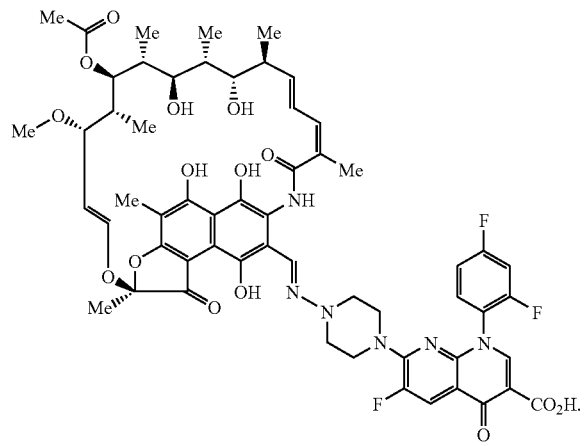

19. A compound of the formula: (R/S)-3-[1-(3-Carboxy-1-cyclopropyl-6-fluoro-4-oxo-1,4-dihydroquinolin-7-yl)-pyrrolidin-3-yl-N'-methylhydrazinomethylenyl]rifamycin SV:

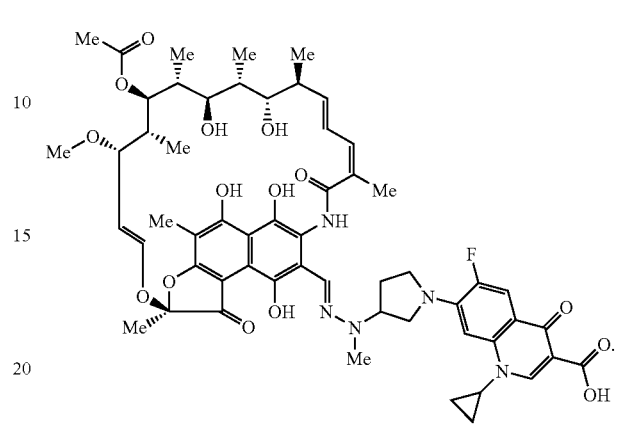

20. A compound of the formula: (R/S)-3-[(4-{1-[1-(3-Carboxy-1-cyclopropyl-6-fluoro-8-methoxy-4-oxo-1,4-dihydro-quinoline-7-yl)-pyrrolidin-3-yl-cyclopropyl]-methyl)-amino}-piperidin-1-ylimino)-methyl]-rifamycin S:

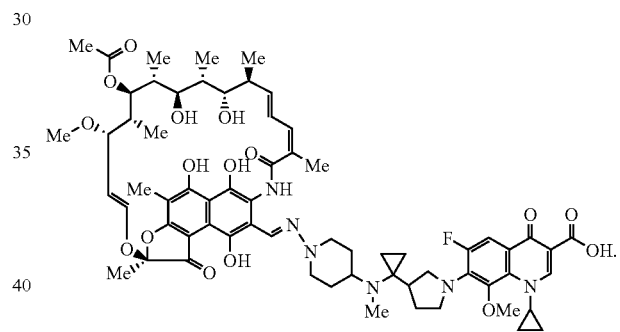

21. A compound of the formula: (R/S)-3-{[4-({1-[1-(3-Carboxy-8-chloro-1-cyclopropyl-6-fluoro-4-oxo-1,4-dihydro-quinolin-7-yl)-pyrrolidin-3-yl]-cyclopropyyl}-methyl-amino)-piperidin-1-ylimino]-methyl}-rifamycin SV:

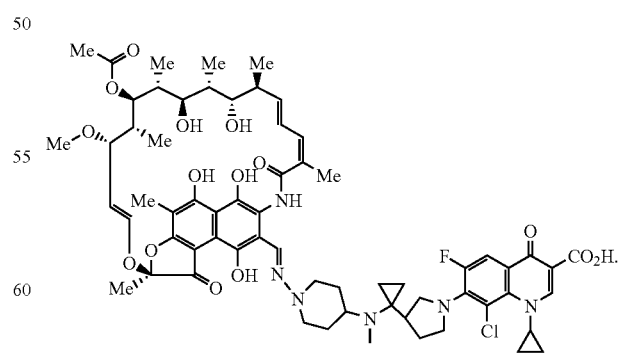

22. A compound of the formula: 3-[4-(3-Carboxy-1-ethyl-6-fluoro-4-oxo-1,4-dihydroquinolin-7-yl)-piperazin-1-yl-aminomethylenyl]-rifamycin SV:

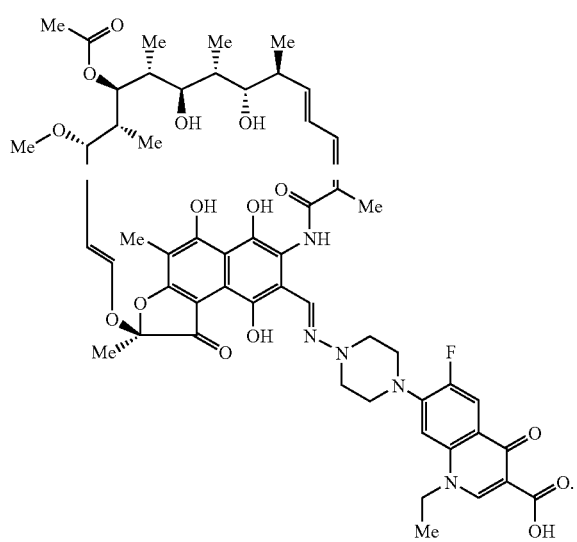

23. A compound of the formula: 3-[4-(3-Carboxy-1-ethyl-6-fluoro-4-oxo-1,4-dihydro-[1,8]naphthyridine-7-yl)-piperazin-1-yl-aminomethylenyl]-rifamycin SV:

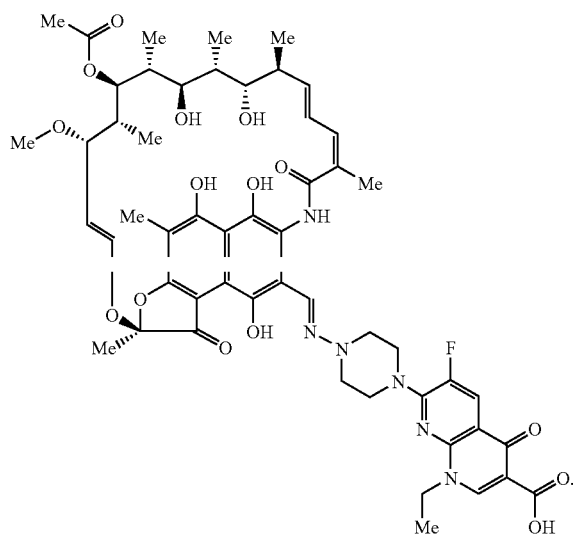

24. A compound of the formula: 3-[4-(3-Carboxy-1-cyclopropyl-6-fluoro-8-methoxy-4-oxo-1,4-dihydroquinolin-7-yl)-piperazin-1-yl-aminomethylenyl]-rifamycin SV:

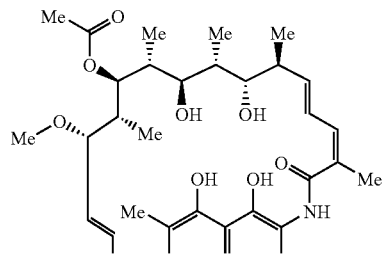

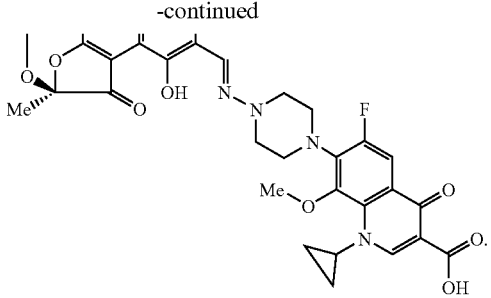

25. A compound of the formula: (R/S)-3-[1-(3-Carboxy-1-cyclopropyl-6-fluoro-8-methoxy-4-oxo-1,4-dihydroquinolin-7-yl)-pyrrolidinyl-3-hydrazino-methylenyl]-yifamycin SV:

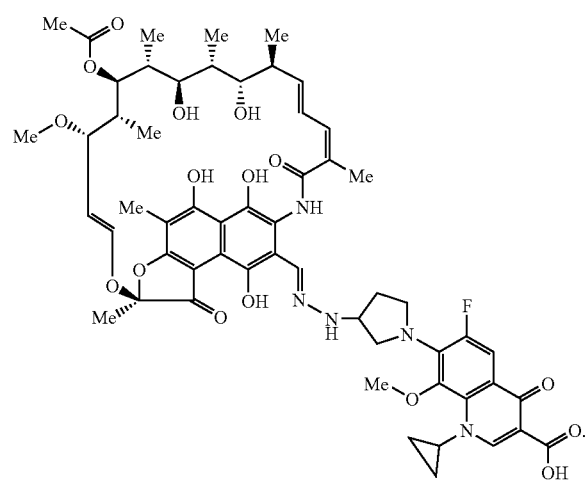

26. A compound of the formula: (R/S)-3-[1-(3-Carboxy-1-cyclopropyl-6-fluoro-8-methoxy-4-oxo-1,4-dihydroquinolin-7-yl)-pyrrolidinyl-3-methylhydrazino-methylenlyl]-rifamycin SV:

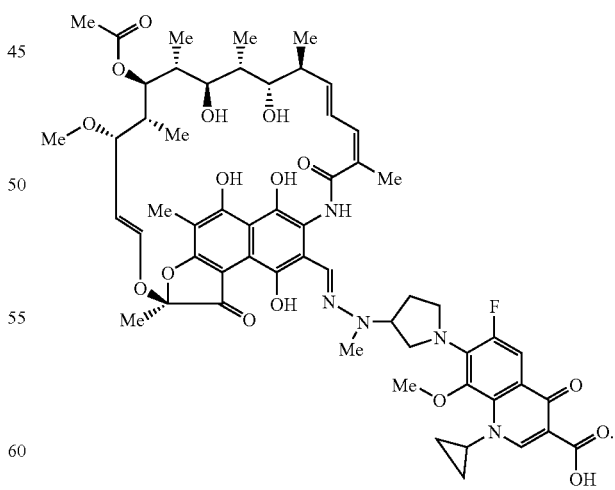

27. A compound of the formula: (R/S)-3-[4-(3-Carboxy-1-cyclopropyl-6-fluoro-8-methoxy-4-oxo-1,4-dihydroquinolin-7-yl)-3-carboxy-piperazin-1-yl-aminomethylenyl]-rifamycin SV:

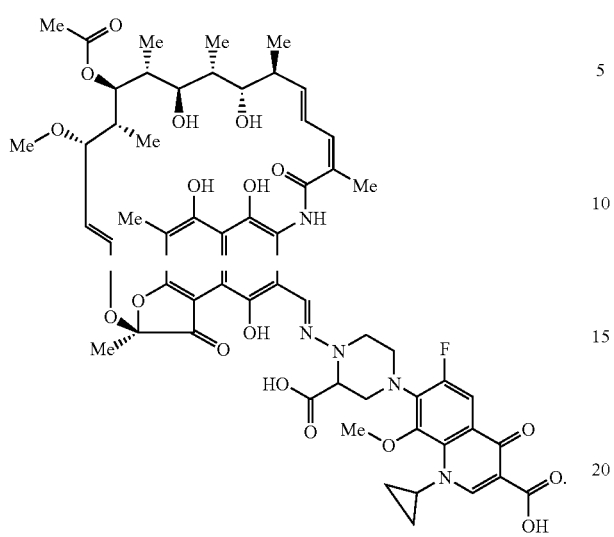

28. A compound of the formula: (R/S)-3-[1-(3-Carboxy-1-cyclopropyl-6-fluoro-8-methoxy-4-oxo-1,4-dihydroquinolin-7-yl)-piperidin-3-hydrazino-methylenyl]-rifamycin SV:

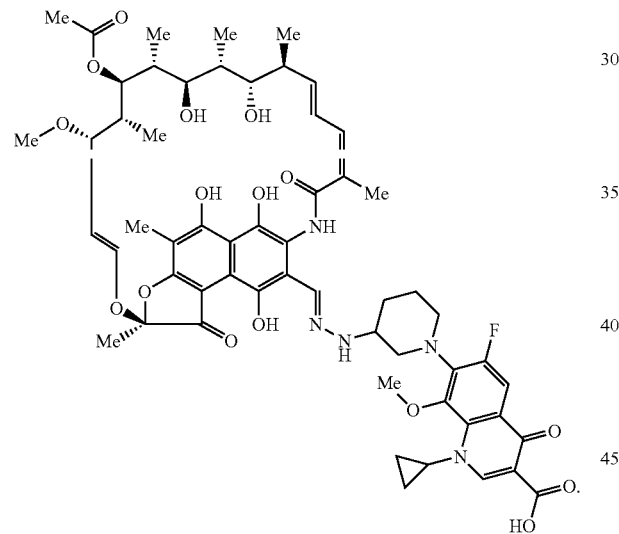

29. A compound of the formula: 3-{4-[1-(3-Carboxy-1-cyclopropyl-6-fluoro-8-methoxy-4-oxo-1,4-dihydroquinolin-7-yl)-piperazin-4-yl]-piperidin-1-yl-aminomethylenyl}-rifamycin SV:

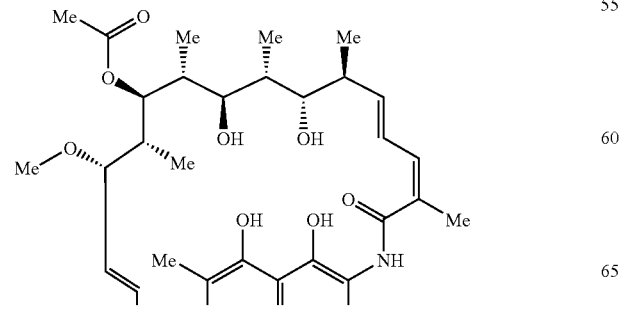

-continued

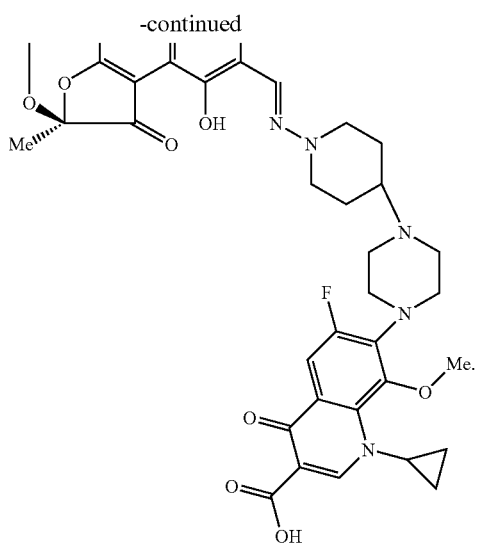

30. A compound of the formula: (R/S)-3-{4-[1-(3-Carboxy-1-cyclopropyl-6-fluoro-8-methoxy-4-oxo-1,4-dihydroquinolin-7-yl)-pyrrolidin-3-ylamino]-piperidin-1-yl-aminomethylenyl}-rifamycin SV:

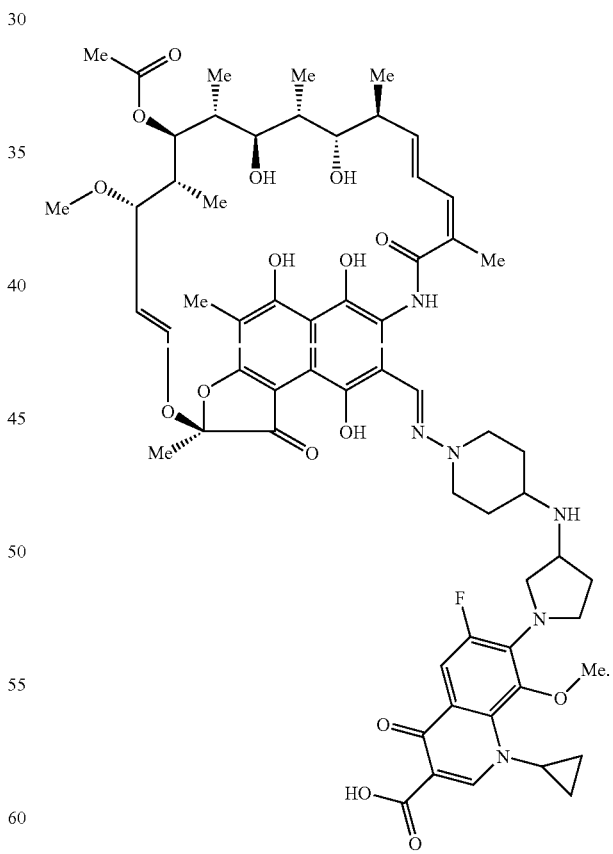

31. A compound of the formula: 3-{4-[1-(3-Carboxy-1-cyclopropyl-6-fluoro-8-methoxy-4-oxo-1,4-dihydroquinolin-7-yl)-piperidin-4-yl]-piperazin-1-yl-aminomethylenyl}-rifamycin SV:

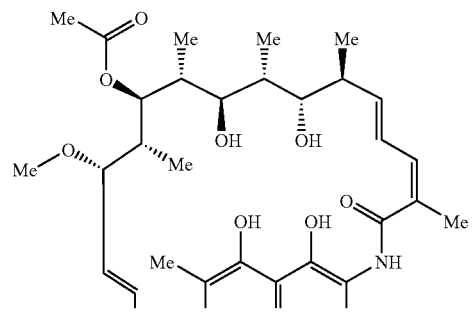

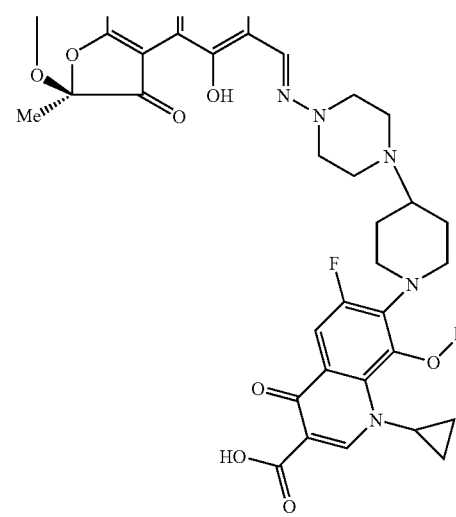

32. A compound of the formula: (R/S)-3-{3-[1-(3-carboxy-1-cyclopropyl-6-fluoro-8-methoxy-4-oxo-1,4-dihydroquinolin-7-yl)-piperazin-4-yl]-pyrrolidinyl-1-hydrazinomethylenyl}-rifamycin SV:

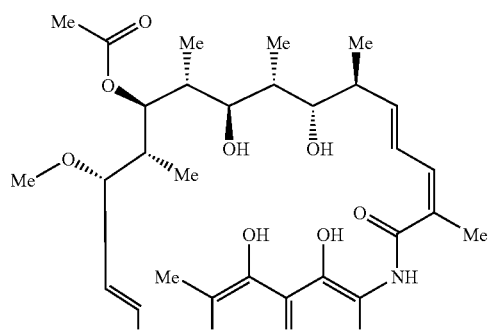

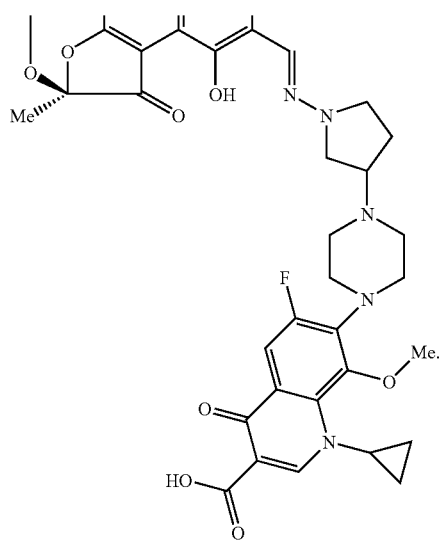

33. A compound of the formula: (R/S)-3-[1-(3-Carboxy-1-cyclopropyl-6-fluoro-8-methoxy-4-oxo-1,4-dihydroquinolin-7-yl)-pyrrolidinyl-3-isopropylhydrazino-methylenyl]-rifamycin SV:

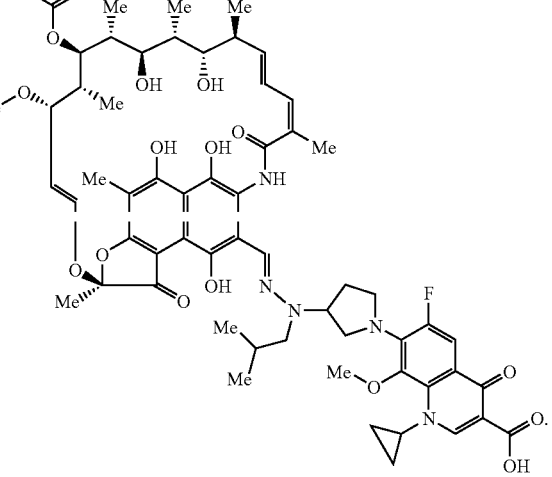

34. A compound of the formula: (R/S)-3-[1-(3-carboxy-1-cyclopropyl-6-fluoro-8-methoxy-4-oxo-1,4-dihydroquinolin-7-yl)-pyrrolidinyl-3-(pyridin-2-ylmethyl)hydrazino-methylenyl]-rifamycin SV:

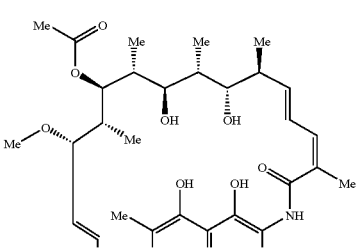

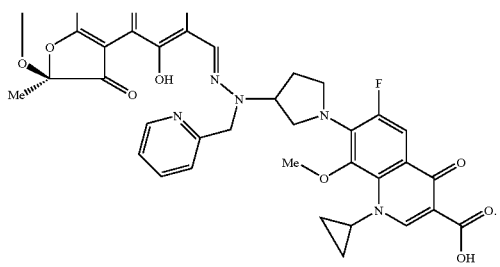

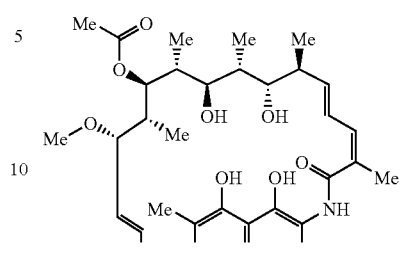

35. A compound of the formula: (R/S)-3-{4-[1-(3-Carboxy-8-chloro-1-cyclopropyl-6-fluoro-4-oxo-1,4-dihydroquinolin-7-yl)-pyrrolidin-3-ylcarbamoyl]-piperidin-1-yl-aminomethylenyl}-rifamycin SV:

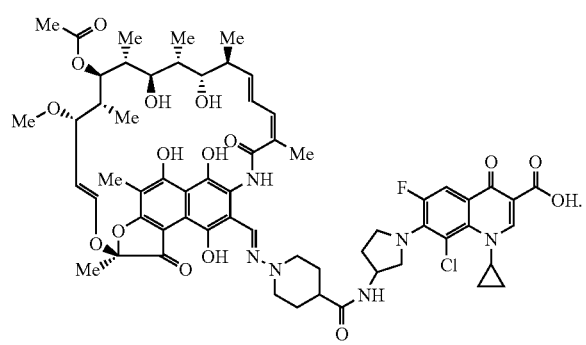

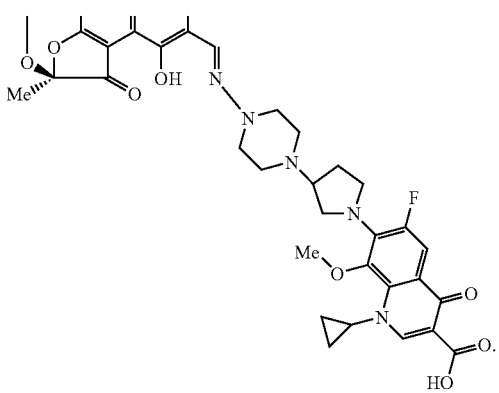

38. A compound of the formula: (R/S)-3-{4-[1-(3-Carboxy-1-(2,3-difluoro-phenyl)-6-fluoro-4-oxo-1,4-dihydro[1,8]naphthyridine-7-yl)-pyrrolidin-3-yl]-piperazin-1-yl-aminomethylenyl}-rifamycin SV:

36. A compound of the formula: 3-{4-[4-(3-Carboxy-1-cyclopropyl-6-fluoro-8-methoxy-4-oxo-1,4-dihydroquinolin-7-yl)-piperazine-1-yl-carbonyl]-piperidin-1-yl-aminomethylenyl}-rifamycin SV:

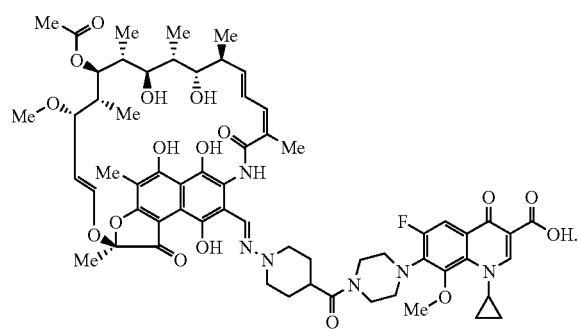

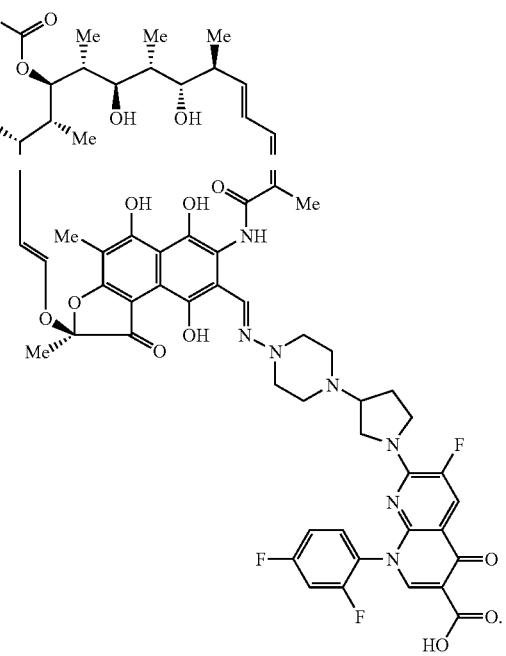

37. A compound of the formula: (R/S)-3-{4-[1-(3-Carboxy-1-cyclopropyl-6-fluoro-8-methoxy-4-oxo-1,4-dihydroquinolin-7-yl)-pyrrolidin-3-yl]-piperazin-1-yl-aminomethylenyl}-rifamycin SV:

39. A compound of the formula: 3-[4-(3-Carboxy-1-cyclopropyl-6-fluoro-4-oxo-1,4-dihydro-[1,8]naphthyridine-7-yl)-piperazin-1-yl-aminomethylenyl]-rifamycin SV:

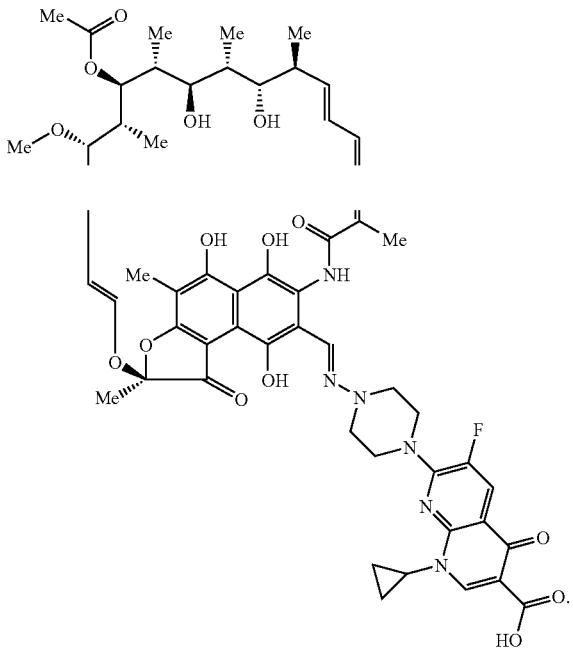

40. A compound of the formula: (R/S)-3-{4-[1-(3-Carboxy-1-(2,4-difluoro-phenyl)-6-fluoro-4-oxo-1,4-dihydro-[1,8]naphthyridine-7-yl)-pyrrolidin-3-yl-carbonyl]-piperazin-1-yl-aminomethylenyl}-rifamycin SV:

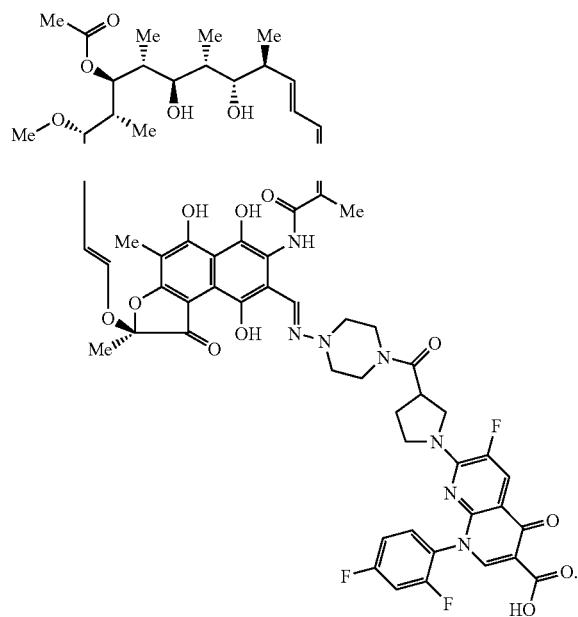

41. A compound of the formula: (R/S)-3-{4-[1-(3-Carboxy-1-cyclopropyl-6-fluoro-8-methoxy-4-oxo-1,4-dihydroquinoline-7-yl)-pyrrolidin-3-yl-cyclopropyl]-piperazin-1-yl-aminomethylenyl}-rifamycin SV:

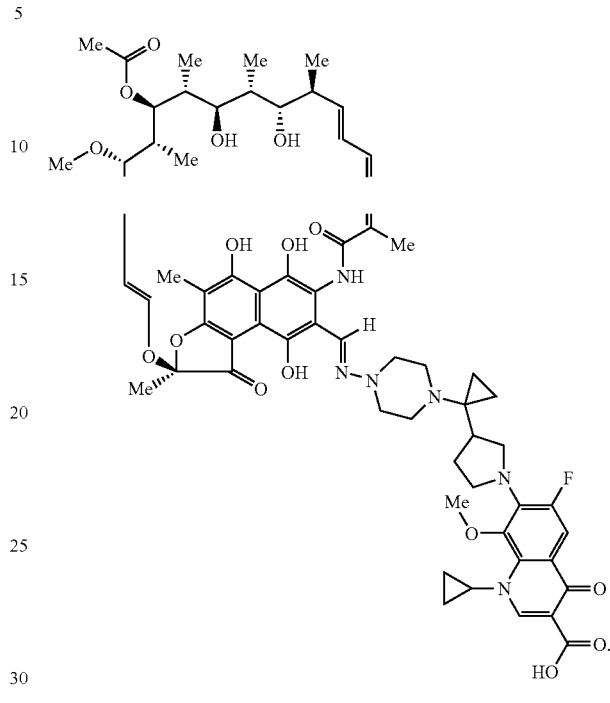

42. A compound of the formula: (R/S)-3-{4-[1-(3-Carboxy-8-chloro-1-cyclopropyl-6-fluoro-4-oxo-1,4-dihydroquinoline-7-yl)-pyrrolidin-3-yl-cyclopropyl]-piperazin-1-yl-aminomethylenyl}-rifamycin SV:

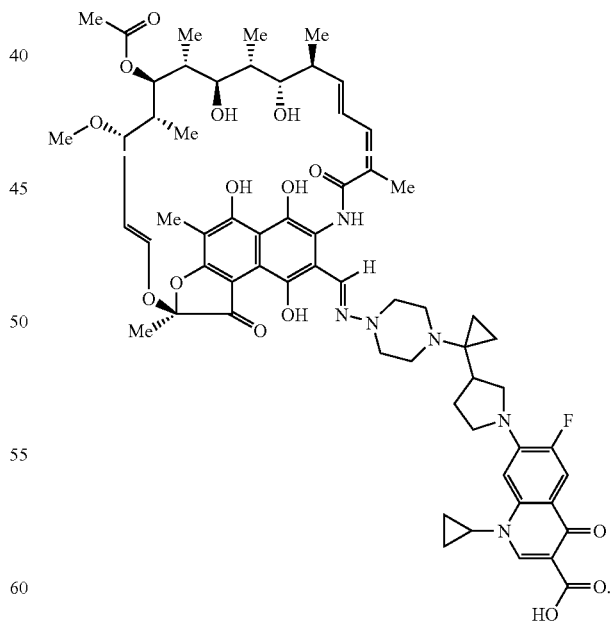

43. A compound of the formula: (R/S)-3-[1-(3-Carboxy-8-chloro-1-cyclopropyl-6-fluoro-4-oxo-1,4-dihydroquinoline-7-yl)-pyrrolidin-3-yl-methyl-hydrazino-methylenyl]-rifamycin SV:

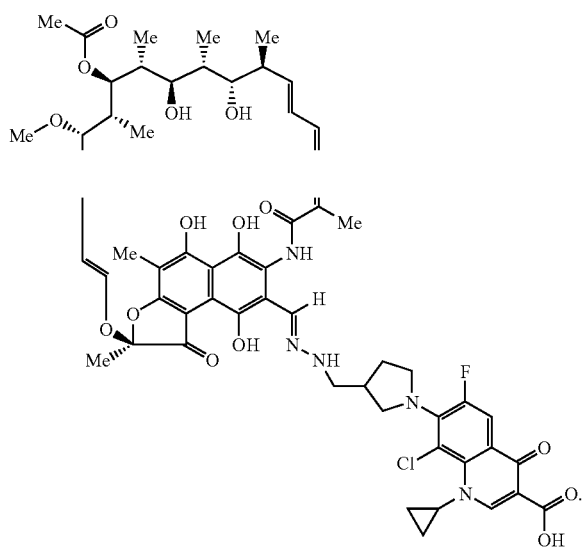

44. A compound of the formula: 3-[4-(3-Carboxy-8-chloro-1-cyclopropyl-6-fluoro-4-oxo-1,4-dihydroquinolin-7-yl)-piperazin-1-yl-aminomethylenyl]-rifamycin SV:

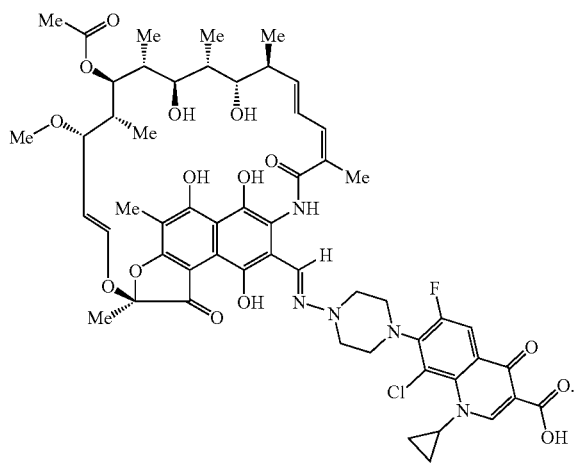

45. A compound of the formula: 3-{4-[1-(3-Carboxy-1-cyclopropyl-6-fluoro-8-methoxy-4-oxo-1,4-dihydroquinolin-7-yl)-pyrrolidin-3-yl-ethylamino]-piperidin-1-yl-aminomethylenyl}-rifamycin SV:

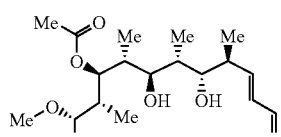

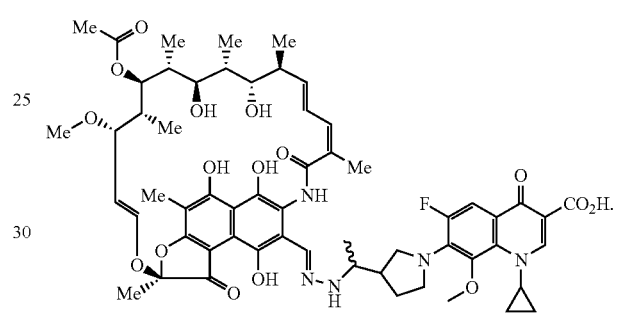

46. A compound of the formula: 3-({1-[1-(3-Carboxy-1-cyclopropyl-6-fluoro-8-methoxy-4-oxo-1,4-dihydro-quinolin-7-yl)-pyrrolidin-3-yl]-ethyl}-hydrazinomethylenyl)-rifamycin SV:

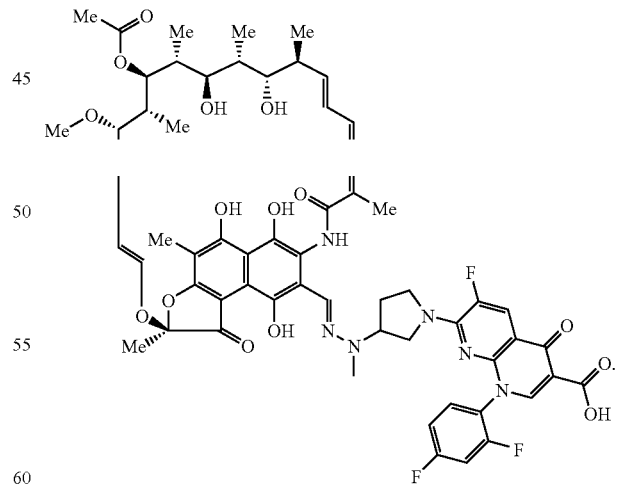

47. A compound of the formula: (R/S)-3-[1-[3-Carboxy-1-(2,4-difluoro-phenyl)-6-fluoro-4-oxo-1,4-dihydro-[1,8]naphthyridin-7-yl]-pyrrolidinyl-3-methylhydrazinomethylenyl]rifamycin SV:

48. A compound of the formula: (R/S)-3-[9-fluoro-3-methyl-10-(3-methyl-piperazin-1-hydrazinomethylenyl)-7-oxo-7H-pyrido[1,2,3-de]-1,4-benzoxazine-6-carboxylic acid]rifamycin SV:

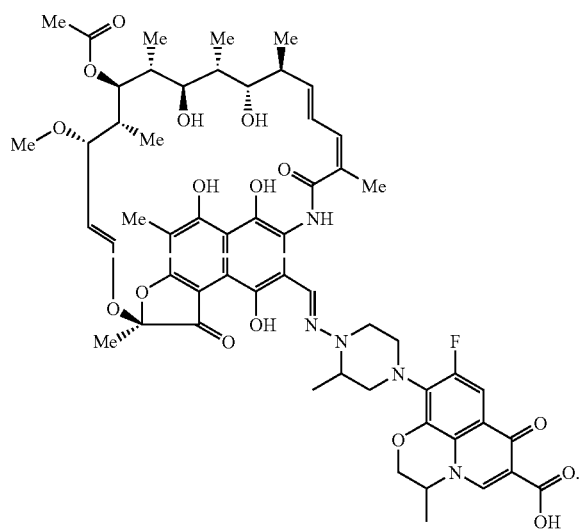

49. A compound of the formula: (R/S)-3-[4-[1-[1-(3-Carboxy-1-cyclopropyl-7-fluoro-8-chloro-4-oxo-4H-quinolin-7-yl)pyrrolidin-3-yl]cycloprop-1-ylamino]piperidin-1-ylaminomethylenyl]rifamycin SV:

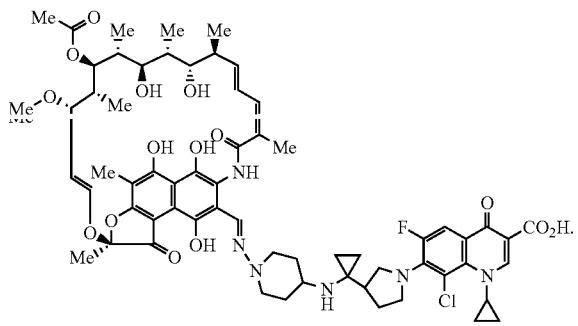

50. A compound of the formula: (R/S)-3-[4-[1-[1-(3-Carboxy-1-cyclopropyl-7-fluoro-8-methoxy-4-oxo-4H-quinolin-7-yl)pyrrolidin-3-yl]cycloprop-1-ylamino]piperidin-1-ylaminomethyl]rifamycin SV:

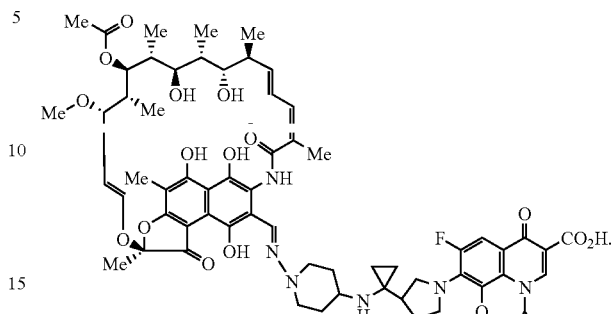

51. A compound of the formula: (R/S)-3-{[4-({1-[1-(3-Carboxy-1-(2,3-difluoro-phenyl)-6-fluoro-4-oxo-1,4-dihydro[1,8]naphthyridine-7-yl)-pyrrolidin-3-yl]-cyclopropyl}-methyl-amino)-piperidin-1-ylimino]-methyl}-rifamycin SV:

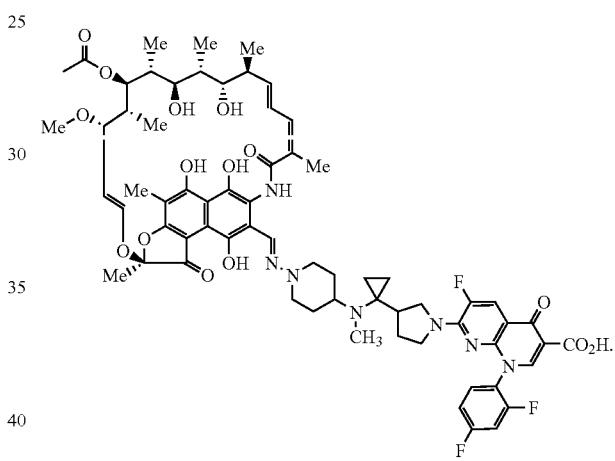

* * * * *